(12) United States Patent
Wong et al.

(10) Patent No.: US 10,690,671 B2
(45) Date of Patent: Jun. 23, 2020

(54) ULTRAPURIFIED DSBA AND DSBC AND METHODS OF MAKING AND USING THE SAME

(71) Applicant: Genentech, Inc., South San Francisco, CA (US)

(72) Inventors: Marc Wong, San Carlos, CA (US); Liliana T. Yee, San Francisco, CA (US); Amy Lim, Palo Alto, CA (US); Chris B. Fong, San Leandro, CA (US)

(73) Assignee: Genentech, Inc., South San Francisco, CA (US)

(*) Notice: Subject to any disclaimer, the term of this patent is extended or adjusted under 35 U.S.C. 154(b) by 0 days.

(21) Appl. No.: 16/044,360

(22) Filed: Jul. 24, 2018

(65) Prior Publication Data

US 2019/0056399 A1 Feb. 21, 2019

Related U.S. Application Data

(62) Division of application No. 15/061,943, filed on Mar. 4, 2016, now Pat. No. 10,073,098.

(60) Provisional application No. 62/129,701, filed on Mar. 6, 2015.

(51) Int. Cl.
| | |
|---|---|
| *G01N 33/53* | (2006.01) |
| *G01N 33/573* | (2006.01) |
| *C12N 9/02* | (2006.01) |
| *C12N 9/90* | (2006.01) |
| *C07K 1/22* | (2006.01) |
| *C07K 16/40* | (2006.01) |
| *A61K 38/00* | (2006.01) |

(52) U.S. Cl.
CPC .......... *G01N 33/573* (2013.01); *C07K 1/22* (2013.01); *C07K 16/40* (2013.01); *C12N 9/0051* (2013.01); *C12N 9/90* (2013.01); *C12Y 108/04002* (2013.01); *C12Y 503/04001* (2013.01); *A61K 38/00* (2013.01); *G01N 2333/90212* (2013.01); *G01N 2333/99* (2013.01); *Y02A 50/473* (2018.01)

(58) Field of Classification Search
CPC .................................................. G01N 33/573
See application file for complete search history.

(56) References Cited

U.S. PATENT DOCUMENTS

| | | |
|---|---|---|
| 3,645,090 A | 2/1972 | Mochizuki et al. |
| 3,691,016 A | 9/1972 | Patel |
| 3,940,475 A | 2/1976 | Gross |
| 3,969,287 A | 7/1976 | Jaworek et al. |
| 4,195,128 A | 3/1980 | Hildebrand et al. |
| 4,229,537 A | 10/1980 | Hodgins et al. |
| 4,247,642 A | 1/1981 | Hirohara et al. |
| 4,330,440 A | 5/1982 | Ayers et al. |
| 4,376,110 A | 3/1983 | David et al. |
| 4,676,980 A | 6/1987 | Segal et al. |
| 4,737,456 A | 4/1988 | Weng et al. |
| 4,816,567 A | 3/1989 | Cabilly et al. |
| 5,264,365 A | 11/1993 | Georgiou et al. |
| 5,500,362 A | 3/1996 | Robinson et al. |
| 5,508,192 A | 4/1996 | Georgiou et al. |
| 5,571,894 A | 11/1996 | Wels et al. |
| 5,587,458 A | 12/1996 | King et al. |
| 5,591,828 A | 1/1997 | Bosslet et al. |
| 5,639,635 A | 6/1997 | Joly et al. |
| 5,641,870 A | 6/1997 | Rinderknecht et al. |
| 5,648,237 A | 7/1997 | Carter |
| 5,693,780 A | 12/1997 | Newman et al. |
| 5,731,168 A | 3/1998 | Carter et al. |
| 5,789,199 A | 8/1998 | Joly et al. |
| 5,821,337 A | 10/1998 | Carter et al. |
| 5,856,203 A | 1/1999 | Robinson |
| 6,027,888 A | 2/2000 | Georgiou et al. |
| 6,083,715 A | 7/2000 | Georgiou et al. |
| 7,521,541 B2 | 4/2009 | Eigenbrot et al. |
| 8,241,901 B2 | 8/2012 | Huang et al. |
| 10,073,098 B2 | 9/2018 | Wong et al. |
| 2006/0025576 A1 | 2/2006 | Miller et al. |
| 2006/0030022 A1* | 2/2006 | Beckwith ............ C12N 9/0004 435/252.3 |
| 2008/0069820 A1 | 3/2008 | Fuh et al. |
| 2009/0182127 A1 | 7/2009 | Kjaergaard et al. |
| 2016/0370369 A1 | 12/2016 | Wong et al. |

FOREIGN PATENT DOCUMENTS

| | | |
|---|---|---|
| EP | 0 404 097 B1 | 9/1996 |
| EP | 0 992 588 A1 | 4/2000 |
| WO | WO-1993/08829 A1 | 5/1993 |
| WO | WO-1993/11161 A1 | 6/1993 |
| WO | WO-1993/16185 A2 | 8/1993 |

(Continued)

OTHER PUBLICATIONS

Arie, J.-P. et al. (Jan. 2001) "Chaperone Function of FkpA, a Heat Shock Prolyl Isomerase, in the Periplasm of *Escherichia coli,*" *Mol. Microbiol.* 39(1):199-210.

Bachmann, B.J. (1987). "Derivations and Genotypes of Some Mutant Derivatives of *Escherichia coli* K-12," Chapter 72 in *Cellular and Molecular Biology*, 2:1190-1219.

Bader, M.W. et al. (Apr. 2, 2001). "Turning a Disulfide Isomerase Into an Oxidase: DsbC Mutants That Imitate DsbA," *The EMBO Journal* 20(7):1555-1562.

Bass, S. et al. (1990). "Hormone Phage: An Enrichment Method for Variant Proteins With Altered Binding Properties," *Proteins* 8(4):309-314.

Bothmann, H. et al. (Jun. 2, 2000, e-pub. Mar. 22, 2000). "The Periplasmic *Escherichia coli* Peptidylprolyl cis,trans-Isomerase FkpA," *J. Biol. Chem.* 275(22):17100-17105.

(Continued)

*Primary Examiner* — Albert M Navarro
(74) *Attorney, Agent, or Firm* — Morrison & Foerster LLP

(57) ABSTRACT

The present invention provides methods for producing disulfide oxidoreductase A (DsbA) and disulfide oxidoreductase C (DsbC) polypeptides at very high levels of purity. Also provided are ultrapure DsbA and DsbC and methods of using same, e.g., for use in immunoassays to show removal of DsbA and DsbC from biologics produced in bacteria.

46 Claims, 17 Drawing Sheets

Specification includes a Sequence Listing.

(56) References Cited

FOREIGN PATENT DOCUMENTS

| | | |
|---|---|---|
| WO | WO-1993/16185 A3 | 8/1993 |
| WO | WO-1994/04690 A1 | 3/1994 |
| WO | WO-1996/14422 A1 | 5/1996 |
| WO | WO-1998/18946 A1 | 5/1998 |
| WO | WO-2000/29004 A1 | 5/2000 |
| WO | WO-2002/051870 A2 | 7/2002 |
| WO | WO-2002/051870 A3 | 7/2002 |
| WO | WO-2002/061090 A2 | 8/2002 |
| WO | WO-2002/061090 A3 | 8/2002 |
| WO | WO-2003/035694 A2 | 5/2003 |
| WO | WO-2003/035694 A3 | 5/2003 |
| WO | WO-2005/035572 A2 | 4/2005 |
| WO | WO-2005/035572 A3 | 4/2005 |
| WO | WO-2005/063816 A2 | 7/2005 |
| WO | WO-2005/063816 A3 | 7/2005 |
| WO | WO-2009/089004 A1 | 7/2009 |
| WO | WO-2012/013930 A2 | 2/2012 |
| WO | WO-2012/013930 A3 | 2/2012 |
| WO | WO-2016/144824 A1 | 9/2016 |

OTHER PUBLICATIONS

Brennan, M. et al. (Jul. 5, 1985). "Preparation of Bispecific Antibodies by Chemical Recombination of Monclonal Immunoglobulin $G_1$ Fragments," *Science* 229(4708):81-83.

Brodeur et al., Monoclonal Antibody Production Techniques and Applications pp. 51-63 (Marcel Dekker, Inc., New York, 1987).

Brown, D.M. et al (Jan. 1, 1989)"Anion-Cation Separations on a Mixed Bed Alumina-Silica Column," *Journal of Chromatography* 466:291-300.

Burton, D.R. (1985). "Immunoglobulin G: Functional Sites," *Molec. Immunol.* 22(3):161-206.

Capel, P.J.A et al.(1994). "Heterogeneity of Human IgG Fc Receptors," *Immunomethods* 4:25-34.

Carter, P. et al. (Feb. 1992). "High Level *Escherichia coli* Expression and Production of a Bivalent Humanized Antibody Fragment," *Bio/Technology* 10:163-167.

Chen, J. et al. (Jul. 9, 1999). "Chaperone Activity of DsbC," *J. Bio. Chem.* 274(28):19601-19605.

Chothia, C. (1976). "The Nature of the Accessible and Buried Surface Proteins," *J. Mol. Biol.* 105:1-14.

Chothia, C. et al. (1987). "Canonical Structures for the Hypervariable Regions of Immunoglobulins," *J. Mol. Biol.* 196:901-917.

Clackson, T. et al. (Aug. 15, 1991). "Making Antibody Fragments Using Phage Display Libraries," *Nature* 352:624-628.

Clynes, R. et al. (Jan. 1998). "Fc Receptors are Required in Passive and Active Immunity to Melanoma," Proc. Natl. Acad. Sci. (USA) 95:652-656.

Cunningham et al. (Jun. 2, 1989). "High-Resolution Epitope Mapping of hGH-Receptor Interactions by Alanine-Scanning Mutagenesis," *Science* 244:1081-1085.

Daëron, M. (1997). "Fc Receptor Biology," *Annu. Rev. Immunol.* 15:203-234.

David et al. (1974), "Protein Iodination With Solid State Lactoperoxidase," *Biochemistry*, 13(5):1014-1021.

Davies, J. et al. (Feb. 1994). "'Camelising' Human Antibody Fragments: NMR Studies on VH Domains," *FEBS Lett.* 339(3):285-290.

De Haas, M. et al. (1995). "Review Articles. Fcγ Receptors of Phagocytes," *J. Lab. Clin. Med.* 126:330-341.

Dooley, H. et al. (2006, e-pub. Jul. 22, 2005). "Antibody Repertoire Development in Cartilaginous Fish," *Developmental & Comparative Immunology* 30(1-2):43-56.

Ellman et al. (1991). "Biosynthetic Method Fpr Introducing Unnatural Amino Acids Site-Specifically Into Proteins," *Meth. Enzym.* 202:301-336.

Gazzano-Santoro, H. et al. (1997). "A Non-Radioactive Complement-Dependent Cytotoxicity Assay for Anti-CD20 Monoclonal Antibody," *J. Immunol. Methods* 202:163-171.

Goding, J.W. (1986). "Production of Monoclonal Antibodies," Chapter 3 in *Monoclonal Antibodies: Principles and Practice*, Academic Press, pp. 56-103.

Gruber, M. et al. (1994). "Efficient Tumor Cell Lysis Mediated by a Bispecific Single Chain Antibody Expressed in *Escherichia coli*," *J. Immunol.* 152:5368-5374.

Guyer, R.L. et al. (Aug. 1976). "Immunoglobulin Binding by Mouse Intestinal Epithelial Cell Receptors," *J. Immunol.* 117(2):587-593.

Hara et al. "Overproduction of Penicillin-Binding Protein 7 Suppress Thermosensitive Growth Defect at Low Osmolarity Due to an spr Mutation of *Escherichia coli*," *Microbial Drug Resistance*, 2:63-72 (1996).

Holliger, P. et al (Jul. 1993). ""Diabodies": Small bivalent and bispecific antibody fragments," *Proc. Natl. Acad. Sci. USA*, 90:6444-6448.

Holt, L.J. et al. (Nov. 2003). "Domain antibodies: proteins for therapy," *Trends Biotechnol.* 21(11):484-490.

Hunter et al. (1962). "Preparation of Iodine-I3I Labelled Human Growth Hormone of High Specific Activity," *Nature* 194:495-496.

Joly, JC et al. (Apr. 1994). "Protein Folding Activities of *Escherichia coli* Protein Disulfide Isomerase," *Biochem.* 33(14):4231-4236.

Joly, JC et al. (1997). "In Vitro and in Vivo Redox States of the *Escherichia coli* Periplasmic Oxidoreductases DsbA and DsbC," *Biochem.* 36:10067-10072.

Joly et al. (Mar. 1998). "Overexpression of *Escherichia coli* Oxidoreductases Increases Recombinant Insulin-Like Growth Factor-I Accumulation," 95:2773-2777.

Jones, P.T et al. (May 29, 1986). "Replacing the Complementarity Determining Regions in a Human Antibody With Those From a Mouse," *Nature* 321:522-525.

Kabat, E.A. et al. (1991). pp. 688-696 in *Sequences of Proteins of Immunological Interest*, 5th ed., 1:688-696.

Kim, J-Y et al. (1994). "Localization of the Site of the Murine IgGI Molecule That is Involved in Binding to the Murine Intestinal Fc Receptor," *Eur. J. Immunol.* 24:2429-2434.

Kindt, T.J. et al (2007). "Antigen and Antibodies," Chapter 4 in *Kuby Immunology*, 6th ed., W.H. Freeman and Co., p. 91.

Kohda, J. et al. (2002). "Effect of Oxidized and Reduced Forms of *Escherichia coli* DsbC on Protein Refolding," *Journal of Bioscience and Bioengineering* 94(2):130-134.

Köhler, G. et al. (Aug. 7, 1975). "Continuous Cultures of Fused Cells Secreting Antibody of Predefined Specificity," *Nature* 256:495-497.

Kontermann, R.E. (2005). "Recombinant Bispecific Antibodies for Cancer Therapy," *Acta Pharmacol. Sin.* 26(1):1-9.

Kostelny et al. (Mar. 1, 1992). "Formation of a Bispecific Antibody by the Use of Leucine Zippers," *J. Immunol.* 148(5):1547-1553.

Kozbor et al. (Dec. 1984). "A Human Hybrid Myeloma for Production of Human Monoclonal Antibodies," *J. Immunol.* 133(6):3001-3005.

Kurz, M. et al. (Jun. 1, 2008). "Cloning, Expression, Purification and Characterization of a Dsba-Like Protein Like Protein From *Wolbachia pipientis*," *Protein Expression and Purification* 59(2):266-273.

Lehninger, A.L. (1975). "The Amino Acid Building Blocks of Proteins," in *Biochemistry $2^{nd}$ ed.*, Worth Publishers, New York, pp. 73-75.

Lindmark, R. et al. (1983). "Binding of Immunoglobulins to Protein A and Immunoglobulin Levels in Mammalian Sera," *J. Immunol. Meth.* 62:1-13.

Luo, M. et al. (Feb. 28, 2013). "Optimization of DsbA Purification from Recombinant *Escherichia coli* Broth Using Box-Behnken Design Methodology," *Chinese Journal of Chemical Engineering* 21(2):185-191.

Marks, J.D. et al. (Dec. 5, 1991). "By-Passing Immunization. Human Antibodies From V-Gene Libraries Displayed on Phage," *J. Mol. Biol.* 222(3): 581-597.

Marks et al. (Jul. 1992). "By-Passing Immunization: Building High Affinity Human Antibodies by Chain Shuffling," *Bio/Technology* 10:779-783.

Marvin et al. (Jun. 2005). "Recombinant Approaches to IgG-Like Bispecific Antibodies," *Acta Pharmacologica Sincia* 26(6):649-658.

(56) References Cited

OTHER PUBLICATIONS

McCafferty et al. (Dec. 6, 1990). "Phage Antibodies: Filamentous Phage Displaying Antibody Variable Domains," *Nature* 348:552-554.

Messens, J. et al. (Oct. 26, 2007). "The Oxidase Dsba Folds a Protein With a Nonconsecutive Disulfide," *The Journal of Biological Chemistry* 282(43):31302-31307.

Milstein, C. et al. (Oct. 6, 1983). "Hybrid Hybridomas and their Use in Immunohistochemistry," *Nature* 305:537-540.

Missiakas, D. et al. (Apr. 15, 1994). "The *Escherichia coli*, dsbC (xprA) Gene Encodes a Periplasmic, Protein Involved in Disulfide Bond, Formation," *The EMBO Journal* 13(8):2013-2020.

Morimoto, K. et al. (1992). "Single-Step Purification of F(ab')$_2$ fragments of Mouse Monoclonal Antibodies (immunoglobulins G1) by Hydrophobic Interaction High Performance Liquid Chromatography Using TSKgel Phenyl-5PW," *J. Biochem. Biophys. Meth.* 24:107-117.

Morrison, S.L. et al. (Nov. 1984). "Chimeric Human Antibody Molecules: Mouse Antigen-Binding Domains With Human Constant Region Domains," *Proc. Natl. Acad. Sci. USA* 81:6851-6855.

Munson, P.J. et al. (1980). "LIGAND: A Versatile Computerized Approach for Characterization of Ligand-Binding Systems," *Anal. Biochem.* 107:220-239.

Muyldermans, S. et al. (Apr. 2001). "Recognition of Antigens by Single-Domain Antibody Fragments: The Superfluous Luxury of Paired Domains," *Trends Biochem. Sci.* 26(4):230-235.

Noren et al. (Apr. 14, 1989). "A General Method for Site-Specific Incorporatin of Unnatural Amino Acids Into Proteins," *Science* 244:182-188.

Nygren, H. (1982). "Conjugation of Horseradish Peroxidase to Fab Fragments With Different Homobifunctional and Heterobifunctional Cross-Linking Reagents," *J. Histochem. and Cytochem.* 30(5):407-412.

O'Sullivan et al. (1981). "Methods for the Preparation of Enzyme-Antibody Conjugates for Use in Enzyme Immunoassay," in *Methods in Enzymology*, ed. J.J. Langone and H. Van Vunakis, 73:147-166.

Pain et al. (1981). "Preparation of Protein A-Peroxidase Monoconjugate Using a Heterobifunctional Reagent, and Its Use in Enzyme Imunoassays," *J. Immunol. Methods* 40:219-230.

Plückthun, A. (1992). "Mono- and Bivalent Antibody Fragments Produced in *Escherichia coli*: Engineering, Folding and Antigen Binding," *Immunol. Revs.* 130:151-188.

Plückthun, A. (1994). "Antibodies From *Escherichia coli*," Chapter 11 in *The Pharmacology of Monoclonal Antibodies*, Rosenburg, M. (ed.) et al., Springer-Verlag, New York, 113:269-315.

Ponders, et al. (Feb. 20, 1987). "Tertiary Templates for Proteins. Use of Packing Criteria in the Enumeration of Allowed Sequences for Different Structural Classes," *J. Mol. Biol.* 193:775-791.

Portolano, S. et al. (Feb. 1, 1993). "Lack of Promiscuity in Autoantigen-Specific H and L Chain Combinations as Revealed by Human H and L Chain "Roulette"," *J. Immunol.* 150:880-887.

Presta, L.G. (1992). "Antibody Engineering," *Curr. Op. Struct. Biol.* 2:593-596.

Ramm, K. et al. (Jun. 2, 2000, e-pub. Mar. 22, 2000). The Periplasmic *Escherichia coli* Peptidylprolyl cis,trans-Isomerase FkpA *J. Biol. Chem.* 275:17106-17113.

Ravetch, J.V. et al. (1991). "Fc Receptors," *Annu. Rev. Immunol.* 9:457-492.

Riechmann, L. et al. (Mar. 24, 1988). "Reshaping Human Antibodies for Therapy," *Nature* 332:323-329.

Siebenlist et al. (Jun. 1980). "*E. coli* RNA Polymerase Interacts Homologously With Two Different Promoters," *Cell* 20:269-281.

Simmons et al. (2002). "Expression of Full-Length Immunoglobulins in *Escherichia coli*: Rapid and Efficient Production of Aglycosylated Antibodies," *J. Immunol. Methods* 263:133-147.

Skerra, A. (1993). "Bacterial Expression of Immunoglobulin Fragments," *Curr. Opinion in Immuno.* 5:256-262.

Suresh, M.R. et al. (1986). "Bispecific Monoclonal Antibodies From Hybrid Hybridomas," Chapter 17 *Methods in Enzymology* 121:210-228.

Traunecker, A. et al. (Dec. 1991). "Bispecific Single Chain Molecules (Janusins) Target Cytotoxic Lymphocytes on HIV Infected Cells," *EMBO J.* 10(12):3655-3659.

Tutt, A. et al. (Jul. 1, 1991). "Trispecific F(ab')$_3$ Derivatives that Use Cooperative Signaling via the TCR/CD3 Complex and CD2 to Activate and Redirect Resting Cytotoxic T Cells," *The Journal of Immunology* 147(1):60-69.

Urban, A. et al. (Jan. 1, 2001). "DsbA and DsbC Affect Extracellular Enzyme Formation in *Pseudomonas aeruginosa*," *Journal of Bacteriology* 183(2):587-596.

Ward, E.S. et al. (Oct. 12, 1989). "Binding Activities of a Repertoire of Single Immunoglobulin Variable Domains Secreted From *Escherichia coli*," *Nature* 341(6242):544-546.

Waterhouse et al. (1993). "Combinatorial Infection and in Vivo Recombination: A Strategy for Making Large Phage Antibody Repertories," *Nuc. Acids. Res.* 21(9):2265-2266.

Zamyatnin, A.A. (1972). "Protein Volume in Solution," *Prog. Biophys. Mol. Biol.* 24:107-123.

Zapata, G. et al. (1995). "Engineering Linear F(ab')$_2$ Fragments for Efficient Production in *Escherichia coli* and Enhanced Antiproliferative Activity," *Protein Eng.* 8(10):1057-1062.

Zapun, A. et al. (May 1, 1993). "The Reactive and Destabilizing Disulfide Bond of DsbA, a Protein Required for Protein Disulfide Bond Formation in Vivo," *Biochemistry* 32(19):5083-5092.

Zapun et al. "Structural and Functional Characterization of Dsbc, a Protein Involved in Disulfide Bond Formation in *Escherichia coli*," *Biochemistry* 34(15):5075-5089, (Jan. 1, 1995).

Zhan et al. "Genetic Analysis of Disulfide Isomerization in *Escherichia coli*: Expression of DsbC is Modulated by RNase E-Dependent mRNA Processing," *Journal of Bacteriology* 186(3):654-660, (Feb. 2004).

Zhang et al. "Generation of Monoclonal Antibodies Against *Escherichia coli* DsbA," *Hybridoma* 27(2):131-134, (Apr. 2008).

Zhu-Shimoni, J. et al. (Dec. 2014, e-pub. Sep. 10, 2014). "Host Cell Protein Testing by ELISAs and the Use of Orthogonal Methods," *Biotech and Bioeng.* 111:2367-2379.

International Search Report dated Jul. 1, 2016, for PCT Application No. PCT/US2016/021059, filed on Mar. 4, 2016, 9 pages.

Written Opinion dated Jul. 1, 2016, for PCT Application No. PCT/US2016/021059, filed on Mar. 4, 2016, 13 pages.

International Preliminary Report on Patentability dated Sep. 12, 2017, for PCT Application No. PCT/US2016/021059, filed on Mar. 4, 2016, 14 pages.

Burgess, R.R. et al. (2009). "Protein Precipitation Techniques," Chapter Twenty in Methods in Enzymology 463:331-342.

Huber, O. et al. (1999). "Recombinant Proteins," Chapter 13 in Protein Liquid Chromatography, M. Kastner, ed., Elsevier Science B.V., pp. 557-586.

Extended Search Report dated Mar. 16, 2020, for European Patent Application No. 19195777.8, 15 pages.

Ferreira, G.N.M. et al. (Sep. 1, 2000). "Downstream Processing of Plasmid DNA for Gene Therapy and DNA Vaccine Applications," Trends in Biotechnology 18:380-388.

Leuthardt, A. et al. (Jul. 1, 1993). "Cloning, Expression and Purification of a Recombinant Poly-Histidine-Linked-HIV-1 Protease," Febs Letters 326(1-3)275-280.

North, R.A. et al. (May 1, 2014). "Cloning, Expression, Purification, Crystallization and Preliminary X-ray Diffraction Analysis of N-Acetylmannosamine Kinase From Methicillin-Resistant *Staphylococcus aureus*," Acta Cryst. 70 (5):643-649.

Shimp, R.L. et al. (Nov. 1, 2006). "Production and Characterization of Clinical Grade *Escherichia coli* Derived Plasmodium Falciparum 42kDa Merozoite Surface Protein 1 (MSPI42) in the Absence of an Affinity Tag," Protein Expression and Purification 50(1):58-67.

\* cited by examiner

1. DsbA
2. DsbC
3. DsbA Centrate
4. Q Pool 010507
5. Q Pool Mock Pool Fr 10-15 010507
6. Q Pool Fr 8 (20 min peak)
7. Poros Fr 8
8. Poros Fr 13
9. Poros Fr 14
10. Poros Fr 15
11. Poros Main Elution Peak 11-15 (Mock Pool)

probe: anti DsbC-HRP

SDS PAGE: Coomassie Blue stained shows non-product (DsbC) related impurities

1. MWT. Ladder
2. DEAE load
3. DEAE Peak 1
4. DEAE Peak 3
5. DsbC standard

SEQUENCE LISTING

<160> NUMBER OF SEQ ID NOS: 6

<210> SEQ ID NO 1
<211> LENGTH: 189
<212> TYPE: PRT
<213> ORGANISM: E. coli

<400> SEQUENCE: 1

```
Ala Gln Tyr Glu Asp Gly Lys Gln Tyr Thr Thr Leu Glu Lys Pro Val
1               5                   10                  15

Ala Gly Ala Pro Gln Val Leu Glu Phe Phe Ser Phe Phe Cys Pro His
            20                  25                  30

Cys Tyr Gln Phe Glu Glu Val Leu His Ile Ser Asp Asn Val Lys Lys
        35                  40                  45

Lys Leu Pro Glu Gly Val Lys Met Thr Lys Tyr His Val Asn Phe Met
    50                  55                  60

Gly Gly Asp Leu Gly Lys Asp Leu Thr Gln Ala Trp Ala Val Ala Met
```

```
                65                  70                  75                  80
Ala Leu Gly Val Glu Asp Lys Val Thr Val Pro Leu Phe Glu Gly Val
                        85                  90                  95

Gln Lys Thr Gln Thr Ile Arg Ser Ala Ser Asp Ile Arg Asp Val Phe
            100                 105                 110

Ile Asn Ala Gly Ile Lys Gly Glu Glu Tyr Asp Ala Ala Trp Asn Ser
            115                 120                 125

Phe Val Val Lys Ser Leu Val Ala Gln Gln Glu Lys Ala Ala Ala Asp
        130                 135                 140

Val Gln Leu Arg Gly Val Pro Ala Met Phe Val Asn Gly Lys Tyr Gln
145                 150                 155                 160

Leu Asn Pro Gln Gly Met Asp Thr Ser Asn Met Asp Val Phe Val Gln
                    165                 170                 175

Gln Tyr Ala Asp Thr Val Lys Tyr Leu Ser Glu Lys Lys
                180                 185

<210> SEQ ID NO 2
<211> LENGTH: 627
<212> TYPE: DNA
<213> ORGANISM: E. coli

<400> SEQUENCE: 2
atgaaaaaga tttggctggc gctggctggt ttagttttag cgtttagcgc atcggcggcg      60
cagtatgaag atggtaaaca gtacactacc ctggaaaaac cggtagctgg cgcgccgcaa     120
gtgctggagt ttttctcttt cttctgcccg cactgctatc agtttgaaga agttctgcat     180
atttctgata atgtgaagaa aaaactgccg gaaggcgtga agatgactaa ataccacgtc     240
aacttcatgg gtggtgacct gggcaaagat ctgactcagg catgggctgt ggcgatggcg     300
ctgggcgtgg aagacaaagt gactgttccg ctgtttgaag cgtacagaa acccagacc      360 attcgttctg cttctgatat ccgcgatgta tttatcaacg caggtattaa aggtgaagag     420
tacgacgcgg cgtggaacag cttcgtggtg aaatctctgg tcgctcagca ggaaaaagct     480
gcagctgacg tgcaattgcg tggcgttccg gcgatgtttg ttaacggtaa atatcagctg     540
aatccgcagg gtatggatac cagcaatatg gatgtttttg ttcagcagta tgctgataca     600
gtgaaatatc tgtccgagaa aaaataa                                        627

<210> SEQ ID NO 3
<211> LENGTH: 216
<212> TYPE: PRT
<213> ORGANISM: E. coli

<400> SEQUENCE: 3

Asp Asp Ala Ala Ile Gln Gln Thr Leu Ala Lys Met Gly Ile Lys Ser
1               5                   10                  15

Ser Asp Ile Gln Pro Ala Pro Val Ala Gly Met Lys Thr Val Leu Thr
                20                  25                  30

Asn Ser Gly Val Leu Tyr Ile Thr Asp Asp Gly Lys His Ile Ile Gln
            35                  40                  45

Gly Pro Met Tyr Asp Val Ser Gly Thr Ala Pro Val Asn Val Thr Asn
        50                  55                  60

Lys Met Leu Leu Lys Gln Leu Asn Ala Leu Glu Lys Glu Met Ile Val
65                  70                  75                  80

Tyr Lys Ala Pro Gln Glu Lys His Val Ile Thr Val Phe Thr Asp Ile
                85                  90                  95
```

Thr Cys Gly Tyr Cys His Lys Leu His Glu Gln Met Ala Asp Tyr Asn
            100                 105                 110

Ala Leu Gly Ile Thr Val Arg Tyr Leu Ala Phe Pro Arg Gln Gly Leu
        115                 120                 125

Asp Ser Asp Ala Glu Lys Glu Met Lys Ala Ile Trp Cys Ala Lys Asp
    130                 135                 140

Lys Asn Lys Ala Phe Asp Asp Val Met Ala Gly Lys Ser Val Ala Pro
145                 150                 155                 160

Ala Ser Cys Asp Val Asp Ile Ala Asp His Tyr Ala Leu Gly Val Gln
                165                 170                 175

Leu Gly Val Ser Gly Thr Pro Ala Val Val Leu Ser Asn Gly Thr Leu
            180                 185                 190

Val Pro Gly Tyr Gln Pro Pro Lys Glu Met Lys Glu Phe Leu Asp Glu
        195                 200                 205

His Gln Lys Met Thr Ser Gly Lys
    210                 215

<210> SEQ ID NO 4
<211> LENGTH: 711
<212> TYPE: DNA
<213> ORGANISM: E. coli

<400> SEQUENCE: 4

```
atgaagaaag gttttatgtt gtttactttg ttagcggcgt tttcaggctt tgctcaggct      60
gatgacgcgg caattcaaca aacgttagcc aaaatgggca tcaaaagcag cgatattcag     120
cccgcgcctg tagctggcat gaagacagtt ctgactaaca gcggcgtgtt gtacatcacc     180
gatgatggta acatatcat tcaggggcca atgtatgacg ttagtggcac ggctccggtc     240
aatgtcacca ataagatgct gttaaagcag ttgaatgcgc ttgaaaaaga gatgatcgtt     300
tataaagcgc cgcaggaaaa acacgtcatc accgtgttta ctgatattac ctgtggttac     360
tgccacaaac tgcatgagca aatggcagac tacaacgcgc tggggatcac cgtgcgttat     420
cttgctttcc cgcgccaggg gctggacagc gatgcagaga agaaatgaa agctatctgg     480
tgtgcgaaag ataaaaacaa agcgtttgat gatgtgatgg caggtaaaag cgtcgcacca     540
gccagttgcg acgtggatat tgccgaccat tacgcacttg gcgtccagct ggcgttagc     600
ggtactccgg cagttgtgct gagcaatggc acacttgttc cgggttacca gccgccgaaa     660
gagatgaaag aattcctcga cgaacaccaa aaaatgacca gcggtaaata a              711
```

<210> SEQ ID NO 5
<211> LENGTH: 208
<212> TYPE: PRT
<213> ORGANISM: E. coli

<400> SEQUENCE: 5

Met Lys Lys Ile Trp Leu Ala Leu Ala Gly Leu Val Leu Ala Phe Ser
1               5                   10                  15

Ala Ser Ala Ala Gln Tyr Glu Asp Gly Lys Gln Tyr Thr Thr Leu Glu
            20                  25                  30

Lys Pro Val Ala Gly Ala Pro Gln Val Leu Glu Phe Phe Ser Phe Phe
        35                  40                  45

Cys Pro His Cys Tyr Gln Phe Glu Glu Val Leu His Ile Ser Asp Asn
    50                  55                  60

Val Lys Lys Lys Leu Pro Glu Gly Val Lys Met Thr Lys Tyr His Val
65                  70                  75                  80

```
Asn Phe Met Gly Gly Asp Leu Gly Lys Asp Leu Thr Gln Ala Trp Ala
                85                  90                  95

Val Ala Met Ala Leu Gly Val Glu Asp Lys Val Thr Val Pro Leu Phe
            100                 105                 110

Glu Gly Val Gln Lys Thr Gln Thr Ile Arg Ser Ala Ser Asp Ile Arg
            115                 120                 125

Asp Val Phe Ile Asn Ala Gly Ile Lys Gly Glu Glu Tyr Asp Ala Ala
130                 135                 140

Trp Asn Ser Phe Val Val Lys Ser Leu Val Ala Gln Gln Glu Lys Ala
145                 150                 155                 160

Ala Ala Asp Val Gln Leu Arg Gly Val Pro Ala Met Phe Val Asn Gly
                165                 170                 175

Lys Tyr Gln Leu Asn Pro Gln Gly Met Asp Thr Ser Asn Met Asp Val
            180                 185                 190

Phe Val Gln Gln Tyr Ala Asp Thr Val Lys Tyr Leu Ser Glu Lys Lys
            195                 200                 205

<210> SEQ ID NO 6
<211> LENGTH: 236
<212> TYPE: PRT
<213> ORGANISM: E. coli

<400> SEQUENCE: 6

Met Lys Lys Gly Phe Met Leu Phe Thr Leu Leu Ala Ala Phe Ser Gly
1               5                   10                  15

Phe Ala Gln Ala Asp Asp Ala Ile Gln Gln Thr Leu Ala Lys Met
            20                  25                  30

Gly Ile Lys Ser Ser Asp Ile Gln Pro Ala Pro Val Ala Gly Met Lys
            35                  40                  45

Thr Val Leu Thr Asn Ser Gly Val Leu Tyr Ile Thr Asp Asp Gly Lys
            50                  55                  60

His Ile Ile Gln Gly Pro Met Tyr Asp Val Ser Gly Thr Ala Pro Val
65                  70                  75                  80

Asn Val Thr Asn Lys Met Leu Leu Lys Gln Leu Asn Ala Leu Glu Lys
                85                  90                  95

Glu Met Ile Val Tyr Lys Ala Pro Gln Glu Lys His Val Ile Thr Val
            100                 105                 110

Phe Thr Asp Ile Thr Cys Gly Tyr Cys His Lys Leu His Glu Gln Met
            115                 120                 125

Ala Asp Tyr Asn Ala Leu Gly Ile Thr Val Arg Tyr Leu Ala Phe Pro
130                 135                 140

Arg Gln Gly Leu Asp Ser Asp Ala Glu Lys Glu Met Lys Ala Ile Trp
145                 150                 155                 160

Cys Ala Lys Asp Lys Asn Lys Ala Phe Asp Asp Val Met Ala Gly Lys
                165                 170                 175

Ser Val Ala Pro Ala Ser Cys Asp Val Asp Ile Ala Asp His Tyr Ala
            180                 185                 190

Leu Gly Val Gln Leu Gly Val Ser Gly Thr Pro Ala Val Val Leu Ser
            195                 200                 205

Asn Gly Thr Leu Val Pro Gly Tyr Gln Pro Pro Lys Glu Met Lys Glu
210                 215                 220

Phe Leu Asp Glu His Gln Lys Met Thr Ser Gly Lys
225                 230                 235
```

ULTRAPURIFIED DSBA AND DSBC AND METHODS OF MAKING AND USING THE SAME

CROSS-REFERENCE TO RELATED APPLICATIONS

This application is a divisional of U.S. application Ser. No. 15/061,943, filed Mar. 4, 2016, now U.S. Pat. No. 10,073,098, issued Sep. 11, 2018, which claims priority to and the benefit of U.S. Provisional Patent Application No. 62/129,701, filed Mar. 6, 2015, the disclosures of which are hereby incorporated by reference in their entireties and for all purposes.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 146392026010SEQLIST.TXT, date recorded: Jul. 24, 2018, size: 10 KB).

FIELD OF THE INVENTION

The present invention provides methods for producing disulfide oxidoreductase A (DsbA) and disulfide oxidoreductase C (DsbC) polypeptides at very high levels of purity. Also provided are ultrapure DsbA and DsbC and methods of using same, e.g., for use in immunoassays to show removal of DsbA and DsbC from biologics produced in bacteria.

BACKGROUND OF THE INVENTION

The production yield and quality of eukaryotic polypeptides produced in bulk by expression in bacterial host cells under fermentation conditions is often modified to improve the proper assembly and folding of the secreted heteromultimeric proteins (e.g., antibodies). Overexpression of chaperone proteins, such as Disulfide oxidoreducatase (Dsb) proteins including DsbA and DsbC facilitates the proper folding and solubility of heterologous proteins, such as antibodies, produced in bacterial host cells. DsbA is a strong thiol oxidant and the intermediate donor of disulfide bonds to secreted proteins. DsbC catalyzes the isomerization of disulfide bonds and can shuffle misfolded disulfide bonds. Dsb proteins are a primary catalyst of disulfide bond formation and isomerization in bacteria and promote the correct protein folding of protein. Chen et al. (1999) *J Bio Chem* 274:19601-19605; Georgiou et al., U.S. Pat. No. 6,083,715; Georgiou et al., U.S. Pat. No. 6,027,888; Bothmann and Pluckthun (2000) *J. Biol. Chem.* 275:17100-17105; Ramm and Pluckthun (2000) *J. Biol. Chem.* 275:17106-17113; Arie et al. (2001) *Mol. Microbiol.* 39:199-210.

For recombinant biopharmaceutical proteins to be acceptable for administration to human patients, it is important that residual impurities resulting from the manufacture and purification process are removed from the final biological product. These process components include culture medium proteins, immunoglobulin affinity ligands, viruses, endotoxin, DNA, and host cell proteins. These host cell impurities include process-specific host cell proteins (HCPs), which are process-related impurities in the biologic product derived from recombinant DNA technology, for example, DsbA and DsbC chaperones that are overexpressed to facilitate protein folding. While HCPs are typically present in the final drug substance in small quantities (in parts-per-million or nanograms per milligram of the intended recombinant polypeptide), it is recognized that HCPs are undesirable and their quantities should be minimized. For example, the U.S. Food and Drug Administration (FDA) requires that biopharmaceuticals intended for in vivo human use should be as free as possible of extraneous impurities, and requires tests for detection and quantitation of potential impurities, such as HCPs. In addition, the International Conference on Harmonization (ICH) provides guidelines on test procedures and acceptance criteria for biotechnological/biological products. The guidelines suggest that for HCPs, a sensitive immunoassay capable of detecting a wide range of protein impurities be utilized. Assays and reagents to detect immunoglobulins, DNA, endotoxins, viruses, and total HCPs, e.g., total *E. coli* proteins (ECP) have been developed but such assays and reagents to not accurately detect accessory proteins such as DsbA or DsbC. There are currently no commercial reagents or analytical methods of sufficient specificity and sensitivity for the detection and quantification of proteins such as DsbA or DsbC that are typically not expressed at high levels in bacteria but may be overexpressed in recombinant bacterial host cells to facilitate folding and secretion of biologic products.

Reagents, methods and kits for the detection of DsbA and DsbC are particularly needed where there are no existing assays and reagents of sufficient consistency, sensitivity, specificity or efficiency. The invention described herein meets certain of the above-described needs and provides other benefits.

All references cited herein, including patent applications and publications, are incorporated by reference in their entirety.

BRIEF SUMMARY

In some aspects, the invention provides methods for purifying a DsbA polypeptide from a cell lysate comprising the DsbA polypeptide, comprising a) adding polyethyleneimine (PEI) to a final concentration of about 0.01% to about 1.0% to a cell lysate comprising the DsbA polypeptide, b) clarifying the cell lysate by centrifugation, c) applying the clarified cell lysate comprising the DsbA polypeptide to an anion exchange chromatography material, d) eluting the DsbA polypeptide from the anion exchange chromatography material to generate an anion exchange eluate comprising the DsbA polypeptide, e) applying the anion exchange eluate comprising the DsbA polypeptide to a cation exchange chromatography material, f) eluting the DsbA polypeptide from the cation exchange chromatography material to generate a cation exchange eluate comprising the purified DsbA polypeptide. In some embodiments, the cell lysate comprising the DsbA polypeptide is held in the PEI for at least about 16 hours prior to anion exchange chromatography. In some embodiments, the final concentration of PEI in the lysate is about 0.1%. In some embodiments, the lysate comprising the DsbA polypeptide and the PEI is at a pH of about 7.0.

In some embodiments of the above embodiments, the anion exchange chromatography material is a strong anion exchanger. In some embodiments, the strong anion exchanger comprises a quarternary amine. In further embodiments, the quarternary amine is linked to crosslinked agarose. In some embodiments, the anion exchanger is QSFF anion exchanger.

In some embodiments of the above embodiments, the DsbA is eluted from the anion chromatography material using a salt gradient. In further embodiments, the salt gradient is a step gradient. In some embodiments, the clarified lysate comprises 10 mM MOPS, pH 7.1.

In some embodiments or the above embodiments, the DsbA is eluted from the anion exchange chromatography material with the following steps: about 15% of about 25 mM Tris and about 250 mM NaCl at about pH 9.2 for about four column volumes, about 20% of about 25 mM Tris and about 250 mM NaCl at about pH 9.2 for about four column volumes, about 25% of about 25 mM Tris and about 250 mM NaCl at about pH 9.2 until DsbA elutes from the column.

In some embodiments of the above embodiments, the clarified lysate comprising the DsbA polypeptide of step b) is passed through a 0.22 μm filter prior to anion exchange chromatography. In some embodiments, the clarified lysate comprising the DsbA polypeptide of step b) is adjusted to pH about 9.0 prior to anion exchange chromatography.

In some embodiments, the anion exchange eluate is collected in fractions. In some embodiments, the fractions are about 0.3 to about 1.0 column volumes (CV). In some embodiments, the fractions are analyzed by size exclusion chromatography prior to cation exchange chromatography. In some embodiments, fractions comprising at least about 55% DsbA are selected for further purification.

In some embodiments of the above embodiments, the cation exchange material comprises a sulphopropyl moiety. In some embodiments, the sulfopropyl moiety is linked to a crosslinked poly(styrene-divinylbenzene) matrix. In some embodiments, the cation exchange media is POROS HS 50 or equivalent. In some embodiments, the anion exchange eluate of step d) is adjusted to pH about 5.0 prior to cation exchange chromatography.

In some embodiments, the DsbA is eluted from the cation chromatography material using a salt gradient. In some embodiments, the cation chromatography material is washed with 5 column volumes of 12.5 mM MES. In some embodiments, the salt gradient is a gradient from about 0% to about 60% 12.5 mM MES and 1 M NaCl over 15 column volumes. In some embodiments, the cation exchange eluate is collected in fractions. In some embodiments, the fractions are analyzed by size exclusion chromatography. In some embodiments, fractions comprising at least about 95% DsbA are pooled.

In some embodiments of any of the above embodiments, the DsbA polypeptide is an *Escherichia coli* DsbA polypeptide. In some embodiments, the DsbA polypeptide comprises the amino acid sequence of SEQ ID NO:1. In other embodiments, the amino acid sequence of the DsbA polypeptide at least about 80% identical to the amino acid sequence of SEQ ID NO:1. In some embodiments, the DsbA is expressed in cell. In some embodiments, the cell is a prokaryotic cell. In further embodiments, the cell is an *E. coli* cell. In some embodiments, the cell is engineered to express DsbA at levels greater than endogenous expression of DsbA. In some embodiments, the cell is lysed using a microfluidizer.

In some aspects, the invention provides a composition comprising a DsbA polypeptide purified by the method of any one of the above embodiments. In some aspects, the invention provides a composition comprising a purified DsbA polypeptide, where the composition comprises at least about 95% monomeric DsbA polypeptide. In some aspects, the invention provides a composition comprising a purified DsbA polypeptide, where the composition comprises at least about 98% monomeric DsbA polypeptide. In some embodiments, the composition comprises less that about 2% low molecular weight species. In some embodiments, the composition comprises less than about 1% high molecular weight species. In some embodiments, the percentage of monomeric DsbA polypeptide is detected by size exclusion chromatography. In some embodiments, the composition comprises less than about 5% impurities. In some embodiments, the impurities are high molecular weight and/or low molecular weight polypeptide species relative to native or desired DsbA. In some embodiments, the impurities are one or more of an *E. coli* protein (ECP), aggregates of DsbA, fragments of DsbA, a nucleic acid or a cell culture media component. In some embodiments, the DsbA is stable to one or more freeze-thaw cycles. In some embodiments, the DsbA is stable to one, two, three, four, five, six, seven, eight, nine, ten or greater than ten freeze-thaw cycles. In some embodiments, the ultrapure DsbA is used as a reference standard; for example, to determine the amount or concentration of DsbA in a test sample. In some embodiments, the ultrapure DsbA is used as a positive control; for example, in an assay to determine the presence and/or quantity of DsbA in a sample.

In some embodiments, the purity of the DsbA polypeptide in the composition is measured by chromatography, SDS polyacrylamide gel electrophoresis or western blot analysis. In some embodiments, the purity of the DsbA polypeptide in the composition is measured by high performance liquid chromatography (HPLC). In some embodiments, the chromatography is size exclusion chromatography (e.g., SEC-HPLC). In some embodiments, the purity of the DsbA polypeptide in the composition is measured by SDS gel electrophoresis using a fluorescent protein stain or a silver stain. In some embodiments, the presence of non-DsbA polypeptides in the composition are identified by the presence of species identified by gel electrophoresis that are not immunoreactive with anti-DsbA antibodies as shown by western blot analysis. In some embodiments, the presence of aggregates of the DsbA polypeptide in the composition are identified by the presence of species with a molecular weight greater than the native DsbA by western blot analysis. In some embodiments, the presence of fragments of the DsbA polypeptide in the composition are identified by the presence of species with a molecular weight less than the native DsbA by western blot analysis.

In some aspects, the invention provides methods for generating antibodies that specifically bind DsbA, comprising exposing an animal to the ultrapure DsbA, purified as described above. In further embodiments, the method comprises collecting sera from the animal wherein the sera comprises antibodies that specifically bind DsbA. In some embodiments, the sera comprises polyclonal antibodies that specifically bind DsbA. In some aspects, the invention provides one or more monoclonal antibodies are isolated from the sera. In some embodiments, the animal is a goat, a rabbit, a mouse, a guinea pig, a hamster, a rat, a donkey or a chicken.

In some aspects, the invention provides methods for purifying antibodies that specifically bind DsbA, comprising contacting a composition comprising anti-DsbA antibodies to chromatography material comprising ultrapure DsbA attached to a support material, washing the chromatography material to remove unbound compounds, and eluting the anti-DsbA antibodies. In some embodiments, the ultrapure DsbA comprises at least about 95% monomeric DsbA polypeptide. In some embodiments, the ultrapure DsbA comprises less than about 5% impurities, less than about 1% impurities, or less than about 0.1% impurities. In some embodiments, the ultrapure DsbA is prepared by any of the methods described herein. In some embodiments, the antibodies are polyclonal antibodies. In some embodiments, the antibodies are prepared according to any of the methods described herein. In some embodiments, less than 1% of the antibodies specifically bind non-DsbA compounds.

In some aspects, the invention provides compositions comprising polyclonal antibodies that specifically bind DsbA, wherein the polyclonal antibodies are generated by exposing an animal to any of the DsbA compositions described above. In some embodiments, the polyclonal antibodies are collected from the sera of the animal. In some embodiments, the invention provides compositions comprising monoclonal antibodies that specifically bind DsbA, wherein the monoclonal antibodies are generated by exposing an animal to any of the DsbA compositions described above. In some embodiments, the animal is a goat, a rabbit, a mouse, a guinea pig, a hamster, a rat, a donkey or a chicken.

In some embodiments, the invention provides a method for analyzing a recombinant polypeptide sample for the presence of and/or quantity of DsbA, comprising detecting DsbA in the sample using an immunoassay and comparing the amount of DsbA detected in the sample with the detection of one or more concentrations of an ultrapure DsbA reference standard. In some embodiments, a number of different concentrations of the reference standard DsbA are tested in order to establish a correlation between the level of detection and the concentration of DsbA in the reference standard. The concentration of DsbA in a test sample can be determined by comparing the level of detection of DsbA in the test sample with the detection of the known concentrations of DsbA in the reference standard. In some embodiments, the preparation comprises less than about any of 1% of impurities. In some embodiments, the ultrapure DsbA reference standard is prepared by the methods described herein. In some embodiments, the immunoassay comprises antibodies that specifically bind ultrapure DsbA. In some embodiments, the antibodies that specifically bind ultrapure DsbA bind less than about any of 1% non-DsbA compounds. In some embodiments, the antibodies that specifically bind ultrapure DsbA are polyclonal antibodies. In other embodiments, the antibodies that specifically bind ultrapure DsbA are monoclonal antibodies. In some embodiments, the antibodies that specifically bind ultrapure DsbA are used as capture antibodies in the immunoassay. In some embodiments, the antibodies that specifically bind ultrapure DsbA are used as detection antibodies. In some embodiments, the detection antibodies are conjugated to a detection agent (e.g., a horseradish peroxidase). In some embodiments, the DsbA is an *E. coli* DsbA. In some embodiments, the recombinant polypeptide is prepared in a host cell (e.g., an *E. coli* host cell). In some embodiments, the host cell overexpresses DsbA (e.g., an *E. coli* host cell that overexpressed DsbA). In some embodiments, the sample is cell lysate or is obtained from a recombinant polypeptide preparation and wherein the recombinant polypeptide preparation has been subjected to one or more chromatographic purification steps. In some embodiment, the recombinant polypeptide preparation is a final purified product.

In some aspects, the invention provides immunoassay methods for detecting DsbA in a sample, for example, wherein the sample is obtained from a recombinant polypeptide preparation or a host cell line, the method comprising: (a) contacting a capture antibody that binds DsbA with the sample thereby generating a sample-capture antibody combination material; (b) contacting a detection antibody that binds DsbA with the sample-capture antibody combination material; and (c) detecting the antibody bound to the sample-capture antibody combination material. In further embodiments, the method comprises quantifying the level of the detection antibody bound using a standard titration curve. In further embodiments, the method comprises calculating an amount of DsbA present in the sample based on the level of the detection antibody bound. In some embodiments, the amount of DsbA present in the sample is determined by comparing the standard titration curve with a standard titration curve generated with an ultrapure DsbA composition. In some embodiments, the ultrapure DsbA composition comprises at least about 95% monomeric DsbA polypeptide. In some embodiments, the ultrapure DsbA composition comprises less than about 5% impurities, less than about 1% impurities, or less than about 0.1% impurities. In some embodiments, the ultrapure DsbA in the composition is prepared by any of the methods described herein. In some embodiments, the capture antibody specifically binds ultrapure DsbA. In some embodiments, the detection antibody specifically binds ultrapure DsbA. In some embodiments, the antibody that specifically binds ultrapure DsbA is a polyclonal antibody. In some embodiments, the detection antibody that binds DsbA is conjugated to a horseradish peroxidase. In some embodiments, the immunoassay is a sandwich assay. In further embodiments, the sandwich assay is an enzyme-linked immunosorbent assay (ELISA). In some embodiments, the DsbA is an *E. coli* DsbA. In some embodiments, the recombinant polypeptide preparation or the host cell line is obtained from *E. coli*. In some embodiments, the host cell line overexpresses DsbA (e.g., an *E. coli* host cell that overexpresses DsbA). In some embodiments, the sample is cell lysate. In some embodiments, the sample is obtained from the recombinant polypeptide preparation and wherein the recombinant polypeptide preparation has been subjected to one or more chromatographic purification steps. In some embodiments, the recombinant polypeptide preparation is final purified product. In some embodiments, the recombinant polypeptide contained in the recombinant polypeptide preparation is an antibody or an immunoadhesin. In some embodiments, the antibody is a multispecific antibody, a bispecific antibody, a half antibody or an antibody fragment. In some embodiments, the recombinant polypeptide is an IgG1, an IgG2, an IgG3, or an IgG4.

In some embodiments, the invention provides a quality assay for a pharmaceutical composition comprising a recombinant polypeptide prepared from a bacterial cell, the release assay comprising subjecting the pharmaceutical composition to an immunoassay as described herein, wherein detection of DsbA in the immunoassay indicates that the pharmaceutical composition is not suitable for therapeutic administration to an animal. In some embodiments, an amount of DsbA in the pharmaceutical composition of less than about 1 ppm indicates that the pharmaceutical composition is suitable for administration to the animal. In some embodiments, the recombinant polypeptide is prepared from an *E. coli* cell. In some embodiments, the bacterial cell overexpresses DsbA. In some embodiments, the sample is cell lysate. In some embodiments, the sample is obtained from the recombinant polypeptide preparation and wherein the recombinant polypeptide preparation has been subjected to one or more chromatographic purification steps. In some embodiments, the recombinant polypeptide preparation is final purified product. In some embodiments, the recombinant polypeptide contained in the recombinant polypeptide preparation is an antibody or an immunoadhesin. In some embodiments, the antibody is a multispecific antibody, a bispecific antibody, a half antibody or an antibody fragment. In some embodiments, the recombinant polypeptide is an IgG1, an IgG2, an IgG3, or an IgG4.

In some aspects, the invention provides methods for purifying a DsbC polypeptide from a cell lysate comprising the DsbC polypeptide comprising a) adding polyethyleneimine (PEI) to a final concentration of about 0.01% to about 1.0% to a cell lysate comprising the DsbC polypeptide, b) clarifying the cell lysate by centrifugation, c) applying the clarified cell lysate comprising the DsbC polypeptide to an anion exchange chromatography material, d) eluting the DsbC polypeptide from the anion exchange chromatography material to generate an anion exchange eluate comprising the DsbC polypeptide, e) applying the anion exchange eluate comprising the DsbC polypeptide to a hydrophobic interaction chromatography (HIC) material, f) eluting the DsbC polypeptide from the HIC material to generate a HIC eluate, g) applying the HIC eluate comprising the DsbC polypeptide to a size exclusion chromatography, h) collecting fractions from the size exclusion chromatography comprising the purified DsbC polypeptide. In some embodiments, the cell lysate comprising the DsbC polypeptide is held in the PEI for at least about 16 hours prior to anion exchange chromatography. In some embodiments, the final concentration of PEI in the lysate is about 0.1%. In some embodiments, the lysate comprising the DsbC polypeptide and the PEI is at a pH of about 7.0.

In some embodiments of the above embodiment the anion exchange chromatography material is a weak anion exchanger. In yet further embodiments, the weak anion exchanger comprises a quarternary amine. In yet further embodiments, the quarternary amine is linked to crosslinked agarose.

In some embodiments, the DsbC is eluted from the cation chromatography material using a salt gradient. In further embodiments, the salt gradient is a linear gradient. In some embodiments, the anion exchange material is washed in 10 mM MOPS. In some embodiments, the salt gradient is a gradient from about 0% to about 60% 10 mM MOPS and 250 mM NaCl over 15 column volumes.

In some embodiments of the above embodiment, the clarified lysate comprising the DsbC polypeptide of step b) is passed through a 0.22 µm filter prior to anion exchange chromatography. In some embodiments, the clarified lysate comprising the DsbC polypeptide of step b) is adjusted to pH about 8.0 prior to anion exchange chromatography.

In some embodiments, the anion exchange eluate is collected in fractions. In some embodiments, the fractions are analyzed by size exclusion chromatography prior to hydrophobic interaction chromatography. In some embodiments, fractions comprising at least about 25% DsbC are selected for further purification.

In some embodiments of the above embodiment, the HIC material comprises a phenyl moiety. In further embodiments, the phenyl moiety is linked to a crosslinked agarose. In some embodiments, the anion exchange eluate is conditioned to contain about 0.54 M sodium sulfate and about 50 mM $PO_4$, about pH 7 before HIC chromatography. In some embodiments, the DsbC is eluted from the HIC material using water. In some embodiments, the HIC eluate is collected in fractions. In further embodiments, fractions comprising DsbC are pooled.

In some embodiments of the above embodiments, the size exclusion chromatography material comprises a spherical composite of cross-linked agarose and dextran. In some embodiments, the size exclusion flow through is collected in fractions. In some embodiments, the HIC eluate is ultrafiltered prior to size exclusion chromatography. In some embodiments, fractions comprising DsbC are pooled.

In some embodiments of the above embodiments, the DsbC polypeptide is an *Escherichia coli* DsbC polypeptide. In some embodiments, the DsbC polypeptide comprises the amino acid sequence of SEQ ID NO:3. In some embodiments, the amino acid sequence of the DsbC polypeptide at least about 80% identical to the amino acid sequence of SEQ ID NO:3.

In some embodiments of the above embodiments, the DsbC is expressed in cell. In some embodiments, the cell is a prokaryotic cell. In some embodiments, the cell is an *E. coli* cell. In some embodiments, the cell is engineered to express DsbC at levels greater than endogenous expression of DsbC. In some embodiments, the cell is lysed using a microfluidizer.

In some aspects, the invention provides a composition comprising a DsbC polypeptide purified by the method of any one of the above embodiments. In some aspects, the invention provides a composition comprising a purified DsbC polypeptide, where the composition comprises at least about 95% monomeric DsbC polypeptide. In some embodiments, the composition comprises at least about 98% monomeric DsbC polypeptide. In some embodiments, the composition comprises at least about 99% monomeric DsbC polypeptide. In some embodiments, the composition comprises at least about 99.5% monomeric DsbC polypeptide. In some embodiments, the composition comprises less that about 2% low molecular weight species. In some embodiments, the composition comprises less than about 1% high molecular weight species. In some embodiments, the percentage of monomeric DsbC polypeptide is detected by size exclusion chromatography. In some embodiments, the impurities are high molecular weight and/or low molecular weight polypeptide species relative to native or desired DsbC. In some embodiments, the impurities are one or more of an *E. coli* protein (ECP), aggregates of DsbC, fragments of DsbC, a nucleic acid or a cell culture media component. In some embodiments, the DsbC is stable to one or more freeze-thaw cycles. In some embodiments, the DsbC is stable to one, two, three, four, five, six, seven, eight, nine, ten or greater than ten freeze-thaw cycles. In some embodiments, the ultrapure DsbC is used as a reference standard; for example, to determine the amount or concentration of DsbC in a test sample. In some embodiments, the ultrapure DsbC is used as a positive control; for example, in an assay to determine the presence and/or quantity of DsbC in a sample.

In some embodiments, the purity of the DsbC polypeptide in the composition is measured by chromatography, SDS polyacrylamide gel electrophoresis or western blot analysis. In some embodiments, the purity of the DsbC polypeptide in the composition is measured by high performance liquid chromatography (HPLC). In some embodiments, the chromatography is size exclusion chromatography (e.g., SEC-HPLC). In some embodiments, the purity of the DsbC polypeptide in the composition is measured by SDS gel electrophoresis using a fluorescent protein stain or a silver stain. In some embodiments, the presence of non-DsbC polypeptides in the composition are identified by the presence of species identified by gel electrophoresis that are not immunoreactive with anti-DsbC antibodies as shown by western blot analysis. In some embodiments, the presence of aggregates of the DsbC polypeptide in the composition are identified by the presence of species with a molecular weight greater than the native DsbC by western blot analysis. In some embodiments, the presence of fragments of the DsbC polypeptide in the composition are identified by the presence of species with a molecular weight less than the native DsbC by western blot analysis.

In some aspects, the invention provides methods for generating antibodies that specifically bind DsbC, comprising exposing an animal to the ultrapure DsbC, purified as described above. In further embodiments, the method comprises collecting sera from the animal wherein the sera comprises antibodies that specifically bind DsbC. In some embodiments, the sera comprises polyclonal antibodies that specifically bind DsbC. In some aspects, the invention provides one or more monoclonal antibodies are isolated from the sera. In some embodiments, the animal is a goat, a rabbit, a mouse, a guinea pig, a hamster, a rat, a donkey or a chicken.

In some aspects, the invention provides methods for purifying antibodies that specifically bind DsbC, comprising contacting a composition comprising anti-DsbC antibodies to chromatography material comprising ultrapure DsbC attached to a support material, washing the chromatography material to remove unbound compounds, and eluting the anti-DsbC antibodies. In some embodiments, the ultrapure DsbC comprises more than about 95% monomeric DsbC polypeptide. In some embodiments, the ultrapure DsbC comprises less than about 5% impurities, less than about 1% impurities, or less than about 0.1% impurities. In some embodiments, the ultrapure DsbC is prepared by any of the methods described herein. In some embodiments, the antibodies are polyclonal antibodies. In some embodiments, the antibodies are prepared according to any of the methods described herein. In some embodiments, less than 1% of the antibodies specifically bind non-DsbC compounds.

In some aspects, the invention provides compositions comprising polyclonal antibodies that specifically bind DsbC, wherein the polyclonal antibodies are generated by exposing an animal to any of the DsbC compositions described above. In some embodiments, the polyclonal antibodies are collected from the sera of the animal. In some embodiments, the invention provides compositions comprising monoclonal antibodies that specifically bind DsbC, wherein the monoclonal antibodies are generated by exposing an animal to any of the DsbC compositions described above. In some embodiments, the animal is a goat, a rabbit, a mouse, a guinea pig, a hamster, a rat, a donkey or a chicken.

In some embodiments, the invention provides a method for analyzing a recombinant polypeptide sample for the presence of and/or quantity of DsbC, comprising detecting DsbC in the sample using an immunoassay and comparing the amount of DsbC detected in the sample with the detection of one or more concentrations of an ultrapure DsbC reference standard. In some embodiments, a number of different concentrations of the reference standard DsbC are tested in order to establish a correlation between the level of detection and the concentration of DsbC in the reference standard. The concentration of DsbC in a test sample can be determined by comparing the level of detection of DsbC in the test sample with the detection of the known concentrations of DsbC in the reference standard. In some embodiments, the preparation comprises less than about any of 1% of impurities. In some embodiments, the ultrapure DsbC reference standard is prepared by the methods described herein. In some embodiments, the immunoassay comprises antibodies that specifically bind ultrapure DsbC. In some embodiments, the antibodies that specifically bind ultrapure DsbC bind less than about any of 1% non-DsbC compounds.

In some embodiments, the antibodies that specifically bind ultrapure DsbC are polyclonal antibodies. In other embodiments, the antibodies that specifically bind ultrapure DsbC are monoclonal antibodies. In some embodiments, the antibodies that specifically bind ultrapure DsbC are used as capture antibodies in the immunoassay. In some embodiments, the antibodies that specifically bind ultrapure DsbC are used as detection antibodies. In some embodiments, the detection antibodies are conjugated to a detection agent (e.g., a horseradish peroxidase). In some embodiments, the DsbC is an E. coli DsbC. In some embodiments, the recombinant polypeptide is prepared in a host cell (e.g., an E. coli host cell). In some embodiments, the host cell overexpresses DsbC (e.g., an E. coli host cell that overexpressed DsbC). In some embodiments, the sample is cell lysate or is obtained from a recombinant polypeptide preparation and wherein the recombinant polypeptide preparation has been subjected to one or more chromatographic purification steps. In some embodiment, the recombinant polypeptide preparation is a final purified product.

In some aspects, the invention provides immunoassay methods for detecting DsbC in a sample, for example, wherein the sample is obtained from a recombinant polypeptide preparation or a host cell line, the method comprising: (a) contacting a capture antibody that binds DsbC with the sample thereby generating a sample-capture antibody combination material; (b) contacting a detection antibody that binds DsbC with the sample-capture antibody combination material; and (c) detecting the antibody bound to the sample-capture antibody combination material. In further embodiments, the method comprises quantifying the level of the detection antibody bound using a standard titration curve. In further embodiments, the method comprises calculating an amount of DsbC present in the sample based on the level of the detection antibody bound. In some embodiments, the amount of DsbC present in the sample is determined by comparing the standard titration curve with a standard titration curve generated with an ultrapure DsbC composition. In some embodiments, the ultrapure DsbC composition comprises at least about 95% monomeric DsbC polypeptide. In some embodiments, the ultrapure DsbC composition comprises less than about 5% impurities, less than about 1% impurities, or less than about 0.1% impurities. In some embodiments, the ultrapure DsbC in the composition is prepared by any of the methods described herein. In some embodiments, the capture antibody specifically binds ultrapure DsbC. In some embodiments, the detection antibody specifically binds ultrapure DsbC. In some embodiments, the antibody that specifically binds ultrapure DsbC is a polyclonal antibody. In some embodiments, the detection antibody that binds DsbC is conjugated to a horseradish peroxidase. In some embodiments, the immunoassay is a sandwich assay. In further embodiments, the sandwich assay is an enzyme-linked immunosorbent assay (ELISA). In some embodiments, the DsbC is an E. coli DsbC. In some embodiments, the recombinant polypeptide preparation or the host cell line is obtained from E. coli. In some embodiments, the host cell line overexpresses DsbC (e.g., an E. coli host cell that overexpresses DsbC). In some embodiments, the sample is cell lysate. In some embodiments, the sample is obtained from the recombinant polypeptide preparation and wherein the recombinant polypeptide preparation has been subjected to one or more chromatographic purification steps. In some embodiments, the recombinant polypeptide preparation is final purified product. In some embodiments, the recombinant polypeptide contained in the recombinant polypeptide preparation is an antibody or an immunoadhesin. In some embodiments, the antibody is a multispecific antibody, a bispecific antibody, a half antibody or an antibody fragment. In some embodiments, the recombinant polypeptide is an IgG1, an IgG2, an IgG3, or an IgG4.

In some embodiments, the invention provides a quality assay for a pharmaceutical composition comprising a recombinant polypeptide prepared from a bacterial cell, the release assay comprising subjecting the pharmaceutical composition to an immunoassay as described herein, wherein detection of DsbC in the immunoassay indicates that the pharmaceutical composition is not suitable for therapeutic administration to an animal. In some embodiments, an amount of DsbC in the pharmaceutical composition of less than about 1 ppm indicates that the pharmaceutical composition is suitable for administration to the animal. In some embodiments, the recombinant polypeptide is prepared from an E. coli cell. In some embodiments, the bacterial cell overexpresses DsbC. In some embodiments, the sample is cell lysate. In some embodiments, the sample is obtained from the recombinant polypeptide preparation and wherein the recombinant polypeptide preparation has been subjected to one or more chromatographic purification steps. In some embodiments, the recombinant polypeptide preparation is final purified product. In some embodiments, the recombinant polypeptide contained in the recombinant polypeptide preparation is an antibody or an immunoadhesin. In some embodiments, the antibody is a multispecific antibody, a bispecific antibody, a half antibody or an antibody fragment. In some embodiments, the recombinant polypeptide is an IgG1, an IgG2, an IgG3, or an IgG4.

In some aspects, the invention provides kits for the detection of DsbA in a pharmaceutical composition comprising a recombinant polypeptide prepared from a bacterial cell, said kit comprising anti-DsbA antibodies prepared by any of the methods described herein or a composition of any of the anti-DsbA antibodies described herein.

In some aspects, the invention provides kits for the detection of DsbC in a pharmaceutical composition comprising a recombinant polypeptide prepared from a bacterial cell, said kit comprising anti-DsbC antibodies prepared by any of the methods described herein or a composition of any of the anti-DsbC antibodies described herein.

In some aspects, the invention provides kits for the detection of DsbA and DsbC in a pharmaceutical composition comprising a recombinant polypeptide prepared from a bacterial cell, said kit comprising anti-DsbA antibodies and anti-DsbC antibodies prepared by any of the methods described herein or a composition of any of the anti-DsbA antibodies and any of the anti-DsbC antibodies described herein. In some embodiments, the kits further comprise ultrapure DsbA and/or DsbC for use as a reference standard in generating standard curves for quantitating DsbA and/or DsbC in a sample. In some embodiments, the kits further comprise ultrapure DsbA and/or DsbC for use as positive controls in an assay to detect DsbA and/or DsbC in a sample.

BRIEF DESCRIPTION OF THE DRAWINGS

FIG. 8A is a western blot using anti-DsbC-HRP as the detecting agent. FIG. 8B is an SDS PAGE of factions, stained with Coomassie Blue.

DETAILED DESCRIPTION OF THE INVENTION

Figure 1:
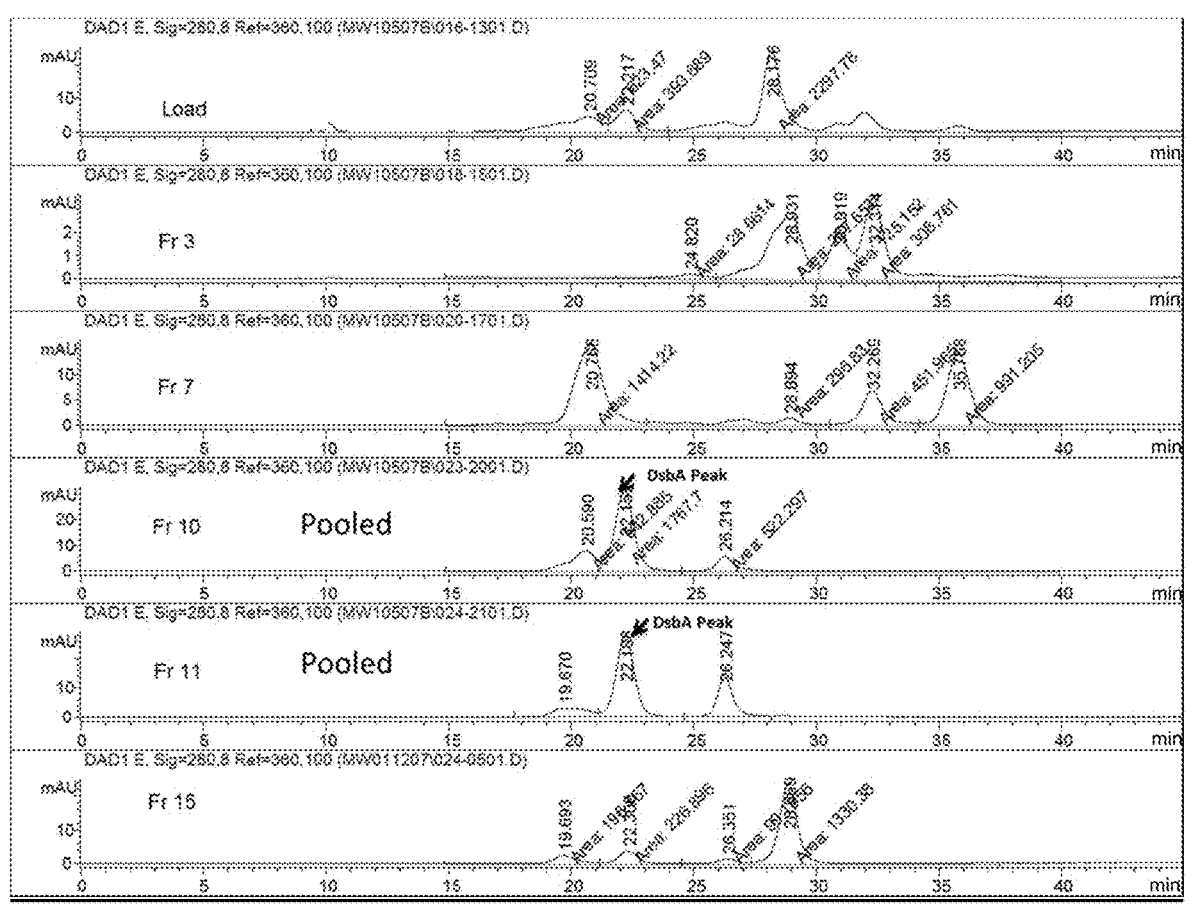
FIG. 1 shows chromatograms showing size exclusion chromatography of QSFF fractions for purification of DsbA. From top to bottom, the chromatograms represent the following fractions: load, fraction 3, fraction 7, fraction 10, fraction 11 and fraction 15.

The invention provides methods to generate ultrapure compositions of DsbA and DsbC. Such compositions are used to generate antibodies that are highly specific to DsbA or DsbC. The antibodies in turn are useful for the detection of DsbA and DsbC in recombinant polypeptides prepared in bacterial fermentation cultures where DsbA and DsbC are overexpressed to facilitate recombinant polypeptide folding and assembly. For example, the antibodies may be useful in release assays in the development of pharmaceutical formulation of the recombinant polypeptides such as antibodies.

I. Definitions

The term "detecting" is used herein in the broadest sense to include both qualitative and quantitative measurements of a target molecule. Detecting includes identifying the mere presence of the target molecule in a sample as well as determining whether the target molecule is present in the sample at detectable levels.

The terms "polypeptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. The terms "polypeptide" and "protein" as used herein specifically encompass antibodies.

"Purified" polypeptide (e.g., antibody or immunoadhesin) means that the polypeptide has been increased in purity, such that it exists in a form that is more pure than it exists in its natural environment and/or when initially synthesized and/or amplified under laboratory conditions. Purity is a relative term and does not necessarily mean absolute purity.

As used herein, "ultrapure DsbA" and "ultrapure DsbC" refer to DsbA or DsbC compositions in which at least about 95% of the protein in the composition is the desired protein, monomeric DsbA or monomeric DsbC. In some examples, ultrapure DsbA and ultrapure DsbC comprises at least about 96%, 97%, 98%, 99%, or 99.5% monomeric DsbA or monomeric DsbC. In some embodiments, monomeric DsbA or monomeric DsbC is determined by SEC.

When used in reference to a polypeptide, "Dsb" proteins refer to bacterial disulfide oxidoreductases. Bacterial disulfide oxireductases are members of the disulfide bond family of enzymes. Members of the Dsb family include DsbA, DsbB, DsbC, DsbD and DsbG. DsbA forms intrachain disulfide bonds as peptides emerge into the cell's periplasm and DsbC serves as a disulfide bond isomerase during oxidative protein-folding in cell's periplasm.

As used herein, "DsbA" may also be known as periplasmic protein disulfide isomerase I. An exemplary DsbA protein is E. coli DsbA. The amino acid sequence of E. coli DsbA is provided by NCBI Accession No. NP_418297 (SEQ ID NO:1) and the nucleic acid sequence of E. coli dsbA gene is provided by NCBI Accession No. NC_000913.3 or EcoGene:EG11297 (SEQ ID NO:2).

As used herein, "DsbC" may also be known as periplasmic protein disulfide isomerase II. An exemplary DsbC protein is E. coli DsbC. The amino acid sequence of E. coli DsbC is provided by NCBI Accession No. NP_417369.1 (SEQ ID NO:3) and the nucleic acid sequence of E. coli dsbC gene is provided by NCBI Accession No. NC_000913.3 or EcoGene:EG11070 (SEQ ID NO:4).

A "sample" refers to a small portion of a larger quantity of material. Generally, testing according to the methods described herein is performed on a sample. The sample is typically obtained from a recombinant polypeptide preparation obtained, for example, from cultured recombinant polypeptide-expressing cell lines, also referred to herein as "product cell lines," or from cultured host cells. As used herein, "host cells" do not contain genes for the expression of recombinant polypeptides of interest or products. A sample may be obtained from, for example but not limited to, harvested cell culture fluid, from an in-process pool at a certain step in a purification process, or from the final purified product.

A "capture antibody" refers to an antibody that specifically binds a target molecule in a sample. Under certain conditions, the capture antibody forms a complex with the target molecule such that the antibody-target molecule complex can be separated from the rest of the sample. In certain embodiments, such separation may include washing away substances or material in the sample that did not bind the capture antibody. In certain embodiments, a capture antibody may be attached to a solid support surface, such as, for example but not limited to, a plate or a bead.

A "detection antibody" refers to an antibody that specifically binds a target molecule in a sample or in a sample-capture antibody combination material. Under certain conditions, the detection antibody forms a complex with the target molecule or with a target molecule-capture antibody complex. A detection antibody is capable of being detected either directly through a label, which may be amplified, or indirectly, e.g., through use of another antibody that is labeled and that binds the detection antibody. For direct labeling, the detection antibody is typically conjugated to a moiety that is detectable by some means, for example, including but not limited to, biotin or ruthenium.

The terms "label" or "detectable label" refers to any chemical group or moiety that can be linked to a substance that is to be detected or quantitated, e.g., an antibody. Typically, a label is a detectable label that is suitable for the sensitive detection or quantification of a substance. Examples of detectable labels include, but are not limited to, luminescent labels, e.g., fluorescent, phosphorescent, chemiluminescent, bioluminescent and electrochemiluminescent labels, radioactive labels, enzymes, particles, magnetic substances, electroactive species and the like. Alternatively, a detectable label may signal its presence by participating in specific binding reactions. Examples of such labels include haptens, antibodies, biotin, streptavidin, his-tag, nitrilotriacetic acid, glutathione S-transferase, glutathione and the like.

The term "detection means" refers to a moiety or technique used to detect the presence of the detectable antibody through signal reporting that is then read out in an assay. Typically, detection means employ reagents that amplify an immobilized label such as the label captured onto a microtiter plate, e.g., avidin or streptavidin-HRP.

"Photoluminescence" refers to a process whereby a material luminesces subsequent to the absorption by that material of light (alternatively termed electromagnetic radiation). Fluorescence and phosphorescence are two different types of photoluminescence. "Chemiluminescent" processes involve the creation of the luminescent species by a chemical reaction. "Electro-chemiluminescence" or "ECL" is a process whereby a species, e.g., an antibody, luminesces upon the exposure of that species to electrochemical energy in an appropriate surrounding chemical environment.

An antibody "which binds" an antigen of interest, e.g. a host cell protein, is one that binds the antigen with sufficient affinity such that the antibody is useful as an assay reagent, e.g., as a capture antibody or as a detection antibody. Typically, such an antibody does not significantly cross-react with other polypeptides.

With regard to the binding of a polypeptide to a target molecule, the term "specific binding" or "specifically binds to" or is "specific for" a particular polypeptide or an epitope on a particular polypeptide target means binding that is measurably different from a non-specific interaction. Specific binding can be measured, for example, by determining binding of a target molecule compared to binding of a control molecule, which generally is a molecule of similar structure that does not have binding activity. In some embodiments a preparation of polyclonal antibodies specifically binds DsbA or DsbC. For example, at least about 99% of the antibodies in the polyclonal antibody preparation bind the desired polypeptide (e.g., DsbA or DsbC).

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein.

"Active" or "activity" for the purposes herein refers to form(s) of a polypeptide which retain a biological and/or an immunological activity of native or naturally-occurring polypeptide, wherein "biological" activity refers to a biological function (either inhibitory or stimulatory) caused by a native or naturally-occurring polypeptide other than the ability to induce the production of an antibody against an antigenic epitope possessed by a native or naturally-occurring polypeptide and an "immunological" activity refers to the ability to induce the production of an antibody against an antigenic epitope possessed by a native or naturally-occurring polypeptide.

The term "antagonist" is used in the broadest sense, and includes any molecule that partially or fully blocks, inhibits, or neutralizes a biological activity of a native polypeptide. In a similar manner, the term "agonist" is used in the broadest sense and includes any molecule that mimics a biological activity of a native polypeptide. Suitable agonist or antagonist molecules specifically include agonist or antagonist antibodies or antibody fragments, fragments or amino acid sequence variants of native polypeptides, etc. Methods for identifying agonists or antagonists of a polypeptide may comprise contacting a polypeptide with a candidate agonist or antagonist molecule and measuring a detectable change in one or more biological activities normally associated with the polypeptide.

The term "antibody" herein is used in the broadest sense and specifically covers monoclonal antibodies, polyclonal antibodies, multispecific antibodies (e.g. bispecific antibodies) formed from at least two intact antibodies, and antibody fragments so long as they exhibit the desired biological activity. The term "immunoglobulin" (Ig) is used interchangeable with antibody herein.

Antibodies are naturally occurring immunoglobulin molecules which have varying structures, all based upon the immunoglobulin fold. For example, IgG antibodies have two "heavy" chains and two "light" chains that are disulphide-bonded to form a functional antibody. Each heavy and light chain itself comprises a "constant" (C) and a "variable" (V) region. The V regions determine the antigen binding specificity of the antibody, whilst the C regions provide structural support and function in non-antigen-specific interactions with immune effectors. The antigen binding specificity of an antibody or antigen-binding fragment of an antibody is the ability of an antibody to specifically bind to a particular antigen.

The antigen binding specificity of an antibody is determined by the structural characteristics of the V region. The variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest*, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

Each V region typically comprises three complementarity determining regions ("CDRs", each of which contains a "hypervariable loop"), and four framework regions. An antibody binding site, the minimal structural unit required to bind with substantial affinity to a particular desired antigen, will therefore typically include the three CDRs, and at least three, preferably four, framework regions interspersed there between to hold and present the CDRs in the appropriate conformation. Classical four chain antibodies have antigen binding sites which are defined by $V_H$ and $V_L$ domains in cooperation. Certain antibodies, such as camel and shark antibodies, lack light chains and rely on binding sites formed by heavy chains only. Single domain engineered immunoglobulins can be prepared in which the binding sites are formed by heavy chains or light chains alone, in absence of cooperation between $V_H$ and $V_L$.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a βsheet configuration, connected by three hypervariable regions, which form loops connecting, and in some cases forming part of, the βsheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest*, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody that are responsible for antigen binding. The hypervariable region may comprise amino acid residues from a "complementarity determining region" or "CDR" (e.g., around about residues 24-34 (L1), 50-56 (L2) and 89-97 (L3) in the $V_L$, and around about 31-35B (H1), 50-65 (H2) and 95-102 (H3) in the $V_H$ (Kabat et al., *Sequences of Proteins of Immunological Interest*, 5th Ed. Public Health Service, National Institutes of Health, Bethesda, Md. (1991)) and/or those residues from a "hypervariable loop" (e.g. residues 26-32 (L1), 50-52 (L2) and 91-96 (L3) in the $V_L$, and 26-32 (H1), 52A-55 (H2) and 96-101 (H3) in the $V_H$ (Chothia and Lesk *J. Mol. Biol.* 196:901-917 (1987)).

"Framework" or "FR" residues are those variable domain residues other than the hypervariable region residues as herein defined.

"Hinge region" in the context of an antibody or half-antibody is generally defined as stretching from Glu216 to Pro230 of human IgG1 (Burton, *Molec. Immunol.* 22:161-206 (1985)). Hinge regions of other IgG isotypes may be aligned with the IgG1 sequence by placing the first and last cysteine residues forming inter-heavy chain S—S bonds in the same positions.

The "lower hinge region" of an Fc region is normally defined as the stretch of residues immediately C-terminal to the hinge region, i.e. residues 233 to 239 of the Fc region. Prior to the present invention, FcγR binding was generally attributed to amino acid residues in the lower hinge region of an IgG Fc region.

The "CH2 domain" of a human IgG Fc region usually extends from about residues 231 to about 340 of the IgG. The CH2 domain is unique in that it is not closely paired with another domain. Rather, two N-linked branched carbohydrate chains are interposed between the two CH2 domains of an intact native IgG molecule. It has been speculated that the carbohydrate may provide a substitute for the domain-domain pairing and help stabilize the CH2 domain. Burton, *Molec. Immunol.* 22:161-206 (1985).

The "CH3 domain" comprises the stretch of residues C-terminal to a CH2 domain in an Fc region (i.e. from about amino acid residue 341 to about amino acid residue 447 of an IgG).

"Antibody fragments" comprise a portion of an intact antibody, preferably comprising the antigen binding region thereof. Examples of antibody fragments include Fab, Fab', F(ab')$_2$, and Fv fragments; diabodies; tandem diabodies (taDb), linear antibodies (e.g., U.S. Pat. No. 5,641,870, Example 2; Zapata et al., *Protein Eng.* 8(10):1057-1062 (1995)); one-armed antibodies, single variable domain antibodies, minibodies, single-chain antibody molecules; multispecific antibodies formed from antibody fragments (e.g., including but not limited to, Db-Fc, taDb-Fc, taDb-CH3, (scFV)4-Fc, di-scFv, bi-scFv, or tandem (di,tri)-scFv); and Bi-specific T-cell engagers (BiTEs).

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain (VH), and the first constant domain of one heavy chain (CH1). Pepsin treatment of an antibody yields a single large F(ab')2 fragment which roughly corresponds to two disulfide linked Fab fragments having divalent antigen-binding activity and is still capable of cross-linking antigen. Fab' fragments differ from Fab fragments by having additional few residues at the carboxy terminus of the CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

"Fv" is the minimum antibody fragment that contains a complete antigen-recognition and antigen-binding site. This region consists of a dimer of one heavy chain and one light chain variable domain in tight, non-covalent association. It is in this configuration that the three hypervariable regions of each variable domain interact to define an antigen-binding site on the surface of the $V_H$-$V_L$ dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The Fab fragment also contains the constant domain of the light chain and the first constant domain (CH1) of the heavy chain Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear at least one free thiol group. F(ab')$_2$ antibody fragments originally were produced as pairs of Fab' fragments that have hinge cysteines between them. Other chemical couplings of antibody fragments are also known.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequence of the constant domain of their heavy chains, antibodies can be assigned to different classes. There are five major classes of intact antibodies: IgA, IgD, IgE, IgG, and IgM, and several of these may be further divided into subclasses (isotypes), e.g., IgG1, IgG2, IgG3, IgG4, IgA, and IgA2. The heavy chain constant domains that correspond to the different classes of antibodies are called α, δ, ε, γ, and μ, respectively. The subunit structures and three-dimensional configurations of different classes of immunoglobulins are well known.

"Single-chain Fv" or "scFv" antibody fragments comprise the $V_H$ and $V_L$ domains of antibody, wherein these domains are present in a single polypeptide chain. In some embodiments, the Fv polypeptide further comprises a polypeptide linker between the $V_H$ and $V_L$ domains that enables the scFv to form the desired structure for antigen binding. For a review of scFv see Plückthun in *The Pharmacology of Monoclonal Antibodies*, vol. 113, Rosenburg and Moore eds., Springer-Verlag, New York, pp. 269-315 (1994).

The term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA*, 90:6444-6448 (1993).

The term "multispecific antibody" is used in the broadest sense and specifically covers an antibody that has polyepitopic specificity. Such multispecific antibodies include, but are not limited to, an antibody comprising a heavy chain variable domain ($V_H$) and a light chain variable domain ($V_L$), where the $V_H V_L$ unit has polyepitopic specificity, antibodies having two or more $V_L$ and $V_H$ domains with each $V_H V_L$ unit binding to a different epitope, antibodies having two or more single variable domains with each single variable domain binding to a different epitope, full length antibodies, antibody fragments such as Fab, Fv, dsFv, scFv, diabodies, bispecific diabodies, triabodies, tri-functional antibodies, antibody fragments that have been linked covalently or non-covalently. "Polyepitopic specificity" refers to the ability to specifically bind to two or more different epitopes on the same or different target(s). "Monospecific" refers to the ability to bind only one epitope. According to one embodiment the multispecific antibody is an IgG antibody that binds to each epitope with an affinity of 5 μM to 0.001 µM, 3 µM to 0.001 µM, 1 µM to 0.001 µM, 0.5 µM to 0.001 µM, or 0.1 µM to 0.001 µM.

The expression "single domain antibodies" (sdAbs) or "single variable domain (SVD) antibodies" generally refers to antibodies in which a single variable domain (VH or VL) can confer antigen binding. In other words, the single variable domain does not need to interact with another variable domain in order to recognize the target antigen. Examples of single domain antibodies include those derived from camelids (lamas and camels) and cartilaginous fish (e.g., nurse sharks) and those derived from recombinant methods from humans and mouse antibodies (*Nature* (1989) 341:544-546; *Dev Comp Immunol* (2006) 30:43-56; *Trend Biochem Sci* (2001) 26:230-235; *Trends Biotechnol* (2003): 21:484-490; WO 2005/035572; WO 03/035694; *FEBS Lett* (1994) 339:285-290; WO00/29004; WO 02/051870).

The term "monoclonal antibody" as used herein refers to an antibody obtained from a population of substantially homogeneous antibodies, i.e., the individual antibodies comprising the population are identical and/or bind the same epitope, except for possible variants that may arise during production of the monoclonal antibody, such variants generally being present in minor amounts. In contrast to polyclonal antibody preparations that typically include different antibodies directed against different determinants (epitopes), each monoclonal antibody is directed against a single determinant on the antigen. In addition to their specificity, the monoclonal antibodies are advantageous in that they are uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the methods provided herein may be made by the hybridoma method first described by Kohler et al., *Nature* 256:495 (1975), or may be made by recombinant DNA methods (see, e.g., U.S. Pat. No. 4,816,567). The "monoclonal antibodies" may also be isolated from phage antibody libraries using the techniques described in Clackson et al., *Nature* 352:624-628 (1991) and Marks et al., *J. Mol. Biol.* 222:581-597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Natl. Acad. Sci. USA* 81:6851-6855 (1984)). Chimeric antibodies of interest herein include "primatized" antibodies comprising variable domain antigen-binding sequences derived from a non-human primate (e.g. Old World Monkey, such as baboon, rhesus or cynomolgus monkey) and human constant region sequences (U.S. Pat. No. 5,693,780).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence, except for FR substitution(s) as noted above. The humanized antibody optionally also will comprise at least a portion of an immunoglobulin constant region, typically that of a human immunoglobulin. For further details, see Jones et al., *Nature* 321:522-525 (1986); Riechmann et al., *Nature* 332: 323-329 (1988); and Presta, *Curr. Op. Struct. Biol.* 2:593-596 (1992).

For the purposes herein, an "intact antibody" is one comprising heavy and light variable domains as well as an Fc region. The constant domains may be native sequence constant domains (e.g. human native sequence constant domains) or amino acid sequence variant thereof. Preferably, the intact antibody has one or more effector functions.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light chain and heavy chain variable domains.

A "naked antibody" is an antibody (as herein defined) that is not conjugated to a heterologous molecule, such as a cytotoxic moiety or radiolabel.

As used herein, the term "immunoadhesin" designates molecules which combine the binding specificity of a heterologous protein (an "adhesin") with the effector functions of immunoglobulin constant domains. Structurally, the immunoadhesins comprise a fusion of an amino acid sequence with a desired binding specificity, which amino acid sequence is other than the antigen recognition and binding site of an antibody (i.e., is "heterologous" compared to a constant region of an antibody), and an immunoglobulin constant domain sequence (e.g., CH2 and/or CH3 sequence of an IgG). Exemplary adhesin sequences include contiguous amino acid sequences that comprise a portion of a receptor or a ligand that binds to a protein of interest. Adhesin sequences can also be sequences that bind a protein of interest, but are not receptor or ligand sequences (e.g., adhesin sequences in peptibodies). Such polypeptide sequences can be selected or identified by various methods, include phage display techniques and high throughput sorting methods. The immunoglobulin constant domain sequence in the immunoadhesin can be obtained from any immunoglobulin, such as IgG-1, IgG-2, IgG-3, or IgG-4 subtypes, IgA (including IgA-1 and IgA-2), IgE, IgD, or IgM.

In some embodiments, antibody "effector functions" refer to those biological activities attributable to the Fc region (a native sequence Fc region or amino acid sequence variant Fc region) of an antibody, and vary with the antibody isotype. Examples of antibody effector functions include: Clq binding and complement dependent cytotoxicity; Fc receptor binding; antibody-dependent cell-mediated cytotoxicity (ADCC); phagocytosis; down regulation of cell surface receptors.

"Complement dependent cytotoxicity" or "CDC" refers to the ability of a molecule to lyse a target in the presence of complement. The complement activation pathway is initiated by the binding of the first component of the complement system (Clq) to a molecule (e.g. polypeptide (e.g., an antibody)) complexed with a cognate antigen. To assess complement activation, a CDC assay, e.g. as described in Gazzano-Santoro et al., *J. Immunol. Methods* 202:163 (1996), may be performed.

"Antibody-dependent cell-mediated cytotoxicity" and "ADCC" refer to a cell-mediated reaction in which nonspecific cytotoxic cells that express Fc receptors (FcRs) (e.g. Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. FcR expression on hematopoietic cells in summarized is Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al., *Proc. Natl. Acad. Sci. (USA)* 95:652-656 (1998).

"Human effector cells" are leukocytes that express one or more FcRs and perform effector functions. In some embodiments, the cells express at least FcγRIII and carry out ADCC effector function. Examples of human leukocytes that mediate ADCC include peripheral blood mononuclear cells (PBMC), natural killer (NK) cells, monocytes, cytotoxic T cells and neutrophils; with PBMCs and NK cells being preferred.

The terms "Fc receptor" or "FcR" are used to describe a receptor that binds to the Fc region of an antibody. In some embodiments, the FcR is a native sequence human FcR. Moreover, a preferred FcR is one that binds an IgG antibody (a gamma receptor) and includes receptors of the FcγRI, FcγRII, and Fcγ RIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see Daëron, *Annu. Rev. Immunol.* 15:203-234 (1997)). FcRs are reviewed in Ravetch and Kinet, *Annu. Rev. Immunol* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)).

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

The term "impurities" as used herein refers to materials or substances that are different from the desired polypeptide product. The impurities include, without limitation: host cell materials, such as *E. coli* host cell protein (ECP); leached Protein A; nucleic acid; a variant, fragment, aggregate or derivative of the desired polypeptide; another polypeptide; endotoxin; viral contaminant; cell culture media component, etc. In some examples, the impurity may be a host cell protein (HCP) from, for example but not limited to, a bacterial cell such as an *E. coli* cell (e.g., ECP). In some embodiments, the impurity may be clipped DsbA or DsbC and/or aggregates of DsbA or DsbC.

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. In certain embodiments, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al., Kuby, *Immunology*, 6th ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The term "sequential" as used herein with regard to chromatography refers to having a first chromatography followed by a second chromatography. Additional steps may be included between the first chromatography and the second chromatography.

The term "continuous" as used herein with regard to chromatography refers to having a first chromatography material and a second chromatography material either directly connected or some other mechanism which allows for continuous flow between the two chromatography materials.

"Loading density" refers to the amount, e.g. grams, of composition put in contact with a volume of chromatography material, e.g. liters. In some examples, loading density is expressed in g/L.

Reference to "about" a value or parameter herein includes (and describes) variations that are directed to that value or parameter per se. For example, description referring to "about X" includes description of "X".

As used herein and in the appended claims, the singular forms "a," "or," and "the" include plural referents unless the context clearly dictates otherwise. It is understood that aspects and variations of the invention described herein include "consisting" and/or "consisting essentially of" aspects and variations.

II. Methods of Purification

Provided herein are methods for generating ultrapure preparations of DsbA and DsbC. In some embodiments, the preparations comprise more than about any of 95.0%, 96.0%, 97.0%, 98.0%, 99.0%, 99.1%, 99.2%, 99.3%, 99.4%, 99.5%, 99.6%, 99.7%, 99.8%, 99.9% pure DsbA or DsbC. In some embodiments, a preparation that is 99% pure DsbA or 99% pure DsbC indicates that less than 1% of the material in the preparation are substances present in the cells or cell lysates (e.g., protein, nucleic acids, lipids, etc.) present during the production of the DsbA or DsbC. A 99% pure preparation of DsbA or DsbC may contain buffers, salts or other excipients used in the purification or formulation of DsbA or DsbC.

A. Purification of DsbA

In some aspects, the invention provides methods for generating ultrapure preparations of DsbA. In some embodiments, the DsbA is produced by overexpressing DsbA in a bacterial fermentation culture such as an *E. coli* culture. Following fermentation, bacterial cells are collected and centrifuged. The resultant cell paste is resuspended in a lysis buffer (e.g., 10 mM MOPS pH 7.1) and lysed (e.g., by using a microfluidizer). In some embodiments, the cell lysate is conditioned with polyethyleneimine (PEI). In some embodiments, the cell lysate is conditioned with PEI at a final concentration of more than about any of 0.01%, 0.05%, 0.1%, 0.2%, 0.3%, 0.4%, 0.5%, 0.6%, 0.7%, 0.8%, 0.9%, or 1.0%. In some embodiments, the cell lysate is conditioned with PEI for more than about any of 15 min., 30 min., 45 min., 1 hr., 2 hr., 3 hr., 4 hr., 5 hr., 6 hr., 8 hr., 12 hr., 16 hr., 20 hr., or 24 hr. In some embodiments, the cell lysate is conditioned with PEI at more than about any of 0° C., 4° C., or 21° C. In some embodiments, the cell lysate is conditioned with PEI at ambient temperature (~21° C.). In some embodiments, the PEI-conditioned lysate is centrifuged to remove particulates. In some embodiments, the PEI-conditioned lysate is filtered prior to chromatography. In some embodiments, the PEI-conditioned lysate is filtered through a 22 μm filter prior to chromatography.

In some embodiments, the method comprises methods for purifying a DsbA polypeptide from a cell lysate comprising the DsbA polypeptide, the method comprising a) adding polyethyleneimine (PEI) to a final concentration of about 0.01% to about 1.0% to a cell lysate comprising the DsbA polypeptide, b) clarifying the cell lysate by centrifugation, c) applying the clarified cell lysate comprising the DsbA polypeptide to an anion exchange chromatography material, d) eluting the DsbA polypeptide from the anion exchange chromatography material to generate an anion exchange eluate comprising the DsbA polypeptide, e) applying the anion exchange eluate comprising the DsbA polypeptide to a cation exchange chromatography material, f) eluting the DsbA polypeptide from the cation exchange chromatography material to generate a cation exchange eluate comprising the purified DsbA polypeptide.

In some embodiments of any of the methods described herein, the anion exchange chromatography material is a solid phase that is positively charged and has free anions for exchange with anions in an aqueous solution passed over or through the solid phase. In some embodiments of any of the methods described herein, the anion exchange material may be a membrane, a monolith, or resin. In an embodiment, the anion exchange material may be a resin. In some embodiments, the anion exchange material may comprise a primary amine, a secondary amine, a tertiary amine or a quarternary ammonium ion functional group, a polyamine functional group, or a diethylaminoaethyl functional group. In some embodiments of the above, the anion exchange chromatography material is an anion exchange chromatography column. In some embodiments of the above, the anion exchange chromatography material is an anion exchange chromatography membrane.

In some embodiments of any of the methods described herein, the cation exchange material is a solid phase that is negatively charged and has free cations for exchange with cations in an aqueous solution passed over or through the solid phase. In some embodiments of any of the methods described herein, the cation exchange material may be a membrane, a monolith, or resin. In some embodiments, the cation exchange material may be a resin. The cation exchange material may comprise a carboxylic acid functional group or a sulfonic acid functional group such as, but not limited to, sulfonate, carboxylic, carboxymethyl sulfonic acid, sulfoisobutyl, sulfoethyl, carboxyl, sulphopropyl, sulphonyl, sulphoxyethyl, or orthophosphate. In some embodiments of the above, the cation exchange chromatography material is a cation exchange chromatography column. In some embodiments of the above, the cation exchange chromatography material is a cation exchange chromatography membrane. In some embodiments of the invention, the chromatography material is not a cation exchange chromatography material.

In some embodiments of any of the methods described herein, the ion exchange material may utilize a conventional chromatography material or a convective chromatography material. The conventional chromatography materials include, for example, perfusive materials (e.g., poly (styrene-divinylbenzene) resin) and diffusive materials (e.g., cross-linked agarose resin). In some embodiments, the poly (styrene-divinylbenzene) resin can be Poros resin. In some embodiments, the cross-linked agarose resin may be sulphopropyl-Sepharose® Fast Flow ("SPSFF") resin. The convective chromatography material may be a membrane (e.g., polyethersulfone) or monolith material (e.g. cross-linked polymer). The polyethersulfone membrane may be Mustang. The cross-linked polymer monolith material may be cross-linked poly(glycidyl methacrylate-co-ethylene dimethacrylate).

Examples of anion exchange materials are known in the art and include, but are not limited to Poros HQ 50, Poros PI 50, Poros D, Mustang Q, Q Sepharose® FF (QSFF), and DEAE Sepharose® or equivalents thereof. In some embodiments, the anion exchange material is a weak anion exchange material; e.g. DEAE. In other embodiments, the anion exchange material is a strong anion exchange material; e.g., QSFF.

Examples of cation exchange materials are known in the art include, but are not limited to Mustang S, Sartobind S, SO3 Monolith, S Ceramic HyperD, Poros XS, Poros HS50, Poros HS20, SPSFF, SP-Sepharose® XL (SPXL), CM Sepharose® Fast Flow, Capto S, Fractogel Se HiCap, Fractogel SO3, or Fractogel COO or equivalents thereof. In some embodiments of any of the methods described herein, the cation exchange material is Poros HS50. In some embodiments, the Poros HS resin may be Poros HS 50 µm or Poros HS 20 µm particles. In some embodiments, the cation exchange material is a weak cation exchange material; e.g., CM Sepharose® or equivalents thereof. In other embodiments, the cation exchange material is a strong cation exchange material; e.g., POROS HS 50 or equivalents thereof.

Loading of the composition comprising DsbA on the chromatography material may be optimized for separation of the DsbA product from impurities. In some embodiments, loading on the composition onto the chromatography material is optimized for binding of the impurities to the chromatography material. For example, the composition may be loaded onto the chromatography material, e.g. a chromatography column, in a load buffer at a number of different pH while the conductivity of the load buffer is constant. Alternatively, the composition may be loaded onto the chromatography material in a load buffer at a number of different conductivities while the pH of the load buffer is constant. Upon completion of loading the composition on the chromatography material and elution of the product from the chromatography material into a pool fraction, the amount of contaminant in the pool fraction provides information regarding the separation of the product from the impurities for a given pH or conductivity.

In some embodiments of any of the methods described herein, the composition comprising DsbA is loaded onto an anion exchange chromatography material at a loading density of the polypeptide of less than or equal to about any of 10 mg/mL, 9 mg/mL, 8 mg/mL, 7 mg/mL, 6 mg/mL, 5 mg/mL, 4 mg/mL, 3 mg/mL, 2 mg/mL, or 1 mg/mL of the anion exchange chromatography material. The composition may be loaded onto an anion chromatography material at a loading density of the polypeptide of between about any of 1 mg/mL and 2 mg/mL, 2 mg/mL and 3 mg/mL, 3 mg/mL and 4 mg/mL, 4 mg/mL and 5 mg/mL, 5 mg/mL and 6 mg/mL, 6 mg/mL and 7 mg/mL, 7 mg/mL and 8 mg/mL, 8 mg/mL and 9 mg/mL, or 9 mg/mL and 10 mg/mL of anion exchange chromatography material. In some embodiments, the anion exchange chromatography material a quarternary amine crosslinked to agarose; e.g., QSFF.

In some embodiments of any of the methods described herein, the composition comprising DsbA is loaded onto a cation exchange chromatography material at a loading density of the polypeptide of less than or equal to about any of 10 mg/mL, 9 mg/mL, 8 mg/mL, 7 mg/mL, 6 mg/mL, 5 mg/mL, 4 mg/mL, 3 mg/mL, 2 mg/mL, or 1 mg/mL of the anion exchange chromatography material. The composition may be loaded onto an cation chromatography material at a loading density of the polypeptide of between about any of 1 mg/mL and 2 mg/mL, 2 mg/mL and 3 mg/mL, 3 mg/mL and 4 mg/mL, 4 mg/mL and 5 mg/mL, 5 mg/mL and 6 mg/mL, 6 mg/mL and 7 mg/mL, 7 mg/mL and 8 mg/mL, 8 mg/mL and 9 mg/mL, or 9 mg/mL and 10 mg/mL of cation exchange chromatography material. In some embodiments, the cation exchange chromatography material is a sulfopropyl moiety crosslinked to a poly(styrene-divinylbenzene) matrix; e.g., POROS HS50 or equivalents thereof.

Elution of the DsbA from the chromatography material may be optimized for yield of DsbA with minimal impurities and at minimal pool volume. For example, the composition may be loaded onto the chromatography material, e.g. a chromatography column, in a load buffer. Upon completion of load, the product is eluted with buffers at a number of different pH while the conductivity of the elution buffer is constant. Alternatively, the product may be eluted from the chromatography material in an elution buffer at a number of different conductivities while the pH of the elution buffer is constant. Upon completion of elution of the product from the chromatography material, the amount of contaminant in the pool fraction provides information regarding the separation of the product from the impurities for a given pH or conductivity. Elution of the product in a high number of fractions (e.g. eight column volumes) indicates "tailing" of the elution profile. In some embodiments of the invention, tailing of the elution is minimized.

Various buffers which can be employed depending, for example, on the desired pH of the buffer, the desired conductivity of the buffer, the characteristics of the protein of interest, and the purification method. In some embodiments of any of the methods described herein, the methods comprise using a buffer. The buffer can be a loading buffer, an equilibration buffer, or a wash buffer. In some embodiments, one or more of the loading buffer, the equilibration buffer, and/or the wash buffer are the same. In some embodiments, the loading buffer, the equilibration buffer, and/or the wash buffer are different. In some embodiments of any of the methods described herein, the buffer comprises a salt. The loading buffer may comprise sodium chloride, sodium acetate, or a mixture thereof. In some embodiments, the loading buffer is a sodium chloride buffer. In some embodiments, the loading buffer is a sodium acetate buffer.

Load, as used herein, is the composition loaded onto a chromatography material. Loading buffer is the buffer used to load the composition comprising DsbA onto a chromatography material. The chromatography material may be equilibrated with an equilibration buffer prior to loading the composition which is to be purified. In some examples, the wash buffer is used after loading the composition onto a chromatography material and before elution of the polypeptide of interest from the solid phase.

Elution, as used herein, is the removal of the product, e.g. DsbA, from the chromatography material. Elution buffer is the buffer used to elute the polypeptide or other product of interest from a chromatography material. In many cases, an elution buffer has a different physical characteristic than the load buffer. For example, the elution buffer may have a different conductivity than load buffer or a different pH than the load buffer. In some embodiments, the elution buffer has a lower conductivity than the load buffer. In some embodiments, the elution buffer has a higher conductivity than the load buffer. In some embodiments, the elution buffer has a lower pH than the load buffer. In some embodiments, the elution buffer has a higher pH than the load buffer. In some embodiments the elution buffer has a different conductivity and a different pH than the load buffer. The elution buffer can have any combination of higher or lower conductivity and higher or lower pH.

Conductivity refers to the ability of an aqueous solution to conduct an electric current between two electrodes. In solution, the current flows by ion transport. Therefore, with an increasing amount of ions present in the aqueous solution, the solution will have a higher conductivity. The basic unit of measure for conductivity is the Siemen (or mho), mho (mS/cm), and can be measured using a conductivity meter, such as various models of Orion conductivity meters. Since electrolytic conductivity is the capacity of ions in a solution to carry electrical current, the conductivity of a solution may be altered by changing the concentration of ions therein. For example, the concentration of a buffering agent and/or the concentration of a salt (e.g. sodium chloride, sodium acetate, or potassium chloride) in the solution may be altered in order to achieve the desired conductivity. Preferably, the salt concentration of the various buffers is modified to achieve the desired conductivity.

In some embodiments of any of the methods described herein, the load buffer has a conductivity of greater than about any of 4.0 mS/cm, 4.5 mS/cm, 5.0 mS/cm, 5.5 mS/cm, 6.0 mS/cm, 6.5 mS/cm, 7.0 mS/cm, 7.5 mS/cm, 8.0 mS/cm, 8.5 mS/cm, 9.0 mS/cm, 9.5 mS/cm, or 10 mS/cm. The conductivity may be between about any of 4 mS/cm and 17 mS/cm, 4 mS/cm and 10 mS/cm, 4 mS/cm and 7 mS/cm, 5 mS/cm and 17 mS/cm, 5 mS/cm and 10 mS/cm, or 5 mS/cm and 7 mS/cm. In some embodiments, the conductivity is about any of 4 mS/cm, 4.5 mS/cm, 5.0 mS/cm, 5.5 mS/cm, 6.0 mS/cm, 6.5 mS/cm, 7.0 mS/cm, 7.5 mS/cm, 8.0 mS/cm, 8.5 mS/cm, 9.0 mS/cm, 9.5 mS/cm, or 10 mS/cm. In one aspect, the conductivity is the conductivity of the loading buffer, the equilibration buffer, and/or the wash buffer. In some embodiments, the conductivity of one or more of the loading buffer, the equilibration buffer, and the wash buffer are the same. In some embodiments, the conductivity of the loading buffer is different from the conductivity of the wash buffer and/or equilibration buffer.

In some embodiments, the elution buffer has a conductivity greater than the conductivity of the load buffer. In some embodiments of any of the methods described herein, the elution buffer has a conductivity of greater than about any of 5 mS/cm, 10 mS/cm, 15 mS/cm, 20 mS/cm, 25 mS/cm, 30 mS/cm, 35 mS/cm, 40 mS/cm, 45 mS/cm, 50 mS/cm, 55 mS/cm, 60 mS/cm, 65 mS/cm, 70 mS/cm, 75 mS/cm, 80 mS/cm, 85 mS/cm, 90 mS/cm, 95 mS/cm, or 100 mS/cm. In some embodiments, the elution buffers described above are used in anion exchange or cation exchange chromatography. In some embodiments, the conductivity of the elution buffer is altered by altering the salt concentration of the elution buffer.

In some aspects of any of the above embodiments, the conductivity of the elution buffer changed from the load and/or wash buffer isocratically, by step gradient or by linear gradient.

In some embodiments, DsbA is eluted from the anion exchange chromatography material with the following steps: 1) about 15% of about 25 mM Tris and about 250 mM NaCl at about pH 9.2 for about four column volumes, 2) about 20% of about 25 mM Tris and about 250 mM NaCl at about pH 9.2 for about four column volumes, and 3) about 25% of about 25 mM Tris and about 250 mM NaCl at about pH 9.2 until DsbA elutes from the column. In some embodiments, DsbA is eluted from the cation exchange chromatography using a salt gradient from about 0% to about 60% 12 mM MES and 1 M NaCl over 15 column volumes.

In some embodiments of any of the methods described herein, the anion exchange load buffer has a pH of less than about any of 10, 9, 8, 7, 6, or 5. In some embodiments of any of the methods described herein, the load buffer has a pH of greater than about any of 4, 5, 6, 7, 8, or 9. In some embodiments, the pH of one or more of the loading buffer, the equilibration buffer, and/or the wash buffer are the same. In some embodiments, the pH of the loading buffer is different from the pH of the equilibration buffer and/or the wash buffer.

In some embodiments, the elution buffer has a pH less than the pH of the load buffer. In some embodiments of any of the methods described herein, the elution buffer has a pH of less than about any of 8, 7, 6, 5, 4, 3 or 2. The pH of the elution buffer may be between about any of 4 and 9, 4 and 8, 4 and 7, 4 and 6, 4 and 5, 5 and 9, 5 and 8, 5 and 7, 5 and 6, 6 and 9, 6 and 8, 6 and 7. In some embodiments, the pH of the elution buffer is about any of 4.0, 4.5, 5.0, 5.5, 6.0, 6.5, 7/0, 7.5, 8.0, 8.5 or 9.0.

In some embodiments of any of the methods described herein, the cation exchange load buffer has a pH of less than about any of 4, 5, 6, or 7. In some embodiments of any of the methods described herein, the load buffer has a pH of greater than about any of 4, 5, 6, or 7. In some embodiments, the pH of one or more of the loading buffer, the equilibration buffer, and/or the wash buffer are the same. In some embodiments, the pH of the loading buffer is different from the pH of the equilibration buffer and/or the wash buffer.

In some embodiments, the elution buffer has a pH greater than the pH of the load buffer. In some embodiments of any of the methods described herein, the elution buffer has a pH of greater than about any of 5, 6, 7, 8, or 9. The pH of the elution buffer may be between about any of 4 and 9, 5 and 9, 6 and 9, 7 and 9, 8 and 9, 4 and 8, 5 and 8, 6 and 8, 7 and 8, 4 and 7, 5 and 7, and 6 and 7.

In some embodiments of any of the methods described herein, the flow rate is less than about any of 50 CV/hr, 40 CV/hr, or 30 CV/hr. The flow rate may be between about any of 5 CV/hr and 50 CV/hr, 10 CV/hr and 40 CV/hr, or 18 CV/hr and 36 CV/hr. In some embodiments, the flow rate is about any of 9 CV/hr, 18 CV/hr, 25 CV/hr, 30 CV/hr, 36 CV/hr, or 40 CV/hr. In some embodiments of any of the methods described herein, the flow rate is less than about any of 200 cm/hr, 150 cm/hr, 100 cm/hr, 75 cm/hr, or 50 cm/hr. The flow rate may be between about any of 25 cm/hr and 200 cm/hr, 25 cm/hr and 175 cm/hr, 25 cm/hr and 150 cm/hr, 25 cm/hr and 100 cm/hr, 50 cm/hr and 100 cm/hr, or 65 cm/hr and 85 cm/hr.

Bed height is the height of chromatography material used. In some embodiments of any of the method described herein, the bed height is greater than about any of 3 cm, 10 cm, 15 cm, 20 cm, 25 cm, 30 cm, 35 cm, 40 cm, 45 cm, or 50 cm. The bed height may be between about any of 3 cm and 50 cm, 5 cm and 35 cm, 3 cm and 35 cm, or 5 cm and 50 cm. In some embodiments, bed height is determined based on the amount of polypeptide or impurities in the load.

In some embodiments, the chromatography is in a column of vessel with a volume of greater than about 1 mL, 2 mL, 3 mL, 4 mL, 5 mL, 6 mL, 7 mL, 8 mL, 9 mL, 10 mL, 15 mL, 20 mL, 25 mL, 30 mL, 40 mL, 50 mL, 75 mL, 100 mL, or 200 mL.

In some embodiments of the invention, fractions are collected from the chromatography. In some embodiments, fractions collected are greater than about 0.01 CV, 0.02 CV, 0.03 CV, 0.04 CV, 0.05 CV, 0.06 CV, 0.07 CV, 0.08 CV, 0.09 CV, 0.1 CV, 0.2 CV, 0.3 CV, 0.4 CV, 0.5 CV, 0.6 CV, 0.7 CV, 0.8 CV, 0.9 CV, 1.0 CV, 2.0 CV, 3.0 CV, 4.0 CV, 5.0 CV, 6.0 CV, 7.0 CV, 8.0 CV, 9.0 CV, or 10.0 CV. In some embodiments, fractions containing the product, e.g. polypeptide, are pooled. In some embodiments, fractions containing the polypeptide from the load fractions and from the elution fractions are pooled. The amount of polypeptide in a fraction can be determined by one skilled in the art; for example, the amount of polypeptide in a fraction can be determined by UV spectroscopy. In some embodiments, fractions containing detectable polypeptide fragment are pooled. In some embodiments, the presence and purity of DsbA in a fraction is determined by size exclusion chromatography.

Exemplary Embodiment

In some embodiments, the invention provides the following exemplary but nonlimiting methods for producing an ultrapure preparation of DsbA. DsbA is expressed in E. coli. The cell paste is suspended (50 g cell paste/1 L) in 10 mM MOPS pH 7.1 and mixed until the suspension is homogenous. Cell lysis is performed using a Microfluidizer 110F with 3 passes at house pressure (~7000 psi). The homogenate is conditioned to 0.1% PEI (using a 10% PEI stock solution) and mixed for 30 min at ambient temperature (~21° C.). The suspension is centrifuged in a Sorval RC-5B+ centrifuge using a "GSA" rotor at 8500 rpm for 30 min. The centrate is collected and filtered through a 0.22 um Durapore filter (a) Q-Sepharose® Step The cell lysate is applied to a Q-Sepharose® FF (GE) in a bind and elute mode. The column Height is about 20-30 cm in height, the flow rate is 150 cm/h and the load density is ≤6 mg/mL. The column is pre-equilibrated with 25 mM Tris, 1M NaCl, pH 9.2, 86 mS/cm with 4 column volumes (CV). The column is equilibrated with 25 mM Tris, pH 9.1, 0.3 mS/cm with 4 CV. The centrate comprising DsbA is diluted with water (1:1), then pH-adjust to 9.0 with 1.5M Tris Base pH 9.0, conductivity ~1.0 mS/cm, ≤6 mg/mL. The column is then washed with 6 CV of Equilibration Buffer. DsbA is eluted from the column using a step gradient increase in salt concentration. Buffer B is 25 mM Tris, 250 mM NaCl, pH 9.2, 26 mS/cm. DsbA is eluted from the column by first applying 15% buffer B for 4 CV, then 20% buffer B for 4 CV and finally 25% buffer B for remainder of elution phase. The pools are assayed by SEC and pooled based on the fractions containing the largest amount of DsbA.

(b) POROS HS50 Step

The pooled QSFF fraction is then applied to a POROS HS50 column in bind and elute mode. The QSFF fraction is adjusted to pH 5.0 with 2.0 M Acetic Acid. The column height is about 20-30 cm, the flow rate is about 150 cm/h, and the load density is about ≤6 mg/mL. The POROS HS50 column is first equilibrated with 12.5 mM MES, pH 5.5, 0.4 mS/cm for 4 CV. The QSFF Pool pH, adjusted to 5.0 with 2M Acetic Acid, and then diluted with water (1:2) pH 5.0, 0.4 mS/cm is loaded on the POROS HS50 column. The column is then washed with 5 CV Equilibration Buffer. The DsbA is eluted from the column with a salt gradient. Buffer B is 12.5 mM MES, 250 mM NaCl pH 5.5, 25 mS/cm. The gradient is 0 to 60% B over 15 CV. 1 CV fractions are collected peak. Fractions are analyzed and pooled based on purity by SDS-PAGE Gel and SEC. The POROS pool is concentrated to ~3.0 mg/mL using 10 kD Centricon membranes (Millipore) that are centrifuged for ~30 min at 3000 rpm with Sorval RC-3B centrifuge.

B. Purification of DsbC

In some aspects, the invention provides methods for generating ultrapure preparations of DsbC. In some embodiments, the DsbC is produced by overexpressing DsbC in a bacterial fermentation culture such as an E. coli culture. Following fermentation, bacterial cells are collected and centrifuged. The resultant cell paste is resuspended in a lysis buffer (e.g., 10 mM MOPS pH 7.1) and lysed (e.g., by using a microfluidizer). In some embodiments, the cell lysate is conditioned with polyethyleneimine (PEI). In some embodiments, the cell lysate is conditioned with PEI at a final concentration of more than about any of 0.01%, 0.05%, 0.1%, 0.2%, 0.3%, 0.4%, 0.5%, 0.6%, 0.7%, 0.8%, 0.9%, or 1.0%. In some embodiments, the cell lysate is conditioned with PEI for more than about any of 15 min., 30 min., 45 min., 1 hr., 2 hr., 3 hr., 4 hr., 5 hr., 6 hr., 8 hr., 12 hr., 16 hr., 20 hr., or 24 hr. In some embodiments, the cell lysate is conditioned with PEI at more than about any of 0° C., 4° C., or 21° C. In some embodiments, the cell lysate is conditioned with PEI at ambient temperature (~21° C.). In some embodiments, the PEI-conditioned lysate is centrifuged to remove particulates. In some embodiments, the PEI-conditioned lysate is filtered prior to chromatography. In some embodiments, the PEI-conditioned lysate is filtered through a 22 μm filter prior to chromatography.

In some embodiments, the method comprises methods for purifying a DsbC polypeptide from a cell lysate comprising the DsbC polypeptide, the method comprising a) adding polyethyleneimine (PEI) to a final concentration of about 0.01% to about 1.0% to a cell lysate comprising the DsbC polypeptide, b) clarifying the cell lysate by centrifugation, c) applying the clarified cell lysate comprising the DsbC polypeptide to an anion exchange chromatography material, d) eluting the DsbC polypeptide from the anion exchange chromatography material to generate an anion exchange eluate comprising the DsbC polypeptide, e) applying the anion exchange eluate comprising the DsbC polypeptide to a hydrophobic interaction chromatography (HIC) material, f) eluting the DsbC polypeptide from the HIC material to generate a HIC eluate, g) applying the HIC eluate comprising the DsbC polypeptide to a size exclusion chromatography, h) collecting fractions from the size exclusion chromatography comprising the purified DsbC polypeptide.

In some embodiments of any of the methods described herein, the anion exchange chromatography material is a solid phase that is positively charged and has free anions for exchange with anions in an aqueous solution passed over or through the solid phase. In some embodiments of any of the methods described herein, the anion exchange material may be a membrane, a monolith, or resin. In an embodiment, the anion exchange material may be a resin. In some embodiments, the anion exchange material may comprise a primary amine, a secondary amine, a tertiary amine or a quarternary ammonium ion functional group, a polyamine functional group, or a diethylaminoethyl functional group. In some embodiments of the above, the anion exchange chromatography material is an anion exchange chromatography column. In some embodiments of the above, the anion exchange chromatography material is an anion exchange chromatography membrane.

In some embodiments of any of the methods described herein, the anion exchange material may utilize a conventional chromatography material or a convective chromatography material. The conventional chromatography materials include, for example, perfusive materials (e.g., poly (styrene-divinylbenzene) resin) and diffusive materials (e.g., cross-linked agarose resin). In some embodiments, the poly (styrene-divinylbenzene) resin can be Poros resin. In some embodiments, the cross-linked agarose resin may be sulphopropyl-Sepharose® Fast Flow ("SPSFF") resin. The convective chromatography material may be a membrane (e.g., polyethersulfone) or monolith material (e.g. cross-linked polymer). The polyethersulfone membrane may be Mustang. The cross-linked polymer monolith material may be cross-linked poly(glycidyl methacrylate-co-ethylene dimethacrylate).

Examples of anion exchange materials are known in the art and include, but are not limited to Poros HQ 50, Poros PI 50, Poros D, Mustang Q, Q Sepharose® FF (QSFF), and DEAE Sepharose® or equivalents thereof. In some embodiments, the anion exchange material is a weak anion exchange material; e.g. DEAE. In other embodiments, the anion exchange material is a strong anion exchange material; e.g., QSFF. In some embodiments, the anion exchange material used for the purification of DsbC is a weak anion exchange material. In some embodiments the weak anion exchange material comprises a quarternary amine. In some embodiments, the quarternary amine is linked to crosslinked agarose. In some embodiments, the anion exchange material used for the purification of DsbC is DEAE Sepharose®.

In some embodiments of any of the methods described herein, the hydrophobic interaction chromatography (HIC) is a liquid chromatography technique that separates biomolecules according to hydrophobicity. Examples of HIC chromatography materials include, but are not limited to, Toyopearl hexyl 650, Toyopear butyl 650, Toyopearl phenyl 650, Toyopearl ether 650, Source, Resource, Sepharose® Hi-Trap, Octyl Sepharose®, phenyl Sepharose®. In some embodiments of the above, the HIC chromatography material is a HIC chromatography column. In some embodiments of the above, the HIC chromatography material is a HIC chromatography membrane. In some embodiments the HIC material comprises a phenyl moiety. In some embodiments, the phenyl moiety is linked to crosslinked agarose. In some embodiments, the HIC material used for the purification of DsbC is phenyl Sepharose®.

In some embodiments of any of the methods described herein, the size exclusion chromatography is a liquid chromatography technique that separates biomolecules according to their size and shape. Size exclusion chromatography materials come in different pore size for efficient separation of molecules of particular weight ranges. Examples of size exclusion chromatography materials include, but are not limited to, dextran, porous agarose particles, crosslinked agarose, crosslinked agarose and dextran, and crosslinked acrylamide. Examples of size exclusion chromatography materials include, but are not limited to Sephadex, Superdex, Sephacryl, TSKgel, and Bio-Gel. In some embodiments, Superdex 75 size exclusion chromatography is used in the purification of DsbC.

Loading of the composition comprising DsbC on the chromatography material may be optimized for separation of the DsbC product from impurities. In some embodiments, loading on the composition onto the chromatography material is optimized for binding of the impurities to the chromatography material. For example, the composition may be loaded onto the chromatography material, e.g. a chromatography column, in a load buffer at a number of different pH while the conductivity of the load buffer is constant. Alternatively, the composition may be loaded onto the chromatography material in a load buffer at a number of different conductivities while the pH of the load buffer is constant. Upon completion of loading the composition on the chromatography material and elution of the product from the chromatography material into a pool fraction, the amount of contaminant in the pool fraction provides information regarding the separation of the product from the impurities for a given pH or conductivity.

In some embodiments of any of the methods described herein, the composition comprising DsbC is loaded onto an anion exchange chromatography material at a loading density of the polypeptide of less than or equal to about any of 10 mg/mL, 9 mg/mL, 8 mg/mL, 7 mg/mL, 6 mg/mL, 5 mg/mL, 4 mg/mL, 3 mg/mL, 2 mg/mL, or 1 mg/mL of the anion exchange chromatography material. The composition may be loaded onto an anion chromatography material at a loading density of the polypeptide of between about any of 1 mg/mL and 2 mg/mL, 2 mg/mL and 3 mg/mL, 3 mg/mL and 4 mg/mL, 4 mg/mL and 5 mg/mL, 5 mg/mL and 6 mg/mL, 6 mg/mL and 7 mg/mL, 7 mg/mL and 8 mg/mL, 8 mg/mL and 9 mg/mL, or 9 mg/mL and 10 mg/mL of anion exchange chromatography material. In some embodiments, the anion exchange chromatography material a quarternary amine crosslinked to agarose; e.g., DEAE Sepharose®.

In some embodiments of any of the methods described herein, the composition comprising DsbC is loaded onto a HIC material at a loading density of the polypeptide of less than or equal to about any of 10 mg/mL, 9 mg/mL, 8 mg/mL, 7 mg/mL, 6 mg/mL, 5 mg/mL, 4 mg/mL, 3 mg/mL, 2 mg/mL, or 1 mg/mL of HIC material. The composition may be loaded onto HIC material at a loading density of the polypeptide of between about any of 1 mg/mL and 2 mg/mL, 2 mg/mL and 3 mg/mL, 3 mg/mL and 4 mg/mL, 4 mg/mL and 5 mg/mL, 5 mg/mL and 6 mg/mL, 6 mg/mL and 7 mg/mL, 7 mg/mL and 8 mg/mL, 8 mg/mL and 9 mg/mL, or 9 mg/mL and 10 mg/mL of HIC material. In some embodiments, the HIC material is a phenyl moiety crosslinked to crosslinked agarose; e.g., Phenyl Sepharose®.

Elution of the DsbC from the chromatography material may be optimized for yield of DsbC with minimal impurities and at minimal pool volume. For example, the composition may be loaded onto the chromatography material, e.g. a chromatography column, in a load buffer. Upon completion of load, the product is eluted with buffers at a number of different pH while the conductivity of the elution buffer is constant. Alternatively, the product may be eluted from the chromatography material in an elution buffer at a number of different conductivities while the pH of the elution buffer is constant. Upon completion of elution of the product from the chromatography material, the amount of contaminant in the pool fraction provides information regarding the separation of the product from the impurities for a given pH or conductivity. Elution of the product in a high number of fractions (e.g. eight column volumes) indicates "tailing" of the elution profile. In some embodiments of the invention, tailing of the elution is minimized.

Various buffers which can be employed depending, for example, on the desired pH of the buffer, the desired conductivity of the buffer, the characteristics of the protein of interest, and the purification method. In some embodiments of any of the methods described herein, the methods comprise using a buffer. The buffer can be a loading buffer, an equilibration buffer, or a wash buffer. In some embodiments, one or more of the loading buffer, the equilibration buffer, and/or the wash buffer are the same. In some embodiments, the loading buffer, the equilibration buffer, and/or the wash buffer are different. In some embodiments of any of the methods described herein, the buffer comprises a salt. The loading buffer may comprise sodium chloride, sodium acetate, or a mixture thereof. In some embodiments, the loading buffer is a sodium chloride buffer. In some embodiments, the loading buffer is a sodium acetate buffer.

Load, as used herein, is the composition loaded onto a chromatography material. Loading buffer is the buffer used to load the composition comprising DsbC onto a chromatography material. The chromatography material may be equilibrated with an equilibration buffer prior to loading the composition which is to be purified. In some examples, the wash buffer is used after loading the composition onto a chromatography material and before elution of the polypeptide of interest from the solid phase.

Elution, as used herein, is the removal of the product, e.g. DsbC, from the chromatography material. Elution buffer is the buffer used to elute the polypeptide or other product of interest from a chromatography material. In many cases, an elution buffer has a different physical characteristic than the load buffer. For example, the elution buffer may have a different conductivity than load buffer or a different pH than the load buffer. In some embodiments, the elution buffer has a lower conductivity than the load buffer. In some embodiments, the elution buffer has a higher conductivity than the load buffer. In some embodiments, the elution buffer has a lower pH than the load buffer. In some embodiments, the elution buffer has a higher pH than the load buffer. In some embodiments the elution buffer has a different conductivity and a different pH than the load buffer. The elution buffer can have any combination of higher or lower conductivity and higher or lower pH.

Conductivity refers to the ability of an aqueous solution to conduct an electric current between two electrodes. In solution, the current flows by ion transport. Therefore, with an increasing amount of ions present in the aqueous solution, the solution will have a higher conductivity. The basic unit of measure for conductivity is the Siemen (or mho), mho (mS/cm), and can be measured using a conductivity meter, such as various models of Orion conductivity meters. Since electrolytic conductivity is the capacity of ions in a solution to carry electrical current, the conductivity of a solution may be altered by changing the concentration of ions therein. For example, the concentration of a buffering agent and/or the concentration of a salt (e.g. sodium chloride, sodium acetate, or potassium chloride) in the solution may be altered in order to achieve the desired conductivity. Preferably, the salt concentration of the various buffers is modified to achieve the desired conductivity.

In some embodiments of any of the methods described herein, the anion exchange load buffer has a conductivity of greater than about any of 4.0 mS/cm, 4.5 mS/cm, 5.0 mS/cm, 5.5 mS/cm, 6.0 mS/cm, 6.5 mS/cm, 7.0 mS/cm, 7.5 mS/cm, 8.0 mS/cm, 8.5 mS/cm, 9.0 mS/cm, 9.5 mS/cm, or 10 mS/cm. The conductivity may be between about any of 4 mS/cm and 17 mS/cm, 4 mS/cm and 10 mS/cm, 4 mS/cm and 7 mS/cm, 5 mS/cm and 17 mS/cm, 5 mS/cm and 10 mS/cm, or 5 mS/cm and 7 mS/cm. In some embodiments, the conductivity is about any of 4 mS/cm, 4.5 mS/cm, 5.0 mS/cm, 5.5 mS/cm, 6.0 mS/cm, 6.5 mS/cm, 7.0 mS/cm, 7.5 mS/cm, 8.0 mS/cm, 8.5 mS/cm, 9.0 mS/cm, 9.5 mS/cm, or 10 mS/cm. In one aspect, the conductivity is the conductivity of the loading buffer, the equilibration buffer, and/or the wash buffer. In some embodiments, the conductivity of one or more of the loading buffer, the equilibration buffer, and the wash buffer are the same. In some embodiments, the conductivity of the loading buffer is different from the conductivity of the wash buffer and/or equilibration buffer.

In some embodiments, the anion exchange elution buffer has a conductivity greater than the conductivity of the load buffer. In some embodiments of any of the methods described herein, the elution buffer has a conductivity of greater than about any of 5 mS/cm, 10 mS/cm, 15 mS/cm, 20 mS/cm, 25 mS/cm, 30 mS/cm, 35 mS/cm, 40 mS/cm, 45 mS/cm, 50 mS/cm, 55 mS/cm, 60 mS/cm, 65 mS/cm, 70 mS/cm, 75 mS/cm, 80 mS/cm, 85 mS/cm, 90 mS/cm, 95 mS/cm, or 100 mS/cm. In some embodiments, the conductivity of the elution buffer is altered by altering the salt concentration of the elution buffer.

In some embodiments, the HIC loading buffer has a conductivity greater than the conductivity of the elution buffer. In some embodiments of any of the methods described herein, the HIC loading buffer has a conductivity of greater than about any of 5 mS/cm, 10 mS/cm, 15 mS/cm, 20 mS/cm, 25 mS/cm, 30 mS/cm, 35 mS/cm, 40 mS/cm, 45 mS/cm, 50 mS/cm, 55 mS/cm, 60 mS/cm, 65 mS/cm, 70 mS/cm, 75 mS/cm, 80 mS/cm, 85 mS/cm, 90 mS/cm, 95 mS/cm, or 100 mS/cm. In some embodiments, the conductivity of the elution buffer is altered by altering the salt concentration of the elution buffer.

In some embodiments of any of the methods described herein, the HIC elution buffer has a conductivity of less than about any of 4.0 mS/cm, 4.5 mS/cm, 5.0 mS/cm, 5.5 mS/cm, 6.0 mS/cm, 6.5 mS/cm, 7.0 mS/cm, 7.5 mS/cm, 8.0 mS/cm, 8.5 mS/cm, 9.0 mS/cm, 9.5 mS/cm, or 10 mS/cm.

In some aspects of any of the above embodiments, the conductivity of the elution buffer changed from the load and/or wash buffer isocratically, by step gradient or by linear gradient.

In some embodiments, DsbC is eluted from the anion exchange chromatography material with a salt gradient from about 0% to about 60% 10 mM MOPS and 250 mM NaCl over 15 column volumes. In some embodiments, the salt gradient is from about 0% to about 60% 10 mM MOPS and 250 mM NaCl over 10 column volumes.

In some embodiments, DsbC is eluted from the HIC material using purified water until the DsbC elutes from the HIC material.

In some embodiments of any of the methods described herein, the anion exchange load buffer has a pH of less than about any of 10, 9, 8, 7, 6, or 5. In some embodiments of any of the methods described herein, the load buffer has a pH of greater than about any of 4, 5, 6, 7, 8, or 9. In some embodiments, the pH of one or more of the loading buffer, the equilibration buffer, and/or the wash buffer are the same. In some embodiments, the pH of the loading buffer is different from the pH of the equilibration buffer and/or the wash buffer.

In some embodiments, the elution buffer has a pH less than the pH of the load buffer. In some embodiments of any of the methods described herein, the elution buffer has a pH of less than about any of 8, 7, 6, 5, 4, 3 or 2. The pH of the elution buffer may be between about any of 4 and 9, 4 and 8, 4 and 7, 4 and 6, 4 and 5, 5 and 9, 5 and 8, 5 and 7, 5 and 6, 6 and 9, 6 and 8, 6 and 7. In some embodiments, the pH of the elution buffer is about any of 4.0, 4.5, 5.0, 5.5, 6.0, 6.5, 7/0, 7.5, 8.0, 8.5 or 9.0. In some embodiments, the composition comprising DsbC is loaded onto the anion exchange material in loading buffer at pH 8 and eluted from the anion exchange material in elution buffer at pH about 7.0 or 7.1.

In some embodiments of any of the methods described herein, the HIC load buffer has a pH of less than about any of 6, 7, or 8. In some embodiments of any of the methods described herein, the load buffer has a pH of greater than about any of 6, 7, or 8. In some embodiments, the pH of one or more of the loading buffer, the equilibration buffer, and/or the wash buffer are the same. In some embodiments, the pH of the loading buffer is different from the pH of the equilibration buffer and/or the wash buffer.

In some embodiments, size exclusion chromatography is used in a flow-through mode. In some embodiments, the buffer used for size exclusion chromatography is PBS pH 7.0±0.4.

In some embodiments of any of the methods described herein, the flow rate is less than about any of 50 CV/hr, 40 CV/hr, or 30 CV/hr. The flow rate may be between about any of 5 CV/hr and 50 CV/hr, 10 CV/hr and 40 CV/hr, or 18 CV/hr and 36 CV/hr. In some embodiments, the flow rate is about any of 9 CV/hr, 18 CV/hr, 25 CV/hr, 30 CV/hr, 36 CV/hr, or 40 CV/hr. In some embodiments of any of the methods described herein, the flow rate is less than about any of 200 cm/hr, 150 cm/hr, 100 cm/hr, 75 cm/hr, or 50 cm/hr. The flow rate may be between about any of 25 cm/hr and 200 cm/hr, 25 cm/hr and 175 cm/hr, 25 cm/hr and 150 cm/hr, 25 cm/hr and 100 cm/hr, 50 cm/hr and 100 cm/hr, or 65 cm/hr and 85 cm/hr. In some embodiments, the flow rate is about more than about 0.1 mL/min, 0.25 mL/min, 0.5 mL/min, 0.75 mL/min, 1 mL/min, 2 mL/min, 3 mL/min, 4 mL/min, 5 mL/min, 6 mL/min, 7 mL/min, 8 mL/min, 9 mL/min, 10 mL/min, 11 mL/min, 12 mL/min, 13 mL/min, 14 mL/min, 15 mL/min, 20 mL/min, 25 mL/min, and 50 mL/min. In some embodiments, the flow rate is between about 0.1 mL/min and 1 mL/min, 1 mL/min and 5 mL/min, 1 mL/min and 10 mL/min, 5 mL/min and 10 mL/min, 10 mL/min and 15 mL/min, 10 mL/min and 25 mL/min, and 15 mL/min and 25 mL/min. In some embodiments, the flow rate for anion exchange chromatography of DsbC is about 13.3 ml/min. In some embodiments, the flow rate for hydrophobic interaction chromatography of DsbC is about 13.2 ml/min. In some embodiments, the flow rate for size exclusion chromatography of DsbC is about 1 ml/min.

Bed height is the height of chromatography material used. In some embodiments of any of the method described herein, the bed height is greater than about any of 3 cm, 10 cm, 15 cm, 20 cm, 25 cm, 30 cm, 35 cm, 40 cm, 45 cm, 50 cm, 60 cm, 70 cm, 80 cm, 90 cm or 100 cm. The bed height may be between about any of 3 cm and 50 cm, 5 cm and 35 cm, 3 cm and 35 cm, or 5 cm and 50 cm. In some embodiments, bed height is determined based on the amount of polypeptide or impurities in the load.

In some embodiments, the chromatography is in a column of vessel with a volume of greater than about 1 mL, 2 mL, 3 mL, 4 mL, 5 mL, 6 mL, 7 mL, 8 mL, 9 mL, 10 mL, 15 mL, 20 mL, 25 mL, 30 mL, 40 mL, 50 mL, 75 mL, 100 mL, or 200 mL.

In some embodiments of the invention, fractions are collected from the chromatography. In some embodiments, fractions collected are greater than about 0.01 CV, 0.02 CV, 0.03 CV, 0.04 CV, 0.05 CV, 0.06 CV, 0.07 CV, 0.08 CV, 0.09 CV, 0.1 CV, 0.2 CV, 0.3 CV, 0.4 CV, 0.5 CV, 0.6 CV, 0.7 CV, 0.8 CV, 0.9 CV, 1.0 CV, 2.0 CV, 3.0 CV, 4.0 CV, 5.0 CV, 6.0 CV, 7.0 CV, 8.0 CV, 9.0 CV, or 10.0 CV.

In some embodiments, fractions containing the product, e.g. polypeptide, are pooled. In some embodiments, fractions containing the polypeptide from the load fractions and from the elution fractions are pooled. The amount of polypeptide in a fraction can be determined by one skilled in the art; for example, the amount of polypeptide in a fraction can be determined by UV spectroscopy. In some embodiments, fractions containing detectable polypeptide fragment are pooled. In some embodiments, the presence and purity of DsbC in a fraction is determined by size exclusion chromatography.

Exemplary Embodiment

In some embodiments, the invention provides the following exemplary but nonlimiting method for producing an ultrapure preparation of DsbC. DsbC is expressed in *E. coli*. The cell paste is suspended (50 g cell paste/1 L) in 10 mM MOPS pH 7.1 and mixed until the suspension is homogenous. Cell lysis is performed using a Microfluidizer 110F with 3 passes at house pressure (7000 psi). The homogenate is conditioned to 0.1% PEI (using a 10% PEI stock solution) and mixed for 30 min at ambient temperature (~21° C.). The suspension is centrifuged in a Sorval RC-5B+ centrifuge using a "GSA" rotor at 8500 rpm for 30 min. The centrate is collected and filtered through a 0.22 um Durapore filter.

(a) DEAE Sepharose

The clarified centrate (conditioned with 1.5 M Tris base to pH 8.0) is loaded to a column containing DEAE Sepharose® Fast Flow (GE Healthcare) in bind and elute mode. The column has the following properties: column was 28.4 cm×2.6 cm diameter, volume 151 mL, protein capacity ≤50 mg/mL resin. The column is pre-equilibrated with 3 CV 250 mM MOPS pH 7.1; cond. 6.2 mS/cm and equilibrated with 10 mM MOPS, pH 7.1; cond. 0.3 mS/cm. At the end of loading, the column is washed with 12 CV of equilibration buffer. The DsbC is eluted using a 15 CV gradient of 0-60% buffer B. Elution is a linear gradient of 0-60% buffer B into elution buffer over 15 CV. Fractions are analyzed by SDS-PAGE.

(b) Phenyl Sepharose

The pooled DEAE fractions are then applied to Phenyl Sepharose® chromatography in bind and elute mode. The column has the following properties: column was 20 cm×2.6 cm diameter, volume 106 mL, protein capacity ≤20 mg/mL resin. The column is equilibrated with 0.6 M sodium sulfate, 50 mM sodium phosphate, pH 7.0. The conditioned DEAE pool comprising DsbC is loaded onto the Phenyl Sepharose column following dilution of 1:1 with 1.2 M sodium sulfate, 1:20 with 1 M sodium phosphate and adjusted to pH 7.0, ~68 mS/cm prior to loading. The column is then washed with 7 CV 0.6 M sodium sulfate, 50 mM sodium phosphate, pH 7.0 and then 7 CV 0.6 M sodium sulfate, 50 mM sodium phosphate, pH 7.0. DsbC is eluted from the column with purified water. Fractions are collected and analyzed by SDS-PAGE analysis of the column fractions.

(c) Superdex

The pooled Phenyl Sepharose fractions are then subjected to size exclusion chromatography, using Superdex 75. This step is used to remove any residual high MW and low MW species and to formulate DsbC. Superdex 75 has fractionation range (5 kDa to 70 kDa) is better suited to a smaller protein (~24 kDa) like DsbC. The column is a Superdex 75 and has the following properties: column was 60 cm×2.6 cm diameter, volume 320 mL, load volume ≤16 mL. The HIC pool (fractions 7-11) is concentrated to a volume of ≤16 mL (≤5% of the SEC CV) using centrifugal filters. The units are centrifuged at 4000 rpm using a clinical centrifuge for 20 min intervals until the target volume is reached. The Superdex 75 size exclusion column is equilibrated with 3 CV PBS, pH 7.0±0.4. The Phenyl sepharose fraction is loaded on the column and eluted with PBS, pH 7.0±0.4 at a flow rate of 1 mL/min.

C. Methods to Determine the Purity of DsbA and DsbC

Methods to determine the purity of preparations of DsbA and DsbC are known in the art. In some embodiments, the purity DsbA or DsbC in a preparation is determined by size exclusion chromatography (SEC). In some embodiments, the purity DsbA or DsbC in a preparation is determined by high performance liquid chromatography size exclusion chromatography (HPLC SEC). In some embodiments, the purity DsbA or DsbC in a preparation is determined by sodium dodecyl sulfate polyacrylamide gel electrophoresis (SDS-PAGE). In some embodiments, protein on an SDS PAGE gel is identified using a fluorescent protein stain. In some embodiments, the fluorescent protein stain is a Sypro®Ruby stain. In some embodiments, proteins on the SDS-PAGE are visualized using Heukeshoven Silver staining. In other embodiments, the identity of the DsbA or DsbC molecule is confirmed using characterization assays including but not limited to N-terminal sequence analysis, Peptide Mass Fingerprinting (PMF), intact/reduced Mass by CHIP TOF, and western blot analysis.

In some embodiments, the invention provides ultrapure preparations of DsbA. In some embodiments, the invention provides a preparation of DsbA wherein monomeric DsbA makes up at least about any of 95%, 96%, 97%, 98%, 99%, or 99.5% of the preparation. In some embodiment, the monomeric DsbA is about any of 95%, 96%, 97%, 98%, 99%, and/or 99.5% of the preparation. In some embodiments, the preparation comprises less than about any of 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, or 0.01%, of impurities. Impurities may include, but are not limited to host cell proteins such as E. coli host cell proteins, nucleic acids, viruses, cell culture components such as cell culture media components as well as aggregates of DsbA or fragments of DsbA (e.g., non-functional fragments of DsbA). In some embodiments, the preparation comprises less than about any of 2%, 1.5%, or 1% low molecular weight species. In some embodiments, the preparation comprises less than about 1%, 0.5%, or 0.1% high molecular weight species. In some embodiments, the high molecular weight species are undetectable. In some embodiments, the presence of monomeric DsbA, low molecular weight species, and/or high molecular weight species are detected by SEC.

In some embodiments, the invention provides ultrapure preparations of DsbC. In some embodiments, the invention provides a preparation of DsbC wherein monomeric DsbC makes up at least about any of 95%, 96%, 97%, 98%, 99%, or 99.5% of the preparation. In some embodiment, the monomeric DsbC is about any of 95%, 96%, 97%, 98%, 99%, and/or 99.5% of the preparation. In some embodiments, the preparation comprises less than about any of 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, or 0.01%, of impurities. Impurities may include, but are not limited to host cell proteins such as E. coli host cell proteins, nucleic acids, viruses, cell culture components such as cell culture media components as well as aggregates of DsbC or fragments of DsbC (e.g., non-functional fragments of DsbC). In some embodiments, the preparation comprises less than about any of 1%, 0.5%, or 0.1% low molecular weight species. In some embodiments, the preparation comprises less than about 1%, 0.5%, or 0.1% high molecular weight species. In some embodiments, the presence of monomeric DsbC, low molecular weight species, and/or high molecular weight species are detected by SEC.

Methods of measuring DNA such as host cell DNA are known in the art and described in the examples section. In some embodiments of any of the methods described herein, the amount of DNA is reduced by greater than about any of 10%, 20%, 30%, 40%, 50%, 60%, 70%, 80%, or 90%. The amount of DNA may be reduced by between about any of 10% and 99%, 30% and 95%, 30% and 99%, 50% and 95%, 50% and 99%, 75% and 99%, or 85% and 99%. The amount of DNA may be reduced by about any of 10%, 20%, 30%, 40%, 50%, 60%, 70%, 80%, 90%, 95%, or 99%. In some embodiments, the reduction is determined by comparing the amount of DNA in the composition recovered from a purification step(s) to the amount of DNA in the composition before the purification step(s).

Cell culture media component refers to a component present in a cell culture media. A cell culture media may be a cell culture media at the time of harvesting cells. In some embodiments, the cell culture media component is gentamicin. The amount of gentamicin may be measured by ELISA. In some embodiments of any of the methods described herein, the amount of cell culture media component is reduced by greater than about any of 10%, 20%, 30%, 40%, 50%, 60%, 70%, 80%, or 90%. The amount of cell culture media component may be reduced by between about any of 10% and 99%, 30% and 95%, 30% and 99%, 50% and 95%, 50% and 99%, 75% and 99%, or 85% and 99%. In some embodiments, the amount of cell culture media component is reduced by about any of 10%, 20%, 30%, 40%, 50%, 60%, 70%, 80%, 90%, 95%, or 98%. In some embodiments, the reduction is determined by comparing the amount of cell culture media component in the composition recovered from a purification step(s) to the amount of cell culture media component in the composition before the purification step(s).

III. Polypeptides-DsbA and DsbC

The invention provides methods to generate ultrapure preparations of DsbA and DsbC. The term "Dsb" proteins refer to bacterial disulfide oxidoreductases. DsbA forms intrachain disulfide bonds as peptides emerge into the cell's periplasm and DsbC serves as a disulfide bond isomerase during oxidative protein-folding in cell's periplasm. In some embodiments, DsbA and DsbC are derived from bacteria. In some embodiments, the DsbA and DsbC polypeptides are *E. coli* DsbA and DsbC polypeptides. In other embodiments, the DsbA and DsbC polypeptides are derived from any species of *Enterobacteria, Actinetobacter, Azoarcus, Salmonella, Buchnera, Xylella, Xanthmonas, Campylobacter, Shigella, Pseudomonas, Yersina, Erwinia,* and *Neisseria*. In some embodiments, the DsbA polypeptide comprises the amino acid sequence of SEQ ID NO:1. In some embodiments, the DsbA polypeptide comprises an amino acid sequence that has at least about any of 70%, 75%, 80%, 85%, 90%, 95%, or 99% identity to the amino acid sequence of SEQ ID NO:1. In some embodiments, the DsbC polypeptide comprises the amino acid sequence of SEQ ID NO:3. In some embodiments, the DsbC polypeptide comprises an amino acid sequence that has at least about any of 70%, 75%, 80%, 85%, 90%, 95%, or 99% identity to the amino acid sequence of SEQ ID NO:3.

The DsbA and DsbC polypeptides to be purified using the methods described herein is generally produced using recombinant techniques. Methods for producing recombinant polypeptides in bacteria are known in the art. When using recombinant techniques, the polypeptides can be produced intracellularly, in the periplasmic space, or directly secreted into the medium. In some embodiments, nucleic acid encoding DsbA or DsbC is introduced to the host cell for overexpression of the polypeptide. In some embodiments, the nucleic acid encoding DsbA or DsbC is expressed from an expression vector; e.g., a plasmid. In some embodiments, the nucleic acid encoding the DsbA polypeptide comprises the nucleic acid sequence of SEQ ID NO:2. In some embodiments, the nucleic acid encoding DsbA comprises a nucleic acid sequence that has at least about any of 70%, 75%, 80%, 85%, 90%, 95%, or 99% identity to the nucleic acid sequence of SEQ ID NO:2. In some embodiments, the nucleic acid encoding DsbC comprises the nucleic acid sequence of SEQ ID NO:4. In some embodiments, the nucleic acid encoding DsbC comprises a nucleic acid sequence that has at least about any of 70%, 75%, 80%, 85%, 90%, 95%, or 99% identity to the nucleic acid sequence of SEQ ID NO:3.

The polypeptides may be recovered from culture medium or from host cell lysates. Cells employed in expression of the polypeptides can be disrupted by various physical or chemical means, such as freeze-thaw cycling, sonication, mechanical disruption, or cell lysing agents. If the polypeptide is produced intracellularly, as a first step, the particulate debris, either host cells or lysed fragments, are removed, for example, by centrifugation or ultrafiltration. Carter et al., *Bio/Technology* 10: 163-167 (1992) describe a procedure for isolating polypeptides which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the polypeptide is secreted into the medium, supernatants from such expression systems are generally first concentrated using a commercially available polypeptide concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

IV. Polypeptides for which DsbA and/or DsbC May be Used in Production

Examples of polypeptides that may be produced in bacteria (e.g. *E coli*) where protein folding and assembly may be aided by the overexpression of DsbA and/or DsbC include but are not limited to immunoglobulins, immunoadhesins, antibodies, enzymes, hormones, fusion proteins, Fc-containing proteins, immunoconjugates, cytokines and interleukins Examples of polypeptide include, but are not limited to, mammalian proteins, such as, e.g., renin; a hormone; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; an enzyme; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-b; platelet-derived growth factor (PDGF); fibroblast growth factor such as aFGF and bFGF; epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins (IGFBPs); a cytokine; CD proteins such as CD3, CD4, CD8, CD19 and CD20; erythropoietin; osteoinductive factors; immunotoxins; a fusion polypeptide, i.e. a polypeptide comprised on two or more heterologous polypeptides or fragments thereof and encoded by a recombinant nucleic acid; an Fc-containing polypeptide, for example, a fusion protein comprising an immunoglobulin Fc region, or fragment thereof, fused to a second polypeptide; an immunoconjugate; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the AIDS envelope; transport proteins; homing receptors;

addressins; regulatory proteins; integrins such as CD11a, CD11b, CD11c, CD18, an ICAM, VLA-4 and VCAM; a tumor associated antigen such as CA125 (ovarian cancer antigen) or HER2, HER3 or HER4 receptor; immunoadhesins; and fragments and/or variants of any of the above-listed proteins as well as antibodies, including antibody fragments, binding to a protein, including, for example, any of the above-listed proteins.

In some embodiments, the polypeptide preparation for use in any of the assay methods described herein contains an antibody of interest, i.e. the recombinant polypeptide produced by a host cell is an antibody.

Molecular targets for such antibodies include CD proteins and their ligands, such as, but not limited to: (i) CD3, CD4, CD8, CD19, CD11a, CD20, CD22, CD34, CD40, CD79? (CD79a), and CD79? (CD79b); (ii) members of the ErbB receptor family such as the EGF receptor, HER2, HER3 or HER4 receptor; (iii) cell adhesion molecules such as LFA-1, Mac1, p150,95, VLA-4, ICAM-1, VCAM and αv/β3 integrin, including either alpha or beta subunits thereof (e.g., anti-CD11a, anti-CD18 or anti-CD11b antibodies); (iv) growth factors such as VEGF; IgE; blood group antigens; flk2/flt3 receptor; obesity (OB) receptor; mpl receptor; CTLA-4; protein C, BR3, c-met, tissue factor, β7 etc; and (v) cell surface and transmembrane tumor-associated antigens (TAA), such as those described in U.S. Pat. No. 7,521,541.

Other exemplary antibodies include those selected from, and without limitation, anti-estrogen receptor antibody, anti-progesterone receptor antibody, anti-p53 antibody, anti-HER-2/neu antibody, anti-EGFR antibody, anti-cathepsin D antibody, anti-Bcl-2 antibody, anti-E-cadherin antibody, anti-CA125 antibody, anti-CA15-3 antibody, anti-CA19-9 antibody, anti-c-erbB-2 antibody, anti-P-glycoprotein antibody, anti-CEA antibody, anti-retinoblastoma protein antibody, anti-ras oncoprotein antibody, anti-Lewis X antibody, anti-Ki-67 antibody, anti-PCNA antibody, anti-CD3 antibody, anti-CD4 antibody, anti-CD5 antibody, anti-CD7 antibody, anti-CD8 antibody, anti-CD9/p24 antibody, anti-CD10 antibody, anti-CD11a antibody, anti-CD11c antibody, anti-CD13 antibody, anti-CD14 antibody, anti-CD15 antibody, anti-CD19 antibody, anti-CD20 antibody, anti-CD22 antibody, anti-CD23 antibody, anti-CD30 antibody, anti-CD31 antibody, anti-CD33 antibody, anti-CD34 antibody, anti-CD35 antibody, anti-CD38 antibody, anti-CD41 antibody, anti-LCA/CD45 antibody, anti-CD45RO antibody, anti-CD45RA antibody, anti-CD39 antibody, anti-CD100 antibody, anti-CD95/Fas antibody, anti-CD99 antibody, anti-CD106 antibody, anti-ubiquitin antibody, anti-CD71 antibody, anti-c-myc antibody, anti-cytokeratins antibody, anti-vimentins antibody, anti-HPV proteins antibody, anti-kappa light chains antibody, anti-lambda light chains antibody, anti-melanosomes antibody, anti-prostate specific antigen antibody, anti-S-100 antibody, anti-tau antigen antibody, anti-fibrin antibody, anti-keratins antibody and anti-Tn-antigen antibody.

Polyclonal Antibodies

In some embodiments, antibodies are polyclonal antibodies. Polyclonal antibodies are preferably raised in animals by multiple subcutaneous (sc) or intraperitoneal (ip) injections of the relevant antigen and an adjuvant. It may be useful to conjugate the relevant antigen to a polypeptide that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R1N=C=NR$, where R and R1 are different alkyl groups.

Animals are immunized against the antigen, immunogenic conjugates, or derivatives by combining, e.g., 100 μg or 5 μg of the polypeptide or conjugate (for rabbits or mice, respectively) with 3 volumes of Freund's complete adjuvant and injecting the solution intradermally at multiple sites. One month later the animals are boosted with ⅕ to 1/10 the original amount of peptide or conjugate in Freund's complete adjuvant by subcutaneous injection at multiple sites. Seven to 14 days later the animals are bled and the serum is assayed for antibody titer. Animals are boosted until the titer plateaus. In some embodiments, the animal is boosted with the conjugate of the same antigen, but conjugated to a different polypeptide and/or through a different cross-linking reagent. Conjugates also can be made in recombinant cell culture as polypeptide fusions. Also, aggregating agents such as alum are suitably used to enhance the immune response.

Monoclonal Antibodies

In some embodiments, antibodies are monoclonal antibodies. Monoclonal antibodies are obtained from a population of substantially homogeneous antibodies, i.e., the individual antibodies comprising the population are identical and/or bind the same epitope except for possible variants that arise during production of the monoclonal antibody, such variants generally being present in minor amounts. Thus, the modifier "monoclonal" indicates the character of the antibody as not being a mixture of discrete or polyclonal antibodies.

For example, the monoclonal antibodies may be made using the hybridoma method first described by Kohler et al., *Nature* 256:495 (1975), or may be made by recombinant DNA methods (U.S. Pat. No. 4,816,567).

In the hybridoma method, a mouse or other appropriate host animal, is immunized as herein described to elicit lymphocytes that produce or are capable of producing antibodies that will specifically bind to the polypeptide used for immunization. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

In some embodiments, the myeloma cells are those that fuse efficiently, support stable high-level production of antibody by the selected antibody-producing cells, and are sensitive to a medium such as HAT medium. Among these, in some embodiments, the myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.* 133:3001 (1984); Brodeur et al., Monoclonal Antibody Production Techniques and Applications pp. 51-63 (Marcel Dekker, Inc., New York, 1987)).

Culture medium in which hybridoma cells are growing is assayed for production of monoclonal antibodies directed against the antigen. In some embodiments, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson et al., *Anal. Biochem.* 107:220 (1980).

After hybridoma cells are identified that produce antibodies of the desired specificity, affinity, and/or activity, the clones may be subcloned by limiting dilution procedures and grown by standard methods (Goding, Monoclonal Antibodies: Principles and Practice pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, polypeptide A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of murine antibodies). In some embodiments, the hybridoma cells serve as a source of such DNA. Once isolated, the DNA may be placed into expression vectors, which are then transfected into host cells such as *E. coli* cells, simian COS cells, human embryonic kidney (HEK) 293 cells, Chinese Hamster Ovary (CHO) cells, or myeloma cells that do not otherwise produce immunoglobulin polypeptide, to obtain the synthesis of monoclonal antibodies in the recombinant host cells. Review articles on recombinant expression in bacteria of DNA encoding the antibody include Skerra et al., *Curr. Opinion in Immunol.* 5:256-262 (1993) and Plückthun, *Immunol. Revs.*, 130:151-188 (1992).

In a further embodiment, antibodies or antibody fragments can be isolated from antibody phage libraries generated using the techniques described in McCafferty et al., *Nature* 348:552-554 (1990). Clackson et al., *Nature* 352:624-628 (1991) and Marks et al., *J. Mol. Biol.* 222:581-597 (1991) describe the isolation of murine and human antibodies, respectively, using phage libraries. Subsequent publications describe the production of high affinity (nM range) human antibodies by chain shuffling (Marks et al., *Bio/Technology* 10:779-783 (1992)), as well as combinatorial infection and in vivo recombination as a strategy for constructing very large phage libraries (Waterhouse et al., *Nuc. Acids. Res.* 21:2265-2266 (1993)). Thus, these techniques are viable alternatives to traditional monoclonal antibody hybridoma techniques for isolation of monoclonal antibodies.

The DNA also may be modified, for example, by substituting the coding sequence for human heavy- and light chain constant domains in place of the homologous murine sequences (U.S. Pat. No. 4,816,567; Morrison et al., *Proc. Natl Acad. Sci. USA* 81:6851 (1984)), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

In some embodiments of any of the methods described herein, the antibody is IgA, IgD, IgE, IgG, or IgM. In some embodiments, the antibody is an IgG monoclonal antibody.

Antibody Fragments

In some embodiments, an antibody is an antibody fragment. Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992) and Brennan et al., *Science* 229:81 (1985)). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form F(ab')2 fragments (Carter et al., *Bio/Technology* 10:163-167 (1992)). According to another approach, F(ab')2 fragments can be isolated directly from recombinant host cell culture. Other techniques for the production of antibody fragments will be apparent to the skilled practitioner. In other embodiments, the antibody of choice is a single chain Fv fragment (scFv). See WO 93/16185; U.S. Pat. Nos. 5,571,894; and 5,587,458. The antibody fragment may also be a "linear antibody," e.g., as described in U.S. Pat. No. 5,641,870 for example. Such linear antibody fragments may be monospecific or bispecific.

In some embodiments, fragments of the antibodies described herein are provided. In some embodiments, the antibody fragment is an antigen binding fragment. In some embodiments, the antigen binding fragment is selected from the group consisting of a Fab fragment, a Fab' fragment, a F(ab')2 fragment, a scFv, a Fv, and a diabody.

Polypeptide Variants and Modifications

In certain embodiments, amino acid sequence variants of the proteins herein are contemplated. For example, it may be desirable to improve the binding affinity and/or other biological properties of the protein. Amino acid sequence variants of a protein may be prepared by introducing appropriate modifications into the nucleotide sequence encoding the protein, or by peptide synthesis. Such modifications include, for example, deletions from, and/or insertions into and/or substitutions of residues within the amino acid sequences of the protein. Any combination of deletion, insertion, and substitution can be made to arrive at the final construct, provided that the final construct possesses the desired characteristics.

Variant Polypeptides

"Polypeptide variant" means a polypeptide, for example, an active polypeptide, as defined herein having at least about 80% amino acid sequence identity with a full-length native sequence of the polypeptide, a polypeptide sequence lacking the signal peptide, an extracellular domain of a polypeptide, with or without the signal peptide. Such polypeptide variants include, for instance, polypeptides wherein one or more amino acid residues are added, or deleted, at the N or C-terminus of the full-length native amino acid sequence. Ordinarily, a polypeptide variant will have at least about 80% amino acid sequence identity, alternatively at least about any of 85%, 90%, 95%, 96%, 97%, 98%, or 99% amino acid sequence identity, to a full-length native sequence polypeptide sequence, a polypeptide sequence lacking the signal peptide, an extracellular domain of a polypeptide, with or without the signal peptide. Optionally, variant polypeptides will have no more than one conservative amino acid substitution as compared to the native polypeptide sequence, alternatively no more than about any of 2, 3, 4, 5, 6, 7, 8, 9, or 10 conservative amino acid substitution as compared to the native polypeptide sequence.

The variant polypeptide may be truncated at the N-terminus or C-terminus, or may lack internal residues, for example, when compared with a full length native polypeptide. Certain variant polypeptides may lack amino acid residues that are not essential for a desired biological activity. These variant polypeptides with truncations, deletions, and insertions may be prepared by any of a number of conventional techniques. Desired variant polypeptides may be chemically synthesized. Another suitable technique involves isolating and amplifying a nucleic acid fragment encoding a desired variant polypeptide, by polymerase chain reaction (PCR). Oligonucleotides that define the desired termini of the nucleic acid fragment are employed at the 5' and 3' primers in the PCR. Preferably, variant polypeptides share at least one biological and/or immunological activity with the native polypeptide disclosed herein.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of the antibody molecule include the fusion to the N- or C-terminus of the antibody to an enzyme or a polypeptide which increases the serum half-life of the antibody.

For example, it may be desirable to improve the binding affinity and/or other biological properties of the polypeptide Amino acid sequence variants of the polypeptide are prepared by introducing appropriate nucleotide changes into the antibody nucleic acid, or by peptide synthesis. Such modifications include, for example, deletions from, and/or insertions into and/or substitutions of, residues within the amino acid sequences of the polypeptide. Any combination of deletion, insertion, and substitution is made to arrive at the final construct, provided that the final construct possesses the desired characteristics. The amino acid changes also may alter post-translational processes of the polypeptide (e.g., antibody), such as changing the number or position of glycosylation sites.

Guidance in determining which amino acid residue may be inserted, substituted or deleted without adversely affecting the desired activity may be found by comparing the sequence of the polypeptide with that of homologous known polypeptide molecules and minimizing the number of amino acid sequence changes made in regions of high homology.

A useful method for identification of certain residues or regions of the polypeptide (e.g., antibody) that are preferred locations for mutagenesis is called "alanine scanning mutagenesis" as described by Cunningham and Wells, Science 244:1081-1085 (1989). Here, a residue or group of target residues are identified (e.g., charged residues such as Arg, Asp, His, Lys, and Glu) and replaced by a neutral or negatively charged amino acid (most preferably Alanine or Polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed antibody variants are screened for the desired activity.

Another type of variant is an amino acid substitution variant. These variants have at least one amino acid residue in the antibody molecule replaced by a different residue. The sites of greatest interest for substitutional mutagenesis include the hypervariable regions, but FR alterations are also contemplated. If such substitutions result in a change in biological activity, then more substantial changes, denominated "exemplary substitutions" in the Table 1, or as further described below in reference to amino acid classes, may be introduced and the products screened.

TABLE 1

| Original Residue | Exemplary Substitutions | Conservative Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in the biological properties of the polypeptide are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain Amino acids may be grouped according to similarities in the properties of their side chains (in A. L. Lehninger, Biochemistry second ed., pp. 73-75, Worth Publishers, New York (1975)):

(1) non-polar: Ala (A), Val (V), Leu (L), Ile (I), Pro (P), Phe (F), Trp (W), Met (M)
(2) uncharged polar: Gly (G), Ser (S), Thr (T), Cys (C), Tyr (Y), Asn (N), Gln (Q)
(3) acidic: Asp (D), Glu (E)
(4) basic: Lys (K), Arg (R), His(H)

Alternatively, naturally occurring residues may be divided into groups based on common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

Any cysteine residue not involved in maintaining the proper conformation of the antibody also may be substituted, generally with serine, to improve the oxidative stability of the molecule and prevent aberrant crosslinking Conversely, cysteine bond(s) may be added to the polypeptide to improve its stability (particularly where the antibody is an antibody fragment such as an Fv fragment).

One example of substitutional variant involves substituting one or more hypervariable region residues of a parent antibody (e.g., a humanized antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and target. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the polypeptide alters the original glycosylation pattern of the antibody. The polypeptide may comprise non-amino acid moieties. For example, the polypeptide may be glycosylated. Such glycosylation may occur naturally during expression of the polypeptide in the host cell or host organism, or may be a deliberate modification arising from human intervention. By altering is meant deleting one or more carbohydrate moieties found in the polypeptide, and/or adding one or more glycosylation sites that are not present in the polypeptide.

Glycosylation of polypeptide is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the polypeptide is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Removal of carbohydrate moieties present on the polypeptide may be accomplished chemically or enzymatically or by mutational substitution of codons encoding for amino acid residues that serve as targets for glycosylation. Enzymatic cleavage of carbohydrate moieties on polypeptides can be achieved by the use of a variety of endo- and exo-glycosidases.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the γ-amino groups of lysine, arginine, and histidine side chains, acetylation of the N-terminal amine, and amidation of any C-terminal carboxyl group.

Chimeric Polypeptides

The polypeptide described herein may be modified in a way to form chimeric molecules comprising the polypeptide fused to another, heterologous polypeptide or amino acid sequence. In some embodiments, a chimeric molecule comprises a fusion of the polypeptide with a tag polypeptide which provides an epitope to which an anti-tag antibody can selectively bind. The epitope tag is generally placed at the amino- or carboxyl-terminus of the polypeptide. The presence of such epitope-tagged forms of the polypeptide can be detected using an antibody against the tag polypeptide. Also, provision of the epitope tag enables the polypeptide to be readily purified by affinity purification using an anti-tag antibody or another type of affinity matrix that binds to the epitope tag.

Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for c-met and the other is for any other antigen. In certain embodiments, bispecific antibodies may bind to two different epitopes of c-met. Bispecific antibodies may also be used to localize cytotoxic agents to cells which express c-met. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983), WO 93/08829, and Traunecker et al., *EMBO J.* 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science,* 229: 81 (1985)); using leucine zippers to produce bi-specific antibodies (see, e.g., Kostelny et al., *J. Immunol.,* 148(5):1547-1553 (1992)); using "diabody" technology for making bispecific antibody fragments (see, e.g., Hollinger et al., *Proc. Natl. Acad. Sci. USA,* 90:6444-6448 (1993)); and using single-chain Fv (sFv) dimers (see, e.g. Gruber et al., *J. Immunol.,* 152:5368 (1994)); and preparing trispecific antibodies as described, e.g., in Tutt et al. *J. Immunol.* 147: 60 (1991).

Engineered antibodies with three or more functional antigen binding sites, including "Octopus antibodies," are also included herein (see, e.g. US 2006/0025576A1).

The antibody or fragment herein also includes a "Dual Acting FAb" or "DAF" comprising an antigen binding site that binds to c-met as well as another, different antigen, such as EGFR (see, US 2008/0069820, for example).

Methods for making bispecific antibodies are known in the art. Traditionally, the recombinant production of bispecific antibodies is based on the co-expression of two immunoglobulin heavy chain-light chain pairs, where the two heavy chains have different specificities (Milstein and Cuello, Nature, 305: 537 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low Similar procedures are disclosed in WO 93/08829 published May 13, 1993, and in Traunecker et al., EMBO J., 10: 3655 (1991).

According to a different and more preferred approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1), containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., Methods in Enzymology, 121:210 (1986).

According to another approach, the interface between a pair of antibody molecules can be engineered to maximize the percentage of heterodimers which are recovered from recombinant cell culture. The preferred interface comprises at least a part of the CH3 domain of an antibody constant domain. In this method, one or more small amino acid side chains from the interface of the first antibody molecule are replaced with larger side chains (e.g., tyrosine or tryptophan) (knobs or protuberances). Compensatory "cavities" (holes) of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers. Knobs and holes are further described herein.

Knobs in Holes

The use of knobs into holes as a method of producing multispecific antibodies and/or one-armed antibodies and/or immunoadhesins is well known in the art. See U.S. Pat. No. 5,731,168 granted 24 Mar. 1998 assigned to Genentech, PCT Pub. No. WO2009089004 published 16 Jul. 2009 and assigned to Amgen, and US Pat. Pub. No. 20090182127 published 16 Jul. 2009 and assigned to Novo Nordisk A/S. See also Marvin and Zhu, Acta Pharmacologica Sincia (2005) 26(6):649-658 and Kontermann (2005) Acta Pharacol. Sin., 26:1-9. A brief discussion is provided here.

A "protuberance" refers to at least one amino acid side chain which projects from the interface of a first polypeptide and is therefore positionable in a compensatory cavity in the adjacent interface (i.e. the interface of a second polypeptide) so as to stabilize the heteromultimer, and thereby favor heteromultimer formation over homomultimer formation, for example. The protuberance may exist in the original interface or may be introduced synthetically (e.g. by altering nucleic acid encoding the interface). Normally, nucleic acid encoding the interface of the first polypeptide is altered to encode the protuberance. To achieve this, the nucleic acid encoding at least one "original" amino acid residue in the interface of the first polypeptide is replaced with nucleic acid encoding at least one "import" amino acid residue which has a larger side chain volume than the original amino acid residue. It will be appreciated that there can be more than one original and corresponding import residue. The upper limit for the number of original residues which are replaced is the total number of residues in the interface of the first polypeptide. The side chain volumes of the various amino residues are shown in the following table.

TABLE 2

Properties of Amino Acids

| Amino Acid | One-Letter Abbreviation | MASS$^a$ (daltons) | VOLUME$^b$ (Angstrom$^3$) | Accessible Surface Area$^c$ (Angstrom$^2$) |
|---|---|---|---|---|
| Alanine (Ala) | A | 71.08 | 88.6 | 115 |
| Arginine (Arg) | R | 156.20 | 173.4 | 225 |
| Asparagine (Asn) | N | 114.11 | 117.7 | 160 |
| Aspartic acid (Asp) | D | 115.09 | 111.1 | 150 |
| Cysteine (Cys) | C | 103.14 | 108.5 | 135 |
| Glutamine (Gln) | Q | 128.14 | 143.9 | 180 |
| Glutamic acid (Glu) | E | 129.12 | 138.4 | 190 |
| Glycine (Gly) | G | 57.06 | 60.1 | 75 |
| Histidine (His) | H | 137.15 | 153.2 | 195 |
| Isoleucine (Ile) | I | 113.17 | 166.7 | 175 |
| Leucine (Leu) | L | 113.17 | 166.7 | 170 |
| Lysine (Lys) | K | 128.18 | 168.6 | 200 |
| Methionine (Met) | M | 131.21 | 162.9 | 185 |
| Phenylalinine (Phe) | F | 147.18 | 189.9 | 210 |
| Proline (Pro) | P | 97.12 | 122.7 | 145 |
| Serine (Ser) | S | 87.08 | 89.0 | 115 |
| Threonine (Thr) | T | 101.11 | 116.1 | 140 |
| Tryptophan (Trp) | W | 186.21 | 227.8 | 255 |
| Tyrosine (Tyr) | Y | 163.18 | 193.6 | 230 |
| Valine (Val) | V | 99.14 | 140.0 | 155 |

$^a$Molecular weight amino acid minus that of water. Values from Handbook of Chemistry and Physics, 43rd ed. Cleveland, Chemical Rubber Publishing Co., 1961.
$^b$Values from A. A. Zamyatnin, Prog. Biophys. Mol. Biol. 24: 107-123, 1972.
$^c$Values from C. Chothia, J. Mol. Biol. 105: 1-14, 1975. The accessible surface area is defined in FIGS. 6-20 of this reference.

The preferred import residues for the formation of a protuberance are generally naturally occurring amino acid residues and are preferably selected from arginine (R), phenylalanine (F), tyrosine (Y) and tryptophan (W). Most preferred are tryptophan and tyrosine. In one embodiment, the original residue for the formation of the protuberance has a small side chain volume, such as alanine, asparagine, aspartic acid, glycine, serine, threonine or valine. Exemplary amino acid substitutions in the CH3 domain for forming the protuberance include without limitation the T366W substitution.

A "cavity" refers to at least one amino acid side chain which is recessed from the interface of a second polypeptide and therefore accommodates a corresponding protuberance on the adjacent interface of a first polypeptide. The cavity may exist in the original interface or may be introduced synthetically (e.g. by altering nucleic acid encoding the interface). Normally, nucleic acid encoding the interface of the second polypeptide is altered to encode the cavity. To achieve this, the nucleic acid encoding at least one "original" amino acid residue in the interface of the second polypeptide is replaced with DNA encoding at least one "import" amino acid residue which has a smaller side chain volume than the original amino acid residue. It will be appreciated that there can be more than one original and corresponding import residue. The upper limit for the number of original residues which are replaced is the total number of residues in the interface of the second polypeptide. The side chain volumes of the various amino residues are shown in Table 2 above. The preferred import residues for the formation of a cavity are usually naturally occurring amino acid residues and are preferably selected from alanine (A), serine (S), threonine (T) and valine (V). Most preferred are serine, alanine or threonine. In one embodiment, the original residue for the formation of the cavity has a large side chain volume, such as tyrosine, arginine, phenylalanine or tryptophan. Exemplary amino acid substitutions in the CH3 domain for generating the cavity include without limitation the T366S, L368A and Y407A substitutions.

An "original" amino acid residue is one which is replaced by an "import" residue which can have a smaller or larger side chain volume than the original residue. The import amino acid residue can be a naturally occurring or non-naturally occurring amino acid residue, but preferably is the former. "Naturally occurring" amino acid residues are those residues encoded by the genetic code and listed in Table 2 above. By "non-naturally occurring" amino acid residue is meant a residue which is not encoded by the genetic code, but which is able to covalently bind adjacent amino acid residue(s) in the polypeptide chain Examples of non-naturally occurring amino acid residues are norleucine, ornithine, norvaline, homoserine and other amino acid residue analogues such as those described in Ellman et al., *Meth. Enzym.* 202:301-336 (1991), for example. To generate such non-naturally occurring amino acid residues, the procedures of Noren et al. *Science* 244: 182 (1989) and Ellman et al., supra can be used. Briefly, this involves chemically activating a suppressor tRNA with a non-naturally occurring amino acid residue followed by in vitro transcription and translation of the RNA. The method of the instant invention involves replacing at least one original amino acid residue, but more than one original residue can be replaced. Normally, no more than the total residues in the interface of the first or second polypeptide will comprise original amino acid residues which are replaced. Typically, original residues for replacement are "buried". By "buried" is meant that the residue is essentially inaccessible to solvent. Generally, the import residue is not cysteine to prevent possible oxidation or mispairing of disulfide bonds.

The protuberance is "positionable" in the cavity which means that the spatial location of the protuberance and cavity on the interface of a first polypeptide and second polypeptide respectively and the sizes of the protuberance and cavity are such that the protuberance can be located in the cavity without significantly perturbing the normal association of the first and second polypeptides at the interface. Since protuberances such as Tyr, Phe and Trp do not typically extend perpendicularly from the axis of the interface and have preferred conformations, the alignment of a protuberance with a corresponding cavity relies on modeling the protuberance/cavity pair based upon a three-dimensional structure such as that obtained by X-ray crystallography or nuclear magnetic resonance (NMR). This can be achieved using widely accepted techniques in the art.

By "original or template nucleic acid" is meant the nucleic acid encoding a polypeptide of interest which can be "altered" (i.e. genetically engineered or mutated) to encode a protuberance or cavity. The original or starting nucleic acid may be a naturally occurring nucleic acid or may comprise a nucleic acid which has been subjected to prior alteration (e.g. a humanized antibody fragment). By "altering" the nucleic acid is meant that the original nucleic acid is mutated by inserting, deleting or replacing at least one codon encoding an amino acid residue of interest. Normally, a codon encoding an original residue is replaced by a codon encoding an import residue. Techniques for genetically modifying a DNA in this manner have been reviewed in Mutagenesis: a Practical Approach, M. J. McPherson, Ed., (IRL Press, Oxford, UK. (1991), and include site-directed mutagenesis, cassette mutagenesis and polymerase chain reaction (PCR) mutagenesis, for example. By mutating an original/template nucleic acid, an original/template polypeptide encoded by the original/template nucleic acid is thus correspondingly altered.

The protuberance or cavity can be "introduced" into the interface of a first or second polypeptide by synthetic means, e.g. by recombinant techniques, in vitro peptide synthesis, those techniques for introducing non-naturally occurring amino acid residues previously described, by enzymatic or chemical coupling of peptides or some combination of these techniques. Accordingly, the protuberance or cavity which is "introduced" is "non-naturally occurring" or "non-native", which means that it does not exist in nature or in the original polypeptide (e.g. a humanized monoclonal antibody).

Generally, the import amino acid residue for forming the protuberance has a relatively small number of "rotamers" (e.g. about 3-6). A "rotamer" is an energetically favorable conformation of an amino acid side chain. The number of rotamers of the various amino acid residues is reviewed in Ponders and Richards, *J. Mol. Biol.* 193: 775-791 (1987).

In one embodiment, a first Fc polypeptide and a second Fc polypeptide meet/interact at an interface. In some embodiments wherein the first and second Fc polypeptides meet at an interface, the interface of the second Fc polypeptide (sequence) comprises a protuberance (also termed a "knob") which is positionable in a cavity (also termed a "hole") in the interface of the first Fc polypeptide (sequence). In one embodiment, the first Fc polypeptide has been altered from a template/original polypeptide to encode the cavity or the second Fc polypeptide has been altered from a template/original polypeptide to encode the protuberance, or both. In one embodiment, the first Fc polypeptide has been altered from a template/original polypeptide to encode the cavity and the second Fc polypeptide has been altered from a template/original polypeptide to encode the protuberance. In one embodiment, the interface of the second Fc polypeptide comprises a protuberance which is positionable in a cavity in the interface of the first Fc polypeptide, wherein the cavity or protuberance, or both, have been introduced into the interface of the first and second Fc polypeptides, respectively. In some embodiments wherein the first and second Fc polypeptides meet at an interface, the interface of the first Fc polypeptide (sequence) comprises a protuberance which is positionable in a cavity in the interface of the second Fc polypeptide (sequence). In one embodiment, the second Fc polypeptide has been altered from a template/original polypeptide to encode the cavity or the first Fc polypeptide has been altered from a template/original polypeptide to encode the protuberance, or both. In one embodiment, the second Fc polypeptide has been altered from a template/original polypeptide to encode the cavity and the first Fc polypeptide has been altered from a template/original polypeptide to encode the protuberance. In one embodiment, the interface of the first Fc polypeptide comprises a protuberance which is positionable in a cavity in the interface of the second Fc polypeptide, wherein the protuberance or cavity, or both, have been introduced into the interface of the first and second Fc polypeptides, respectively.

In one embodiment, the protuberance and cavity each comprise a naturally occurring amino acid residue. In one embodiment, the Fc polypeptide comprising the protuberance is generated by replacing an original residue from the interface of a template/original polypeptide with an import residue having a larger side chain volume than the original residue. In one embodiment, the Fc polypeptide comprising the protuberance is generated by a method comprising a step wherein polynucleotide encoding an original residue from the interface of said polypeptide is replaced with polynucleotide encoding an import residue having a larger side chain volume than the original. In one embodiment, the original residue is threonine. In one embodiment, the original residue is T366. In one embodiment, the import residue is arginine (R). In one embodiment, the import residue is phenylalanine (F). In one embodiment, the import residue is tyrosine (Y). In one embodiment, the import residue is tryptophan (W). In one embodiment, the import residue is R, F, Y or W. In one embodiment, a protuberance is generated by replacing two or more residues in a template/original polypeptide. In one embodiment, the Fc polypeptide comprising a protuberance comprises replacement of threonine at position 366 with tryptophan, amino acid numbering according to the EU numbering scheme of Kabat et al. (pp. 688-696 in Sequences of proteins of immunological interest, 5th ed., Vol. 1 (1991; NIH, Bethesda, Md.)).

In some embodiments, the Fc polypeptide comprising a cavity is generated by replacing an original residue in the interface of a template/original polypeptide with an import residue having a smaller side chain volume than the original residue. For example, the Fc polypeptide comprising the cavity may be generated by a method comprising a step wherein polynucleotide encoding an original residue from the interface of said polypeptide is replaced with polynucleotide encoding an import residue having a smaller side chain volume than the original. In one embodiment, the original residue is threonine. In one embodiment, the original residue is leucine. In one embodiment, the original residue is tyrosine. In one embodiment, the import residue is not cysteine (C). In one embodiment, the import residue is alanine (A). In one embodiment, the import residue is serine (S). In one embodiment, the import residue is threonine (T). In one embodiment, the import residue is valine (V). A cavity can be generated by replacing one or more original residues of a template/original polypeptide. For example, in one embodiment, the Fc polypeptide comprising a cavity comprises replacement of two or more original amino acids selected from the group consisting of threonine, leucine and tyrosine. In one embodiment, the Fc polypeptide comprising a cavity comprises two or more import residues selected from the group consisting of alanine, serine, threonine and valine. In some embodiments, the Fc polypeptide comprising a cavity comprises replacement of two or more original amino acids selected from the group consisting of threonine, leucine and tyrosine, and wherein said original amino acids are replaced with import residues selected from the group consisting of alanine, serine, threonine and valine. In some embodiments, an original amino acid that is replaced is T366, L368 and/or Y407. In one embodiment, the Fc polypeptide comprising a cavity comprises replacement of threonine at position 366 with serine, amino acid numbering according to the EU numbering scheme of Kabat et al. supra. In one embodiment, the Fc polypeptide comprising a cavity comprises replacement of leucine at position 368 with alanine, amino acid numbering according to the EU numbering scheme of Kabat et al. supra. In one embodiment, the Fc polypeptide comprising a cavity comprises replacement of tyrosine at position 407 with valine, amino acid numbering according to the EU numbering scheme of Kabat et al. supra. In one embodiment, the Fc polypeptide comprising a cavity comprises two or more amino acid replacements selected from the group consisting of T366S, L368A and Y407V, amino acid numbering according to the EU numbering scheme of Kabat et al. supra. In some embodiments of these antibody fragments, the Fc polypeptide comprising the protuberance comprises replacement of threonine at position 366 with tryptophan, amino acid numbering according to the EU numbering scheme of Kabat et al. supra.

In one embodiment, the antibody comprises Fc mutations constituting "knobs" and "holes" as described in WO2005/063816. For example, a hole mutation can be one or more of T366A, L368A and/or Y407V in an Fc polypeptide, and a knob mutation can be T366W.

V. Vectors, Host Cells, and Recombinant Methods

For recombinant production of a heterologous polypeptide (e.g., an antibody) using DsbA and DsbC, the nucleic acid encoding it is isolated and inserted into a replicable vector for further cloning (amplification of the DNA) or for expression. DNA encoding the polypeptide (e.g., antibody) is readily isolated and sequenced using conventional procedures (e.g., by using oligonucleotide probes that are capable of binding specifically to genes encoding the heavy and light chains of the antibody). Many vectors are available. The choice of vector depends in part on the host cell to be used. Generally, preferred host cells are of either prokaryotic origin. It will be appreciated that constant regions of any isotype can be used for this purpose, including IgG, IgM, IgA, IgD, and IgE constant regions, and that such constant regions can be obtained from any human or animal species.

A. Generating Antibodies Using Prokaryotic Host Cells:
i. Vector Construction

Polynucleotide sequences encoding polypeptide components of the polypeptide (e.g., antibody) of the invention can be obtained using standard recombinant techniques. Desired polynucleotide sequences may be isolated and sequenced from antibody producing cells such as hybridoma cells. Alternatively, polynucleotides can be synthesized using nucleotide synthesizer or PCR techniques. Once obtained, sequences encoding the polypeptides are inserted into a recombinant vector capable of replicating and expressing heterologous polynucleotides in prokaryotic hosts. Many vectors that are available and known in the art can be used for the purpose of the present invention. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to: an origin of replication, a selection marker gene, a promoter, a ribosome binding site (RBS), a signal sequence, the heterologous nucleic acid insert and a transcription termination sequence.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is typically transformed using pBR322, a plasmid derived from an *E. coli* species. pBR322 contains genes encoding ampicillin (Amp) and tetracycline (Tet) resistance and thus provides easy means for identifying transformed cells. pBR322, its derivatives, or other microbial plasmids or bacteriophage may also contain, or be modified to contain, promoters which can be used by the microbial organism for expression of endogenous proteins. Examples of pBR322 derivatives used for expression of particular antibodies are described in detail in Carter et al., U.S. Pat. No. 5,648,237.

In addition, phage vectors containing replicon and control sequences that are compatible with the host microorganism can be used as transforming vectors in connection with these hosts. For example, bacteriophage such as GEM™-11 may be utilized in making a recombinant vector which can be used to transform susceptible host cells such as *E. coli* LE392.

The expression vector of the invention may comprise two or more promoter-cistron pairs, encoding each of the polypeptide components. A promoter is an untranslated regulatory sequence located upstream (5') to a cistron that modulates its expression. Prokaryotic promoters typically fall into two classes, inducible and constitutive. Inducible promoter is a promoter that initiates increased levels of transcription of the cistron under its control in response to changes in the culture condition, e.g., the presence or absence of a nutrient or a change in temperature.

A large number of promoters recognized by a variety of potential host cells are well known. The selected promoter can be operably linked to cistron DNA encoding the light or heavy chain by removing the promoter from the source DNA via restriction enzyme digestion and inserting the isolated promoter sequence into the vector of the invention. Both the native promoter sequence and many heterologous promoters may be used to direct amplification and/or expression of the target genes. In some embodiments, heterologous promoters are utilized, as they generally permit greater transcription and higher yields of expressed target gene as compared to the native target polypeptide promoter.

Promoters suitable for use with prokaryotic hosts include the PhoA promoter, the -lactamase and lactose promoter systems, a tryptophan (trp) promoter system and hybrid promoters such as the tac or the trc promoter. However, other promoters that are functional in bacteria (such as other known bacterial or phage promoters) are suitable as well. Their nucleotide sequences have been published, thereby enabling a skilled worker operably to ligate them to cistrons encoding the target light and heavy chains (Siebenlist et al., (1980) *Cell* 20: 269) using linkers or adaptors to supply any required restriction sites.

The translational initiation region (TIR) is a major determinant of the overall translation level of a protein. The TIR includes the polynucleotide that encodes the signal sequence, and extends from immediately upstream of the Shine-Delgarno sequence to approximately twenty nucleotides downstream of the initiation codon. Generally, the vector will comprise a TIR, TIRs and variant TIRs are known in the art and methods for generating TIRs are known in in the art A series of nucleic acid sequence variants can be created with a range of translational strengths, thereby providing a convenient means by which to adjust this factor for the optimal secretion of many different polypeptides. The use of a reporter gene fused to these variants, such as PhoA, provides a method to quantitate the relative translational strengths of different translation initiation regions. The variant or mutant TIRs can be provided in the background of a plasmid vector thereby providing a set of plasmids into which a gene of interest may be inserted and its expression measured, so as to establish an optimum range of translational strengths for maximal expression of mature polypeptide. Variant TIRs are disclosed in U.S. Pat. No. 8,241,901.

In one aspect of the invention, each cistron within the recombinant vector comprises a secretion signal sequence component that directs translocation of the expressed polypeptides across a membrane. In general, the signal sequence may be a component of the vector, or it may be a part of the target polypeptide DNA that is inserted into the vector. The signal sequence selected for the purpose of this invention should be one that is recognized and processed (i.e., cleaved by a signal peptidase) by the host cell. For prokaryotic host cells that do not recognize and process the signal sequences native to the heterologous polypeptides, the signal sequence is substituted by a prokaryotic signal sequence selected, for example, from the signal polypeptides of the present invention. In addition, the vector may comprise a signal sequence selected from the group consisting of alkaline phosphatase, penicillinase, Lpp, or heat-stable enterotoxin II (STII) leaders, LamB, PhoE, PelB, OmpA, and MBP.

In one aspect, one or more polynucleotides (e.g., expression vectors) collectively encode an antibody. In one embodiment, a single polynucleotide encodes the light chain of the antibody and a separate polynucleotide encodes the heavy chain of the antibody. In one embodiment, a single polynucleotide encodes the light chain and heavy chain of the antibody. In some embodiments, one or more polynucleotides (e.g., expression vectors) collectively encode a one-armed antibody. In one embodiment, a single polynucleotide encodes (a) the light and heavy chain of the one armed antibody, and (b) the Fc polypeptide. In one embodiment, a single polynucleotide encodes the light and heavy chain of the one armed antibody, and a separate polynucleotide encodes the Fc polypeptide. In one embodiment, separate polynucleotides encode the light chain component of the one-armed antibody, the heavy chain component of the one-armed antibody and the Fc polypeptide, respectively. Production of a one-armed antibody is described in, for example, in WO2005063816.

Prokaryotic host cells suitable for expressing antibodies of the invention include Archaebacteria and Eubacteria, such as Gram-negative or Gram-positive organisms. Examples of useful bacteria include *Escherichia* (e.g., *E. coli*), Bacilli (e.g., *B. subtilis*), Enterobacteria, *Pseudomonas* species (e.g., *P. aeruginosa*), *Salmonella typhimurium*, *Serratia marcescans*, *Klebsiella*, *Proteus*, *Shigella*, *Rhizobia*, *Vitreoscilla*, or *Paracoccus*. In one embodiment, gram-negative cells are used. In one embodiment, *E. coli* cells are used as hosts for the invention. Examples of *E. coli* strains include strain W3110 (Bachmann, *Cellular and Molecular Biology*, vol. 2 (Washington, D.C.: American Society for Microbiology, 1987), pp. 1190-1219; ATCC Deposit No. 27,325) and derivatives thereof, including strain 33D3 having genotype W3110 ΔfhuA (ΔtonA) ptr3 lac Iq lacL8 ΔompTΔ (nmpc-fepE) degP41 kanR (U.S. Pat. No. 5,639,635) and strains 63C1 and 64B4. In some embodiment, the *E. coli* strain is a W3110 derivative named 62A7 (AfhuA (AtonA) ptr3, lacIq, lacL8, ompTΔ(nmpc-fepE) ΔdegP ilvG repaired). Other strains and derivatives thereof, such as *E. coli* 294 (ATCC 31,446), *E. coli* B, *E. coli* 1776 (ATCC 31,537) and *E. coli* RV308(ATCC 31,608) are also suitable. These examples are illustrative rather than limiting. Methods for constructing derivatives of any of the above-mentioned bacteria having defined genotypes are known in the art and described in, for example, Bass et al., *Proteins*, 8:309-314 (1990). It is generally necessary to select the appropriate bacteria taking into consideration replicability of the replicon in the cells of a bacterium. For example, *E. coli*, *Serratia*, or *Salmonella* species can be suitably used as the host when well known plasmids such as pBR322, pBR325, pACYC177, or pKN410 are used to supply the replicon. Typically the host cell should secrete minimal amounts of proteolytic enzymes, and additional protease inhibitors may desirably be incorporated in the cell culture.

To improve the production yield and quality of the polypeptides in bacterial cultures, the bacterial cells can be modified. For example, to improve the proper assembly and folding of the secreted antibody polypeptides, the bacteria host cell may comprise additional vectors overexpressing chaperone proteins, such as Dsb proteins (DsbA, DsbB, DsbC, DsbD, and/or DsbG) can be used to co-transform the host prokaryotic cells. The chaperone proteins have been demonstrated to facilitate the proper folding and solubility of heterologous proteins produced in bacterial host cells.

ii. Antibody Production

Host cells are transformed with the above-described expression vectors and cultured in conventional nutrient media modified as appropriate for inducing promoters, selecting transformants, or amplifying the genes encoding the desired sequences.

Transformation means introducing DNA into the prokaryotic host so that the DNA is replicable, either as an extrachromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol/DMSO. Yet another technique used is electroporation.

Prokaryotic cells used to produce the polypeptides of the invention are grown in media known in the art and suitable for culture of the selected host cells. Examples of suitable media include Luria broth (LB) plus necessary nutrient supplements. In some embodiments, the media also contains a selection agent, chosen based on the construction of the expression vector, to selectively permit growth of prokaryotic cells containing the expression vector. For example, ampicillin is added to media for growth of cells expressing ampicillin resistant gene.

Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol.

The prokaryotic host cells are cultured at suitable temperatures. For *E. coli* growth, for example, the preferred temperature ranges from about 20° C. to about 39° C., more preferably from about 25° C. to about 37° C., even more preferably at about 30° C. The pH of the medium may be any pH ranging from about 5 to about 9, depending mainly on the host organism. For *E. coli*, the pH is preferably from about 6.8 to about 7.4, and more preferably about 7.0.

If an inducible promoter is used in the expression vector of the invention, protein expression is induced under conditions suitable for the activation of the promoter. In one aspect of the invention, PhoA promoters are used for controlling transcription of the polypeptides. Accordingly, the transformed host cells are cultured in a phosphate-limiting medium for induction. Preferably, the phosphate-limiting medium is the C.R.A.P medium (see, e.g., Simmons et al., *J. Immunol. Methods* (2002), 263:133-147) or media described in WO2002/061090. A variety of other inducers may be used, according to the vector construct employed, as is known in the art.

In one embodiment, the expressed polypeptides of the present invention are secreted into and recovered from the periplasm of the host cells. Protein recovery typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported into the culture media and isolated therein. Cells may be removed from the culture and the culture supernatant being filtered and concentrated for further purification of the proteins produced. The expressed polypeptides can be further isolated and identified using commonly known methods such as polyacrylamide gel electrophoresis (PAGE) and Western blot assay.

In one aspect of the invention, antibody production is conducted in large quantity by a fermentation process. Various large-scale fed-batch fermentation procedures are available for production of recombinant polypeptides. Large-scale fermentations have at least 1000 liters of capacity, preferably about 1,000 to 100,000 liters of capacity. These fermentors use agitator impellers to distribute oxygen and nutrients, especially glucose (the preferred carbon/energy source) Small scale fermentation refers generally to fermentation in a fermenter that is no more than approximately 100 liters in volumetric capacity, and can range from about 1 liter to about 100 liters.

In a fermentation process, induction of protein expression is typically initiated after the cells have been grown under suitable conditions to a desired density, e.g., an OD550 of about 180-220, at which stage the cells are in the early stationary phase. A variety of inducers may be used, according to the vector construct employed, as is known in the art and described above. Cells may be grown for shorter periods prior to induction. Cells are usually induced for about 12-50 hours, although longer or shorter induction time may be used.

To improve the production yield and quality of the polypeptides of the invention, various fermentation conditions can be modified. For example, to improve the proper assembly and folding of the secreted antibody polypeptides, additional vectors overexpressing chaperone proteins, such as Dsb proteins (DsbA, DsbB, DsbC, DsbD, and/or DsbG) can be used to co-transform the host prokaryotic cells. The chaperone proteins have been demonstrated to facilitate the proper folding and solubility of heterologous proteins produced in bacterial host cells. Chen et al., (1999) *J. Biol. Chem.* 274:19601-19605; Georgiou et al., U.S. Pat. No. 6,083,715; Georgiou et al., U.S. Pat. No. 6,027,888; Bothmann and Pluckthun (2000) *J. Biol. Chem.* 275:17100-17105; Ramm and Pluckthun, (2000) *J. Biol. Chem.* 275: 17106-17113; Arie et al., (2001) *Mol. Microbiol.* 39:199-210. In some embodiments, DsbA and C are expressed in the bacterial host cell.

To minimize proteolysis of expressed heterologous proteins (especially those that are proteolytically sensitive), certain host strains deficient for proteolytic enzymes can be used for the present invention. For example, host cell strains may be modified to effect genetic mutation(s) in the genes encoding known bacterial proteases such as Protease III, OmpT, DegP, Tsp, Protease I, Protease Mi, Protease V, Protease VI, and combinations thereof. Some *E. coli* protease-deficient strains are available and described in, for example, Joly et al., (1998), supra; Georgiou et al., U.S. Pat. No. 5,264,365; Georgiou et al., U.S. Pat. No. 5,508,192; Hara et al., *Microbial Drug Resistance*, 2:63-72 (1996).

In one embodiment, *E. coli* strains deficient for proteolytic enzymes and transformed with plasmids overexpressing one or more chaperone proteins are used as host cells in the expression system of the invention.

iii. Antibody Purification

Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration using, for example, Sephadex G-75.

In one aspect, Protein A immobilized on a solid phase is used for immunoaffinity purification of the antibody products of the invention. Protein A is a 41 kD cell wall protein from *Staphylococcus aureas* which binds with a high affinity to the Fc region of antibodies. Lindmark et al., (1983) *J. Immunol. Meth.* 62:1-13. The solid phase to which Protein A is immobilized is preferably a column comprising a glass or silica surface, more preferably a controlled pore glass column or a silicic acid column. In some applications, the column has been coated with a reagent, such as glycerol, in an attempt to prevent nonspecific adherence of impurities.

As the first step of purification, the preparation derived from the cell culture as described above is applied onto the Protein A immobilized solid phase to allow specific binding of the antibody of interest to Protein A. The solid phase is then washed to remove impurities non-specifically bound to the solid phase. Finally the antibody of interest is recovered from the solid phase by elution.

In some embodiments of the invention, fractions derived from one or more of the purification steps are analyzed for the removal of DsbA and/or DsbC. In some embodiments, the removal of DsbA and/or DsbC is determined by immunoassay; for example, by the immunoassays described herein.

The invention also provides immunoconjugates (interchangeably termed "antibody-drug conjugates" or "ADC"), comprising any of the antibodies described herein conjugated to, e.g., a cytotoxic agent such as a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate).

VI. Compositions of DsbA and DsbC

In some aspects, the invention provides compositions comprising ultrapure DsbA and/or DsbC. In some embodiments, the composition comprises DsbA wherein the DsbA is more than about any of 95.0%, 96.0%, 97.0%, 98.0%, 99.0%, or 99.5% monomericDsbA. In some embodiments, a composition comprising 95% monomeric DsbA is a composition where less than 5% of the material in the preparation are other substances that were present in the cells or cell lysates (e.g., protein, nucleic acids, lipids, etc.) present during the production of the DsbA. In some embodiments, the percentage of monomeric DsbA polypeptide is measured by size exclusion chromatography (e.g., SEC-HPLC). In some embodiments, the composition comprising ultrapure DsbA comprises less than about any of 5%, 4%, 3%, 2%, 1%, 0.5% or 0.1% low molecular weight species (e.g., species with a molecular weight less than monomeric DsbA as measured by SEC or SDS-PAGE). In some embodiments, the composition comprising ultrapure DsbA comprises less than about 2% low molecular weight species. In some embodiments, the composition comprising ultrapure DsbA comprises less than about any of 5%, 4%, 3%, 2%, 1%, 0.5% or 0.1% high molecular weight species (e.g., species with a molecular weight greater than monomeric DsbA as measured by SEC or SDS-PAGE). In some embodiments, the composition comprising ultrapure DsbA comprises less than about 1% high molecular weight species.

In some embodiments, the composition comprises DsbC wherein the DsbC is more than about any of 95.0%, 96.0%, 97.0%, 98.0%, 99.0%, or 99.5% monomeric DsbC. In some embodiments, a composition comprising 95% monomeric DsbC is a composition where less than 5% of the material in the preparation are other substances that were present in the cells or cell lysates (e.g., protein, nucleic acids, lipids, etc.) present during the production of the DsbC. In some embodiments, the percentage of monomeric DsbC polypeptide is measured by size exclusion chromatography (e.g., SEC-HPLC). In some embodiments, the composition comprising ultrapure DsbC comprises less than about any of 5%, 4%, 3%, 2%, 1%, 0.5% or 0.1% low molecular weight species (e.g., species with a molecular weight less than monomeric DsbC as measured by SEC or SDS-PAGE). In some embodiments, the composition comprising ultrapure DsbC comprises less than about 2% low molecular weight species. In some embodiments, the composition comprising ultrapure DsbC comprises less than about any of 5%, 4%, 3%, 2%, 1%, 0.5% or 0.1% high molecular weight species (e.g., species with a molecular weight greater than monomeric DsbC as measured by SEC or SDS-PAGE). In some embodiments, the composition comprising ultrapure DsbC comprises less than about 1% high molecular weight species.

In some embodiments, the composition comprising highly purified DsbA or DsbC is formulated for use. In some embodiments, the composition comprising ultrapure DsbA or DsbC is formulated for immunizing animals to generate antibodies to DsbA or DsbC; for example, by adding adjuvants to facilitate the generation of an immune response. In other embodiments, the composition comprising ultrapure DsbA or DsbC is formulated for use in immunoassays; for example, as a positive control or as a standard curve.

VII. Generation of Antibodies to DsbA and DsbC

In certain aspects, the invention provides ultrapure DsbA and ultrapure DsbC to use as an immunogen to generate antibodies (e.g., polyclonal antibodies and/or monoclonal antibodies) for use in immunoassays for analyzing recombinant polypeptide samples for the presence of DsbA and/or DsbC. For example, the antibodies may be used in immunoassays to detect and/or quantitate DsbA and or DsbC in recombinant polypeptide samples where the recombinant polypeptide was produced in bacterial cells that overexpress DsbA and/or DsbC. In some embodiments, the invention provides polyclonal antibodies that specifically bind ultrapure DsbA and/or polyclonal antibodies that specifically bind ultrapure DsbC. In some aspects, polyclonal antibodies specifically bind different epitopes of DsbA or DsbC and therefore provide utility to detect DsbA or DsbC fragments, variant, misfolded protein, etc. In order to minimize the generation of rabbit antibodies against host cell protein impurities, which might result in an over-quantitation of the level of DsbA or DsbC in samples being measured in the immunoassay, animals (e.g., rabbits) are immunized with ultrapure DsbA or DsbC.

The invention provides antibodies that specifically bind DsbA and antibodies that specifically bind DsbC. In some embodiments, antibodies are polyclonal antibodies. Polyclonal antibodies are preferably raised in animals by multiple subcutaneous (sc) or intraperitoneal (ip) injections of the relevant antigen and an adjuvant. It may be useful to conjugate the relevant antigen to a polypeptide that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R1N=C=NR$, where R and R1 are different alkyl groups.

Animals are immunized against the antigen, immunogenic conjugates, or derivatives by combining, e.g., 100 µg or 5 µg of the polypeptide or conjugate (for rabbits or mice, respectively) with 3 volumes of Freund's complete adjuvant and injecting the solution intradermally at multiple sites. One month later the animals are boosted with ⅕ to ¹⁄₁₀ the original amount of peptide or conjugate in Freund's complete adjuvant by subcutaneous injection at multiple sites. Seven to 14 days later the animals are bled and the serum is assayed for antibody titer. Animals are boosted until the titer plateaus. In some embodiments, the animal is boosted with the conjugate of the same antigen, but conjugated to a different polypeptide and/or through a different cross-linking reagent. Conjugates also can be made in recombinant cell culture as polypeptide fusions. Also, aggregating agents such as alum are suitably used to enhance the immune response.

In some embodiments, the animal immunized with DsbA or DsbC is a goat, a sheep, a rabbit, a mouse, a guinea pig, a hamster, a rat, a donkey or a chicken.

In some embodiments, the antibodies that specifically bind DsbA or DsbC are monoclonal antibodies. Monoclonal antibodies are obtained from a population of substantially homogeneous antibodies, i.e., the individual antibodies comprising the population are identical and/or bind the same epitope except for possible variants that arise during production of the monoclonal antibody, such variants generally being present in minor amounts. Thus, the modifier "monoclonal" indicates the character of the antibody as not being a mixture of discrete or polyclonal antibodies. As described above, the monoclonal antibodies may be made using the hybridoma method first described by Kohler et al., *Nature* 256:495 (1975), or may be made by recombinant DNA methods (U.S. Pat. No. 4,816,567).

In some aspects, the invention provides methods for purifying antibodies that specifically bind DsbA, comprising contacting a composition comprising anti-DsbA antibodies to chromatography material comprising ultrapure DsbA attached to a support material, washing the chromatography material to remove unbound compounds, and eluting the anti-DsbA antibodies. In some embodiments, the ultrapure DsbA that is attached to the support material comprises less than about any of 1%, 0.9%, 0.8%, 0.7%, 0.6%, 0.5%, 0.4%, 0.3%, 0.2%, 0.1%, 0.05%, 0.01% impurities. In some embodiments, the ultrapure DsbA is prepared by the methods described herein. In some embodiments, the invention provides methods to purify polyclonal antibodies that specifically bind DsbA. In some embodiments, less than about any of 1%, 0.9%, 0.8%, 0.7%, 0.6%, 0.5%, 0.4%, 0.3%, 0.2%, 0.1%, 0.05%, 0.01% of the polyclonal antibodies specifically bind non-DsbA compounds.

In some aspects, the invention provides methods for purifying antibodies that specifically bind DsbC, comprising contacting a composition comprising anti-DsbC antibodies to chromatography material comprising ultrapure DsbC attached to a support material, washing the chromatography material to remove unbound compounds, and eluting the anti-DsbC antibodies. In some embodiments, the ultrapure DsbA that is attached to the support material comprises less than about any of 1%, 0.9%, 0.8%, 0.7%, 0.6%, 0.5%, 0.4%, 0.3%, 0.2%, 0.1%, 0.05%, 0.01% impurities. In some embodiments, the ultrapure DsbC is prepared by the methods described herein. In some embodiments, the invention provides methods to purify polyclonal antibodies that specifically bind DsbC. In some embodiments, less than about any of 1%, 0.9%, 0.8%, 0.7%, 0.6%, 0.5%, 0.4%, 0.3%, 0.2%, 0.1%, 0.05%, 0.01% of the polyclonal antibodies specifically bind non-DsbC compounds.

In some embodiments, anti-DsbA and/or anti-DsbC antibodies are purified by contacting the antibodies to ultrapure DsbA or DsbC immobilized on a chromatography material (e.g., ultrapure DsbA and or DsbC immobilized to activated glyceryl-controlled pore glass). In some embodiments, the antibodies are concentrated, for example, by ammonium sulfate precipitation prior to contact with the immobilized DsbA or DsbC. In some embodiments, the antibodies are bound to the immobilized DsbA or DsbC and then the immobilized DsbA or DsbC-antibody complexes are washed to remove non-bound impurities. In further embodiments, the antibodies are eluted from the immobilized DsbA or DsbC by eluting with a buffer at a different pH as the load buffer; for example, the antibodies are bound to the immobilized DsbA or DsbC ate neutral pH (e.g., pH 7.2) and eluted at acidic pH (e.g., pH 2.0). In some further embodiments, the anti-DsbA or anti-DsbC antibodies are subject to further chromatography; for example size exclusion chromatography. In some embodiments, the purified anti-DsbA or anti-DsbC antibodies (e.g., polyclonal antibodies) are assayed for their binding to ultrapure DsbA or DsbC, respectively.

VIII. Immunoassays Using Antibodies to DsbA and DsbC

In some embodiments, the invention provides a method for analyzing a recombinant polypeptide sample for the presence of and/or quantity of DsbA, comprising detecting DsbA in the sample using an immunoassay and comparing the amount of DsbA detected in the sample with the detection of one or more concentrations of an ultrapure DsbA reference standard. In some embodiments, the preparation comprises less than about any of 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, or 0.01% of impurities. In some embodiments, the ultrapure DsbA reference standard is prepared by the methods described herein. In some embodiments, the immunoassay comprises antibodies that specifically bind ultrapure DsbA. In some embodiments, the antibodies that specifically bind ultrapure DsbA bind less than about any of 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, or 0.01% of non-DsbA compounds. In some embodiments, the antibodies that specifically bind ultrapure DsbA are polyclonal antibodies. In other embodiments, the antibodies that specifically bind ultrapure DsbA are monoclonal antibodies. In some embodiments, the antibodies that specifically bind ultrapure DsbA are used as capture antibodies in the immunoassay. In some embodiments, the antibodies that specifically bind ultrapure DsbA are used as detection antibodies. In some embodiments, the detection antibodies are conjugated to a detection agent (e.g., a horseradish peroxidase). In some embodiments, the DsbA is an E. coli DsbA. In some embodiments, the recombinant polypeptide is prepared in a host cell (e.g., an E. coli host cell). In some embodiments, the host cell overexpresses DsbA (e.g., an E. coli host cell that overexpressed DsbA). In some embodiments, the sample is cell lysate or is obtained from a recombinant polypeptide preparation and wherein the recombinant polypeptide preparation has been subjected to one or more chromatographic purification steps. In some embodiment, the recombinant polypeptide preparation is a final purified product. In some embodiments, the antibodies that specifically bind ultrapure DsbA are capable of detecting less than about and/or about any of 50 ng/mL, 25 ng/mL, 15 ng/mL, 10 ng/mL, 5 ng/mL, 2.5 ng/mL, and/or 1.5 ng/mL of DsbA in an immunoassay.

In some embodiments, the invention provides a method for analyzing a recombinant polypeptide sample for the presence of and/or quantity of DsbC, comprising detecting DsbC in the sample using an immunoassay and comparing the amount of DsbC detected in the sample with the detection of one or more concentrations of an ultrapure DsbC reference standard. In some embodiments, the preparation comprises less than about any of 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, or 0.01% of impurities. In some embodiments, the ultrapure DsbC reference standard is prepared by the methods described herein. In some embodiments, the immunoassay comprises antibodies that specifically bind ultrapure DsbC. In some embodiments, the antibodies that specifically bind ultrapure DsbC bind less than about any of 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, or 0.01% of non-DsbC compounds. In some embodiments, the antibodies that specifically bind ultrapure DsbC are polyclonal antibodies. In other embodiments, the antibodies that specifically bind ultrapure DsbC are monoclonal antibodies. In some embodiments, the antibodies that specifically bind ultrapure DsbC are used as capture antibodies in the immunoassay. In some embodiments, the antibodies that specifically bind ultrapure DsbC are capable of detecting less than about and/or about any of 50 ng/mL, 35 ng/mL, 25 ng/mL, 15 ng/mL, 10 ng/mL, 5 ng/mL, 2.5 ng/mL, 1.5 ng/mL, and/or 1 ng/mL of DsbC in an immunoassay. In some embodiments, the antibodies that specifically bind ultrapure DsbC are used as detection antibodies. In some embodiments, the detection antibodies are conjugated to a detection agent (e.g., a horseradish peroxidase). In some embodiments, the DsbC is an E. coli DsbC. In some embodiments, the recombinant polypeptide is prepared in a host cell (e.g., an E. coli host cell). In some embodiments, the host cell overexpresses DsbC (e.g., an E. coli host cell that overexpressed DsbC). In some embodiments, the sample is cell lysate or is obtained from a recombinant polypeptide preparation and wherein the recombinant polypeptide preparation has been subjected to one or more chromatographic purification steps. In some embodiment, the recombinant polypeptide preparation is a final purified product.

In some aspects, the invention provides immunoassay methods for detection and quantification of DsbA and DsbC. Such methods may be used for the detection and quantification of DsbA and DsbC in recombinant polypeptide preparations produced in host cells, for example E. coli where DsbA and/or DsbC are overexpressed to facilitate polypeptide folding and assembly. In some embodiments, the immunoassay methods use capture and detection anti-DsbA or DsbC antibodies described herein. In some embodiments, the antibodies are used in any immunoassay method known in the art, including but not limited to, sandwich assay, enzyme-linked immunosorbent assay (ELISA) assay, electrochemical assay (ECL) assay, magnetic immunoassay. In certain embodiments, the method comprises contacting a sample of the recombinant polypeptide preparation with an anti-DsbA or anti-DsbC antibody as described herein under conditions permissive for binding of the anti-DsbA or anti-DsbC antibody to DsbA or DsbC, and detecting whether a complex is formed between the anti-DsbA or anti-DsbC antibody and DsbA or DsbC, respectively.

In certain embodiments, labeled anti-DsbA and/or anti-DsbC antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

In certain embodiments, a capture anti-DsbA or anti-DsbC antibody is immobilized on a solid phase. In some embodiments, the solid phase used for immobilization is any inert support or carrier that is essentially water insoluble and useful in immunometric assays, including supports in the form of, e.g., surfaces, particles, porous matrices, beads and the like. Examples of commonly used supports include small sheets, SEPHADEX®, gels, polyvinyl chloride, plastic beads, and assay plates or test tubes manufactured from polyethylene, polypropylene, polystyrene, and the like, including 96-well microtiter plates, as well as particulate materials such as filter paper, agarose, cross-linked dextran, and other polysaccharides. Alternatively, reactive water-insoluble matrices such as cyanogen-bromide-activated carbohydrates and the reactive substrates described in U.S. Pat. Nos. 3,969,287; 3,691,016; 4,195,128; 4,247,642; 4,229,537; and 4,330,440 are suitably employed for capture-reagent immobilization. In some embodiments, the immobilized capture reagents are coated on a microtiter plate that can be used to analyze several samples at one time. Exemplary microtiter plates include, but are not limited to, MICROTEST®, MAXISORP®, NUNC MAXISORB®, and IMMULON®. The solid phase is coated with the capture reagents as defined above, which may be linked by a non-covalent or covalent interaction or physical linkage as desired. Techniques for attachment include those described in U.S. Pat. No. 4,376,110 and the references cited therein. If covalent, the plate or other solid phase is incubated with a cross-linking agent together with the capture reagent under conditions well known in the art such as for one hour at room temperature. In some embodiments, the plates are stacked and coated long in advance of the assay itself, and then the assay is carried out simultaneously on several samples in a manual, semi-automatic, or automatic fashion, such as by using robotics.

In some embodiments, the coated plates are treated with a blocking agent that binds non-specifically to and saturates the binding sites to prevent unwanted binding of the free ligand to the excess sites on the wells of the plate. Examples of appropriate blocking agents for this purpose include but are not limited to, e.g., gelatin, bovine serum albumin, egg albumin, casein, and non-fat milk. The blocking treatment typically takes place under conditions of ambient temperatures for a period of time, typically about 1-4 hours.

In some embodiments, after coating and blocking, the sample to be analyzed, appropriately diluted, is added to the immobilized phase. Exemplary buffers that may be used for dilution for this purpose include, but are not limited to, (a) phosphate-buffered saline (PBS) containing 0.5% BSA, 0.05% TWEEN 20® detergent (P20), 0.05% PROCLIN® 300 antibiotic, 5 mM EDTA, 0.25% 3-((3-cholamidopropyl) dimethylammonio)-1-propanesulphonate (CHAPS) surfactant, 0.2% beta-gamma globulin, and 0.35M NaCl; (b) PBS containing 0.5% bovine serum albumin (BSA), 0.05% P20, and 0.05% PROCLIN® 300, pH 7; (c) PBS containing 0.5% BSA, 0.05% P20, 0.05% PROCLIN® 300, 5 mM EDTA, and 0.35 M NaCl, pH 6.35; (d) PBS containing 0.5% BSA, 0.05% P20, 0.05% PROCLIN® 300, 5 mM EDTA, 0.2% beta-gamma globulin, and 0.35 M NaCl; and (e) PBS containing 0.5% BSA, 0.05% P20, 0.05% PROCLIN® 300, 5 mM EDTA, 0.25% CHAPS, and 0.35 M NaCl.

The conditions for incubation of sample and immobilized capture reagent are selected to maximize sensitivity of the assay and to minimize dissociation, and to ensure that any analyte of interest present in the sample (such as DsbA or DsbC) binds to the immobilized capture reagent. Optionally, the sample is separated (for example, by washing) from the immobilized capture reagents to remove uncaptured material. The solution used for washing is generally a buffer (e.g., "washing buffer"). A cross-linking agent or other suitable agent may also be added at this stage to allow the now-bound material of interest (e.g., DsbA or DsbC) to be covalently attached to the capture reagents if there is any concern that the captured material of interest may dissociate to some extent in the subsequent steps.

The immobilized capture reagents with any bound material of interest present are contacted with a detection anti-DsbA or anti-DsbC antibody. In some embodiments, the detection antibody is biotinylated. In some embodiments, the detection means for the biotinylated label is avidin or streptavidin-HRP. In some embodiments, the readout of the detection means is fluorimetric or colorimetric.

The level of any free material of interest from the sample (e.g., DsbA or DsbC) that is now bound to the capture reagents is measured or quantified using a detection means for the detection antibody. In some embodiments, the measuring or quantifying comprises comparing the reaction that occurs as a result of the above steps with a standard curve to determine the level of material of interest (e.g., DsbA or DsbC) compared to a known amount.

The antibody added to the immobilized capture reagents will be either directly labeled, or detected indirectly by addition, after washing off of excess first antibody, of a molar excess of a second, labeled antibody directed against IgG of the animal species of the first antibody. In the latter, indirect assay, labeled antisera against the first antibody are added to the sample so as to produce the labeled antibody in situ.

The label used for either the first or second antibody is any detectable functionality that does not interfere with the binding of free material of interest (e.g., DsbA or DsbC) to the first or second antibodies. Examples of suitable labels include those known for use in immunoassay, such as those enumerated above.

Conventional methods are available to bind these labels covalently to proteins or polypeptides. For instance, coupling agents such as dialdehydes, carbodiimides, dimaleimides, bis-imidates, bis-diazotized benzidine, and the like may be used to tag the antibodies with the above-described fluorescent, chemiluminescent, and enzyme labels. See, for example, U.S. Pat. No. 3,940,475 (fluorimetry) and U.S. Pat. No. 3,645,090 (enzymes); Hunter et al., *Nature* 144:945 (1962); David et al., *Biochemistry*, 13:1014-1021 (1974); Pain et al., *J. Immunol. Methods* 40:219-230 (1981); and Nygren, *J. Histochem. and Cytochem.*, 30:407-412 (1982). In some embodiments, the label is biotin using streptavidin-HRP for detection means.

The conjugation of such label, including the enzymes, to the antibody is a standard manipulative procedure for one of ordinary skill in immunoassay techniques. See, for example, O'Sullivan et al. "Methods for the Preparation of Enzyme-antibody Conjugates for Use in Enzyme Immunoassay," in Methods in Enzymology, ed. J. J. Langone and H. Van Vunakis, Vol. 73 (Academic Press, New York, N.Y., 1981), pp. 147-166.

Following the addition of last labeled antibody, the amount of bound antibody is determined by removing excess unbound labeled antibody through washing and then measuring or quantifying the amount of the attached label using a detection method appropriate to the label, and correlating the measured amount with the amount of the antibody of interest in the biological sample. For example, in the case of enzymes, the amount of color developed and measured will be a direct measurement allowing quantification of the amount of the antibody of interest present. In one embodiment, HRP is the label and the color is detected using the substrate OPD at 490-nm absorbance.

In one example, after an enzyme-labeled second antibody directed against the first unlabeled antibody is washed from the immobilized phase, color or chemiluminiscence is developed and measured by incubating the immobilized capture reagent with a substrate of the enzyme. Then the concentration of the material of interest (e.g., DsbA or DsbC) is calculated by comparing with the color or chemiluminescence generated by the standard run in parallel.

In some embodiments, the invention provides quality assays for pharmaceutical compositions comprising a recombinant polypeptide prepared in bacteria comprising DsbA and/or DsbC to facilitate protein folding and assembly. In some embodiments, the bacterial cell overexpresses DsbA and/or DsbC. In some embodiments, the bacterial cell is an *E. coli* cell. In some embodiments, the bacterial cell is an *E. coli* cell that overexpressed DsbA and/or DsbC. In some embodiments, the quality assay comprises subjecting a sample of the composition comprising the recombinant polypeptide to immunoassays to detect DsbA or DsbC wherein the detection of DsbA or DsbC above certain amounts indicates that the pharmaceutical composition of the therapeutic polypeptide is not suitable for administration to an animal. In some embodiments, the sample of the composition comprising the recombinant polypeptide is a cell lysate. In some embodiments, the sample is obtained from the composition comprising the recombinant polypeptide wherein the recombinant polypeptide has been subjected to one or more chromatographic purification steps. In some embodiments, the composition comprising the recombinant polypeptide is the final purified product. In some embodiments, a concentration of DsbA and/or DsbC of less than about any of 50 ppm, 40 ppm, 30 ppm, 20 ppm, 10 ppm, 9 ppm, 8 ppm, 7 ppm, 6 ppm, 5 ppm, 4 ppm, 3 ppm, 2 ppm, 1 ppm, 0.9 ppm, 0.8 ppm, 0.7 ppm, 0.6 ppm, 0.5 ppm, 0.4 ppm, 0.3 ppm, 0.2 ppm, or 0.1 ppm indicates that the pharmaceutical composition is suitable for administration to an animal IX. Articles of Manufacture and Kits The polypeptides purified by the methods described herein and/or formulations comprising the polypeptides purified by the methods described herein may be contained within an article of manufacture. In some embodiments, the article of manufacture comprises antibodies generated using the ultrapure DsbA and/or DsbC polypeptides described herein. The article of manufacture may comprise a container containing the polypeptide, antibody, polypeptide formulation, and/or the antibody formulation. Preferably, the article of manufacture comprises: (a) a container comprising a composition comprising the polypeptide, antibody, polypeptide formulation, and/or the antibody formulation described herein within the container; and (b) a package insert with instructions for using the polypeptides and/or antibodies.

The article of manufacture comprises a container and a label or package insert on or associated with the container. Suitable containers include, for example, bottles, vials, syringes, etc. The containers may be formed from a variety of materials such as glass or plastic. The container holds or contains a formulation and may have a sterile access port (for example the container may be an intravenous solution bag or a vial having a stopper pierceable by a hypodermic injection needle). The article of manufacture may further include other materials desirable from a commercial and user standpoint, including other buffers, diluents, filters, needles, and syringes. In some embodiments, the container is a syringe. In some embodiments, the syringe is further contained within an injection device. In some embodiments, the injection device is an autoinjector.

A "package insert" is used to refer to instructions customarily included in commercial packages of therapeutic products, that contain information about the uses of the polypeptide, antibody, polypeptide formulation, and/or the antibody formulations.

In some embodiments, the invention provides kits for the detection of DsbA in a pharmaceutical composition comprising a recombinant polypeptide prepared from a bacterial cell, wherein the kit comprises an anti-DsbA antibodies as described herein. In some embodiments, the invention provides kits for the detection of DsbC in a pharmaceutical composition comprising a recombinant polypeptide prepared from a bacterial cell, wherein the kit comprises anti-DsbC antibodies as described herein. In yet other embodiments, the invention provides kits for the detection of DsbA and DsbC in a pharmaceutical composition comprising a recombinant polypeptide prepared from a bacterial cell, wherein the kits comprise anti-DsbA antibodies as described herein and anti-DsbC antibodies as described herein. In some embodiments, the invention provides kits for the detection of DsbA in a pharmaceutical composition comprising a recombinant polypeptide prepared from a bacterial cell, wherein the bacterial cell (e.g., an *E. coli* cell) overexpresses DsbA and/or DsbC. In some embodiments, the kits include instructions for use. In some embodiments, the kits further comprise ultrapure DsbA and/or DsbC for use as a reference standard in generating standard curves for quantitating DsbA and/or DsbC in a sample. In some embodiments, the kits further comprise ultrapure DsbA and/or DsbC for use as positive controls in an assay to detect DsbA and/or DsbC in a sample.

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

Further details of the invention are illustrated by the following non-limiting Examples. The disclosures of all references in the specification are expressly incorporated herein by reference.

EXAMPLES

The examples below are intended to be purely exemplary of the invention and should therefore not be considered to limit the invention in any way. The following examples and detailed description are offered by way of illustration and not by way of limitation.

Example 1. Assay for *E. coli* Protein does not Adequately Measure DsbA or DsbC

Disulfide oxidoreducatase (DsbA) is a strong oxidant that can oxidize the cysteines in a protein by a thiol disulfide exchange reaction to form disulfide bonds. It is a primary catalyst of disulfide bond formation in bacteria and promotes the correct protein folding of protein. Similarly, Disulfide oxidoreducatase (DsbC) is a disulfide bond isomerase during oxidative protein-folding in cell's periplasm. DsbA and DsbC are typically not expressed at high levels in *E. coli*, but *E. coli* overexpressing DsbA and/or DsbC have been used to improve the proper assembly and folding of heteromultimeric eukaryotic proteins including antibodies (e.g., multispecific antibodies).

To determine if the assay for *E. coli* protein (ECP) can adequately detect and quantitate the presence of DsbA and/or DsbC, samples of purified DsbA or DsbC were added to assay diluent (0.15M NaCl/0.1 M NaPO$_4$/0.1% fish gelatin/0.05% Poly sorbate 20/0.05% Proclin 300) at different concentrations and tested in the ECP assay (Zhu-Shimoni, J. et al., 2014, *Biotech and Bioeng*. 111:2367-2379). Bovine serum albumin was used as a negative control as an assay for *E. coli* protein should not detect this mammalian protein. Results are shown in Table 3.

TABLE 3

ECP assay detection.

| DsbA | | | DsbC | | |
|---|---|---|---|---|---|
| Theoretical (μg/mL) | Theoretical (μg/mL) | Observed (μg/mL) | Theoretical (μg/mL) | Observed (μg/mL) | % Recovery |
| 3530.0 | 3100.0 | 140.0 | 3100.0 | 140.0 | 4.5 |
| 1765.0 | 1550.0 | 109.1 | 1550.0 | 109.1 | 7.0 |
| 882.5 | 775.0 | 78.1 | 775.0 | 78.1 | 10.1 |
| 441.3 | 387.5 | 54.1 | 387.5 | 54.1 | 14.0 |
| 220.6 | 193.8 | 36.8 | 193.8 | 36.8 | 19.0 |
| 110.3 | 96.9 | 25.1 | 96.9 | 25.1 | 25.9 |
| 55.2 | 48.4 | 15.5 | 48.4 | 15.5 | 32.0 |
| 27.6 | 24.2 | LTR | 24.2 | LTR | |

| Bovine Serum Albumin | | |
|---|---|---|
| Theoretical (μg/mL) | Observed (μg/mL) | % Recovery |
| 2000.0 | LTR | |
| 1000.0 | LTR | |
| 500.0 | LTR | |
| 250.0 | LTR | |
| 125.0 | LTR | |
| 62.5 | LTR | |
| 31.3 | LTR | |
| 15.6 | LTR | |

LTR = less than range

The results show that the ECP assay does not adequately detect and quantitate DsbA or DsbC. Further, commercial assays to detect *E. coli* remnants (e.g., *E. coli* proteins and nucleic acids) as part of release assays for therapeutic proteins prepared in *E. coli* do not identify DsbA and/or DsbC because these assays are typically generated by making polyclonal antibodies to *E. coli* cell extracts where DsbA and/or DsbC expression is minimal. As such, there is a need to prepare ultrapure DsbA and/or DsbC to generate polyclonal antibodies that are highly specific to Dsb A and/or DsbC with minimal reactivity to other *E. coli* proteins and/or nucleic acid that could interfere with DsbA and/or DsbC detection assays. In addition, ultrapure preparations of DsbA and/or DsbC are useful in the generation of DsbA and/or DsbC standards for accurate detection of DsbA and/or DsbC in a therapeutic polypeptide preparation and in the generation of DsbA and/or DsbC positive controls to insure assay quality for research and commercial polypeptide production.

Example 2. Purification of Ultrapure DsbA

Materials and Methods
Extraction Step

DsbA was expressed in *E. coli* (W3110 derivative named 62A7 ΔfhuA (ΔtonA) ptr3, lacIq, lacL8, ompTΔ(nmpc-fepE) ΔdegP ilvG repaired) (Joly, J C and Swartz J R 1994, *Biochem*. 33:4231-4236; Joly, J C and Swartz J R 1997, *Biochem*. 36:10067-10072; U.S. Pat. No. 5,789,199). The cell paste was suspended (50 g cell paste/1 L) in 10 mM MOPS pH 7.1 and mixed until the suspension was homogenous. Cell lysis was performed using a Microfluidizer 110F at 7000 psi. The homogenate was conditioned to 0.1% PEI (using a 10% PEI stock solution) and mixed for 30 min at ambient temperature (~21° C.). The suspension was centrifuged at 8500 rpm for 30 min. The centrate was collected and filtered through a 0.22 um Durapore filter.

Purification Method

All column chromatography steps were performed on AKTA Explorers from GE. The DsbA was extracted from *E. coli* cell paste using homogenization and centrifugation. The centrate was purified by anion exchange chromatography in bind and elute mode using a Q Sepharose® FF (QSFF) column. The QSFF pool was then purified by cation-exchange chromatography in bind and elute mode using a Poros 50 HS column. The detailed running conditions are described in Tables 4 and 5.

Q-Sepharose® Step
Mode: Bind and Elute; Resin: Q-Sepharose FF (GE); Column Height: 20-30 cm; Flow rate: 150 cm/h; Load density: ≤6 mg/mL).

TABLE 4

| QSFF Process | | |
|---|---|---|
| Step | Buffer | Column Volume |
| Pre Equil | 25 mM Tris, 1M NaCl, pH 9.2, 86 mS/cm | 4 |
| Equilibration | 25 mM Tris, pH 9.1, 0.3 mS/cm | 4 |
| Load | Dilute centrate with water (1:1), then pH-adjust to 9.0 with 1.5M Tris Base pH 9.0, conductivity ~1.0 mS/cm | <6 mg/mL |
| Wash | Equilibration Buffer | 6 |
| Elution | Buffer B: 25 mM Tris, 250 mM NaCl, pH 9.2, 26 mS/cm<br>1.) 15% B for 4 CV<br>2.) 20% B for 4 CV<br>3.) 25% B for remainder of elution phase Fraction collected peak (1 CV) QSFF Pool was pH-adjusted to 5.0 with 2.0M Acetic Acid | 20 |
| High Salt Wash | 25 mM Tris, 1M NaCl, pH 9.2, 86 mS/cm | 5 |
| Sanitization | 0.5N NaOH | ≥30 minutes |
| Storage | 0.1N NaOH | 3 |

Pooling: The pools were assayed by size exclusion chromatography (SEC) and pooled based on the fractions containing the largest amount of DsbA (data not shown).

Poros 50 HS Step
Mode: Bind and Elute; Resin: Poros 50 HS (Applied Biosystems); Column Height: 20-30 cm; Flow rate: 150 cm/h; Load density: ≤6 mg/mL).

TABLE 5

| Poros 50HS Process | | |
|---|---|---|
| Step | Buffer | Column volume |
| Equilibration | 2.5 mM MES, pH 5.5, 0.4 mS/cm | 4 |
| Load | Q Pool pH-adjusted to 5.0 with 2M Acetic Acid, then diluted with water (1:2) pH 5.0, 0.4 mS/cm | As required |
| Wash 1 | Equilibration Buffer | 5 |
| Elution | Buffer B: 12.5 mM MES, 250 mM NaCl pH 5.5, 25 mS/cm Gradient 0 to 60% B in 15 CV Fraction collected peak (1 CV) | 15 |
| High Salt | 12.5 mM MES, 1M NaCl, pH 5.5, 87 mS/cm | 5 |
| Sanitization | 0.5N NaOH | ≥30 minutes |
| Storage | 0.1N NaOH | 3 |

Figure 3:
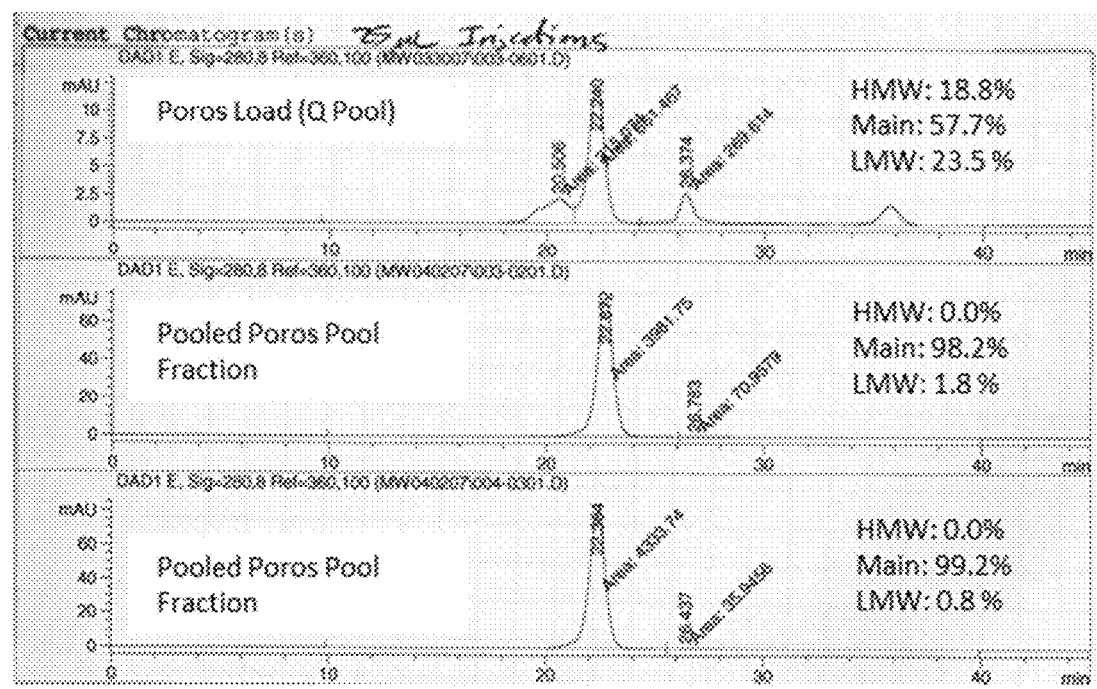
FIG. 3 shows chromatographs of size exclusion chromatography of Poros load and Poros pool fractions for the purification of DsbA.
Figure 4:
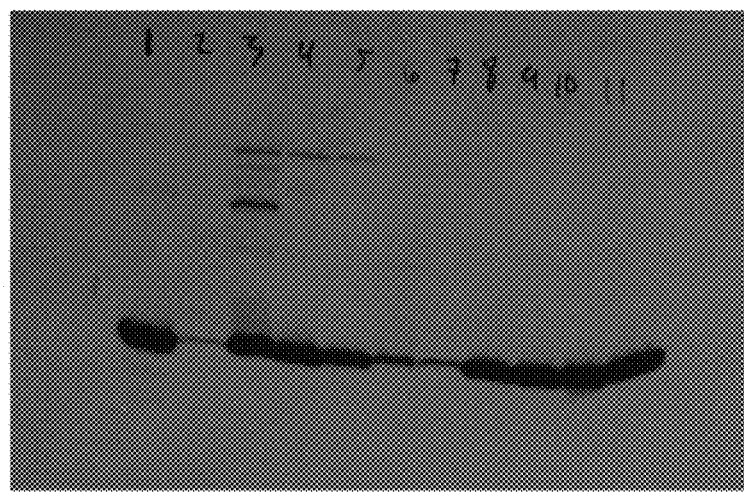
FIG. 4 shows a western blot of DsbA Poros HS pool fractions. The mock pool primarily contains the DsbA molecule.

Pooling: Fractions were analyzed and pooled based on purity by SDS-PAGE Gel and SEC (FIGS. 3 and 4).

Concentration of Poros 50 HS Pool

The pool was concentrated to ~3.0 mg/mL using 10 kD Centricon membranes (Millipore) that were centrifuged for ~30 min at 3000 rpm.

Analytical Methods

Titer Determination

DsbA centrate titer was quantified with a HPLC (Agilent 1100) assay using a Superdex 200 10/300 SEC column from GE Healthcare (ID #0619081). The column was run at 0.5 mL/min at ambient temperature. The column was equilibrated at 0.5 mL/min for 60 minutes with 0.20 M potassium phosphate, 0.25 M potassium chloride, pH 6.2±0.1. Absorbance was monitored at 280 nm and elution peak area was quantified. The absorbance was measured at 280 nm minus background absorbance at 320 nm using an extinction coefficient of 1.15 (mg/ml)–1*cm$^{-1}$.

Size Exclusion Chromatography (SEC)

DsbA heterogeneity, percent high molecular weight, monomer, and fragments were determined using a Superdex 200 10/300 SEC column from GE Healthcare (ID #0619081). The column was run at ambient temperature on an HPLC (Agilent 1100) at 0.5 mL/min for 60 minutes in 0.20 M potassium phosphate, 0.25 M potassium chloride, pH 6.2±0.1. The target injection volume was 50 µg and absorbance was monitored at 280 nm. The peak areas were calculated using Chemstation Software from Agilent.

SDS-PAGE

SDS-PAGE was performed with 4-12% Bis-Tris precast gels (Invitrogen Cat. # NP0322). The gels were stained using the Heukeshoven Silver Staining method.

Western Blot

Purified DsbA protein was generated. Rabbits were immunized and the final bleeds were pooled and affinity purified as described below.

For immunoblot analyses, proteins were transferred from SDS gels onto nitrocellulose membranes with a semi-dry transfer system (iBlot Invitrogen cat. # SD1000). The nitrocellulose was blocked using a 1×NET (A3017), 0.5% Gelatin (Bio-Rad Catalog No. 170-6539) solution for 30 minutes at room temperature. A primary anti-DsbA antibody was diluted 1:700K in 50 mL of 1×NET and added to the blocked nitrocellulose and probed overnight. Anti-DsbA antibody was produced by immunizing rabbits with purified DsbA. The rabbit antisera were pooled, affinity purified and stored in PBS, pH 7.5, containing 0.1% sodium azide]. A secondary anti-rabbit-HRP (GE Healthcare cat # NA934V) antibody was diluted 1:100K and added to washed nitrocellulose for two hours.

Results

DsbA was able to bind to the column using pH 9.0 buffers and load. The QSFF elution phase had three distinct elution peaks. Selected QSFF pool fractions across the elution peak were analyzed using a Superdex 200 10/300 GL SEC column (FIG. 1). The LMW impurities elute in the first peak (Fraction 3). The second peak is comprised predominantly of HMW species (Fraction 7), and the third peak contained the target DsbA protein (Fractions 10 and 11). The tail-eluting shoulder contained additional LMW species and trace amounts of DsbA (Fraction 15). The fractions containing the DsbA protein were pooled based on size exclusion chromatography data. The QSFF step provided partial reduction of HMW and LMW species; however, an additional downstream purification step was implemented to further improve the purity of the DsbA.

Figure 2:
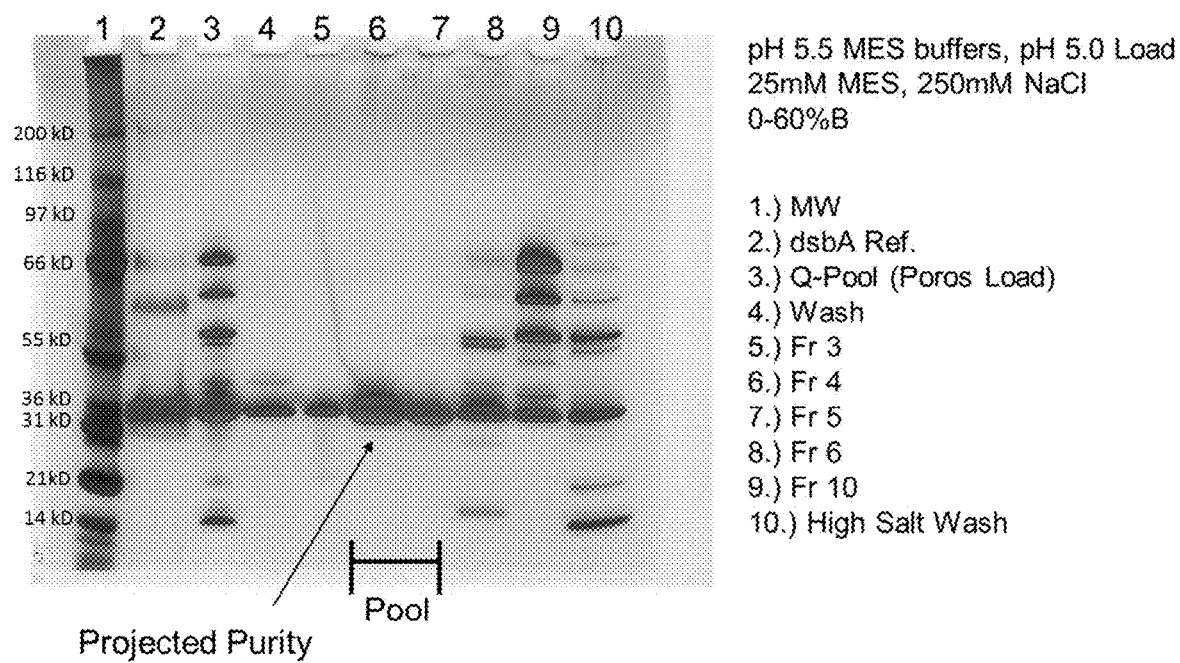
FIG. 2 shows SDS polyacrylamide gel electrophoresis (PAGE) of Poros HS pool fractions for the purification of DsbA.

The Poros 50 HS resin was implemented to purify the QSFF pool. SDS-PAGE analysis of the POROS 50 HS pool (Fractions 4 and 5) showed that the main peak contains the DsbA protein (FIG. 2, Lanes 6 and 7). The single band representing the purified DsbA protein has a molecular weight consistent with a previously purified pool of DsbA (Lane 2. The HMW and LMW species eluted later in the gradient and the high salt wash (Lanes 9 and 10). The SEC data from a representative Poros 50 HS run is shown in FIG. 3. The pooled Poros 50HS fractions (Fractions 4 and 5) showed that HMW and LMW were removed from the load and the fractions consisted primarily of DsbA protein. No aggregation issues were observed with the purified DsbA material.

The chromatography process resulted in ultrapure DsbA. The DsbA was >98% as shown in FIG. 4—98.2% main peak as analyzed by SEC with 0.0% HMW species and 1.8% LMW species and 99.2% main peak as analyzed by SEC with 0.0% HMW species and 0.8% LMW. Impurities were quantitated by SEC shown with the Poros Load (Q Pool) in FIG. 3.

Example 3. Purification of Ultrapure DsbC

DsbC was previously purified using a two-step chromatography process (Table 6; Process A). The protein was needed in order to generate a reference standard for ELISA (enzyme-linked immunosorbent assay) development and as an immunogen to generate antibodies against DsbC (in rabbits) for use as molecular probes.

Figure 5:
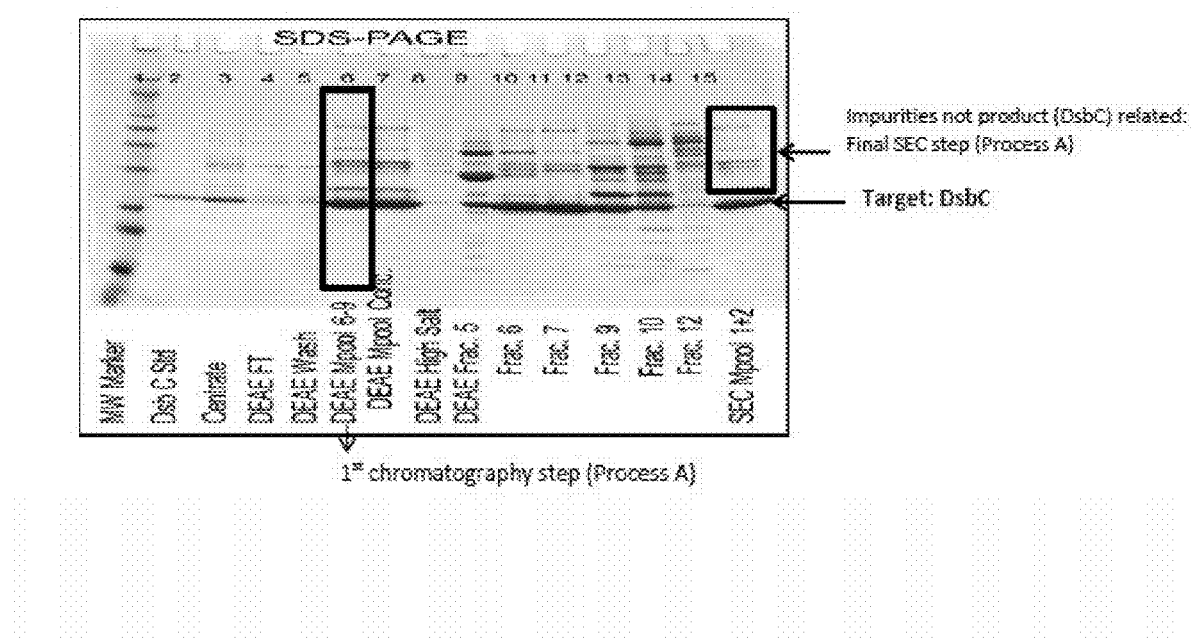
FIG. 5 is SDS polyacrylamide gel electrophoresis of fractions for the purification of DsbC.

The purified DsbC bulk from the two-step process was analyzed by Western Blot against a commercially available rabbit anti-DsbC. SDS-PAGE analysis revealed that the DsbC contained several higher molecular weight (HMW) host cell-related proteins (FIG. 5). Because of these impurities, new DsbC material was generated to provide a higher level of DsbC purity, in order to minimize the generation of rabbit antibodies against host cell protein impurities, which might result in an over-quantitation of the level of DsbC in samples being measured in the ELISA.

In order to accomplish this desired level of purity, several different chromatographic steps (as well as their relative positioning in the purification process) were evaluated. Different processes were evaluated for relative performance to generate material suitable for use as a reference and as an immunogen (Table 6).

TABLE 6

| | DsbC Purification Process | | | | |
|---|---|---|---|---|---|
| | Process A (original) | Process B | Process C | Process D | Process E (final) |
| Extraction | | | Cell paste resuspension | | |
| | | | Cell lysis | | |
| | | | Cation polymer/dilution | | |
| | | | centrifugation | | |

TABLE 6-continued

| | DsbC Purification Process | | | | |
|---|---|---|---|---|---|
| | Process A (original) | Process B | Process C | Process D | Process E (final) |
| Chromatography 1 | Weak anion exchange (AE): DEAE FF | Weak AE | Weak AE | Weak AE | Weak AE |
| Chromatography 2 | N/A | Strong cation exchange (CE): SPFF | Strong CE | Hydrophobic Interaction chromatography (HIC): Phenyl FF (low sub) | Hydrophobic Interaction chromatography (HIC): Phenyl FF (low sub) |
| Chromatography 3 | N/A | N/A | Hydrophobic Interaction chromatography (HIC): Phenyl FF (low sub) | N/A | N/A |
| Final Chromatography/ Buffer Exchange | Size Exclusion Chromatography (SEC): Superdex 200 | N/A | N/A | N/A | Size Exclusion Chromatography (SEC): Superdex 75 |

Cell Extraction

E. coli (a W3110 derivative named 62A7 AfhuA (AtonA) ptr3, lacIq, lacL8, ompTΔ(nmpc-fepE) ΔdegP ilvG repaired) (Joly, J C and Swartz J R 1994, Biochem. 33:4231-4236; Joly, J C and Swartz J R 1997, Biochem. 36:10067-10072; U.S. Pat. No. 5,789,199) cell paste (containing DsbC) was suspended in lysis buffer (10 mM MOPS, pH 7.0; 1 gram of cell paste per 10 mL of lysis buffer). Cell lysis was performed (4 passes at 7-8 K psi) using a Microfluidizer® (Microfluidics). Polyethyleneimine (PEI; a flocculent) was added to the lysate to a final concentration of 0.1% (m/v) and then mixed for 30 min at room temperature. The PEI suspension was centrifuged (10 K rpm, 45 min, 18° C.) and the supernatant was collected and filtered through a 0.22 µm filter prior to chromatography.

Purification: Process A

A total of 1.8 L of clarified centrate (conditioned with 1.5 M Tris base to pH 8.0) was loaded to a column containing DEAE Sepharose® Fast Flow (GE Healthcare) in bind and elute mode as described in Table 7. At the end of this step, 694 mg protein containing DsbC was recovered.

TABLE 7

| Process A DEAE Sepharose ® Fast Flow Chromatography | | | |
|---|---|---|---|
| Step | Buffer | Volume used (CVs) | Flow Rate (mL/min) |
| Pre-equil. | 250 mM MOPS pH 7.1; cond. 6.2 mS/cm) | 3 | 13.3 |
| Equilibration | A = 10 mM MOPS pH 7.1; cond. 0.3 mS/cm) | 3 | 13.3 |
| Load | Clarified centrate (conditioned to pH 8) | 1.77 L | 13.3 |
| Wash | Equil. Buffer | 12 | 13.3 |
| Elution Gradient (A) | 10 mM MOPS pH 7.1; cond. 0.3 mS/cm) | 0-60% B for 15 CVs | 13.3 |
| Elution Gradient (B) | 10 mM MOPS, 250 mM NaCl pH 7.0; cond. 25 mS/cm) | | 13.3 |
| High Salt Wash | 10 mM MOPS, 1M NaCl pH 7.0; cond. ~86.7 mS/cm) | 5 | 13.3 |
| Regen/Storage | 0.5N NaOH/0.1N NaOH | 5/5 | 13.3 (30 min. exposure) |

Figure 6A:
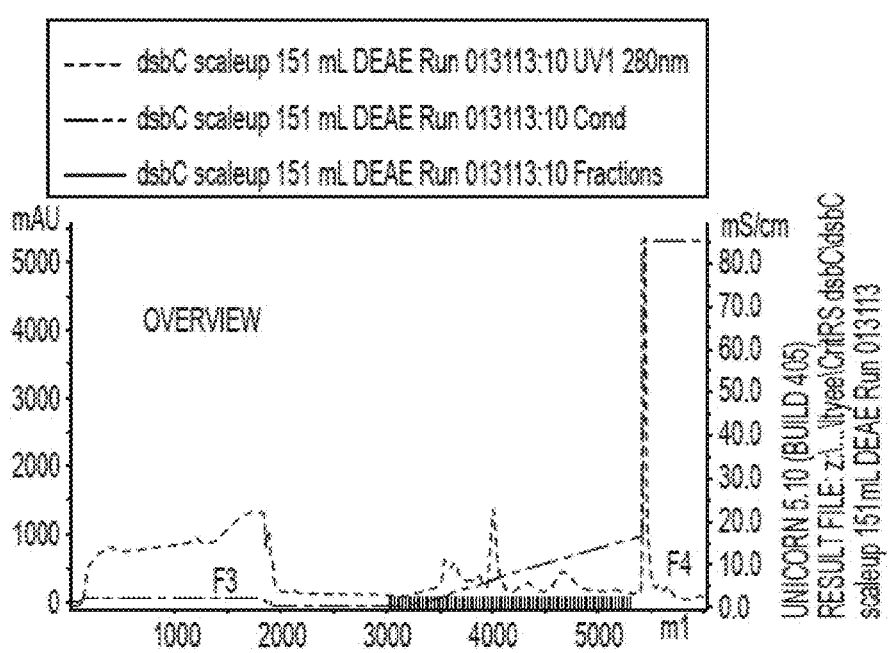
FIG. 6A shows a chromatogram of DEAE FF chromatography for purification of DsbC.
Figure 6B:
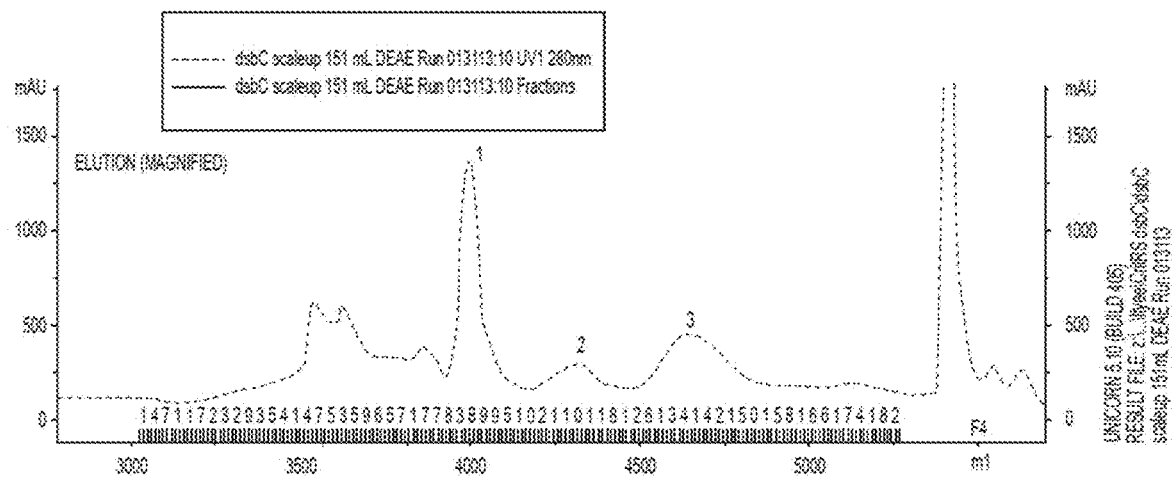
FIG. 6B shows a magnification of the elution portion presented in FIG. 6A.
Figure 7:
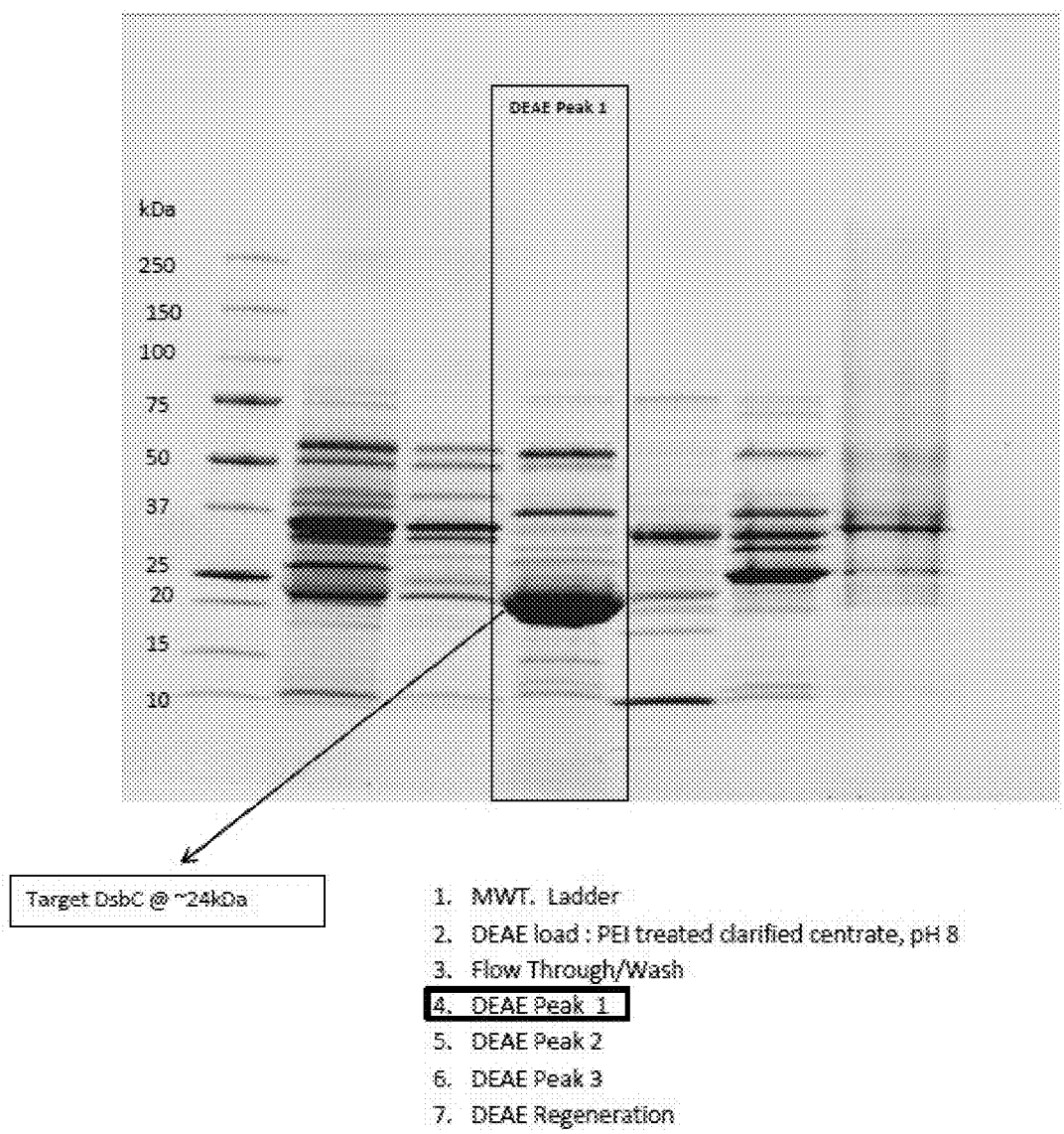
FIG. 7 shows SDS PAGE of DEAE-FF fractions for the purification of DsbC.
Figure 8A:
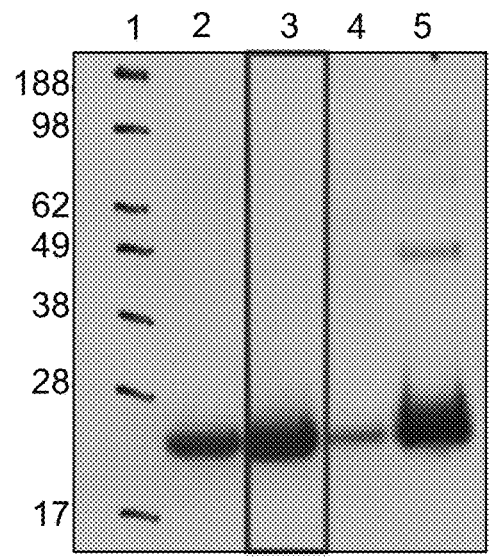
FIGS. 8A and 8B show electrophoresis of chromatography samples in the purification of DsbC.
Figure 8B:
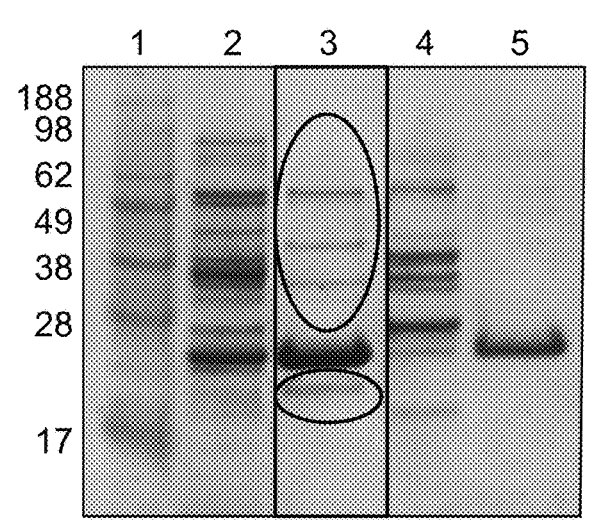

The elution profile for the DEAE Sepharose Column® is shown in FIG. 6. SDS-PAGE analysis (FIG. 7) of the peaks labelled as 1, 2 and 3 indicates that the fractions in Peak 1 contain a prominent band corresponding to the predicted molar mass 24 kDa) of DsbC. The Peak 1 fractions were pooled and then immuno-blotted against rabbit anti-DsbC. The results of this immunoblot (FIG. 8A) confirmed the presence of DsbC. The SDS-PAGE analysis reveals a number of higher molecular weight and lower molecular weight bands that do not light up in the immunoblot, indicating that they are not related to DsbC and are host-cell related impurities (FIG. 8B). The size-exclusion chromatography (SEC) from the original process (Process A) would be able to remove some, but not all, of these impurities, as proteins that have molar masses close to that of DsbC would not be sufficiently separated. Alternate means to for downstream purification were evaluated to see which method(s) and step order(s) would be effective in purification of DsbC to the required level of purity for the target indications (outlined in refer to the Reagent Background section).

Purification: Process B

The strong cation exchange chromatography media, SP Sepharose® Fast Flow, (SP-FF; GE Healthcare), was evaluated for the removal of the host cell proteins from the DEAE Sepharose® Fast Flow chromatography pool.

The screening of SP Sepharose FF was carried out at pH values of 5.0, 5.5 and 6.0. Loading density was 5 mg/mL. Buffers were as follows: A. Equilibration/wash buffer: pH 5 was 50 mM NaOAc, 3.1 mS/cm; pH 5.5 was 50 mM NaOAc, 3.05 mS/cm; pH 6 was 20 mM phosphate, 3.18 mS/cm; B. Elution Buffer: pH 5 was 1 M NaCl in Equil A, 94 mS/cm; pH 5.5 was 1 M NaCl in Equil A, 92 mS/cm; pH 6 was 1 M NaCl in Equil A, 87 mS/cm. Three drip columns were set up, each containing 1 mL SPFF resin and tested at the appropriate pH ranges. Columns (PD10 columns, Sephadex 25) were equilibrated with 10 CV equilibration buffer. Load was DEAE Pool that had been buffered exchanged with the appropriate SP equilibration buffer at pH 5, 5.5 and 6. Columns were washed with 7 CV wash buffer. Elution was with 5 CV each of 10% B, 20% B, 40% B, 60% B, 80% B, and 100% B.

The column fractions for each of the pH values tested were evaluated by SDS-PAGE. The best binding condition was observed at pH 5.0. Increasing pH values resulted in some-to-all of the buffer-exchanged DEAE-FF pool flowing through the columns. Some, but not all, of the host cell impurities were removed at pH 5.0: a single lower molecular weight band of ~20 kDa was removed during the column loading.

Increasing the NaCl concentration to 100 mM resulted in the incomplete elution of DsbC, but removed several higher MW bands. An increase in NaCl to 200 mM eluted the majority of the remaining DsbC, but also eluted several other protein impurities.

Figure 9:
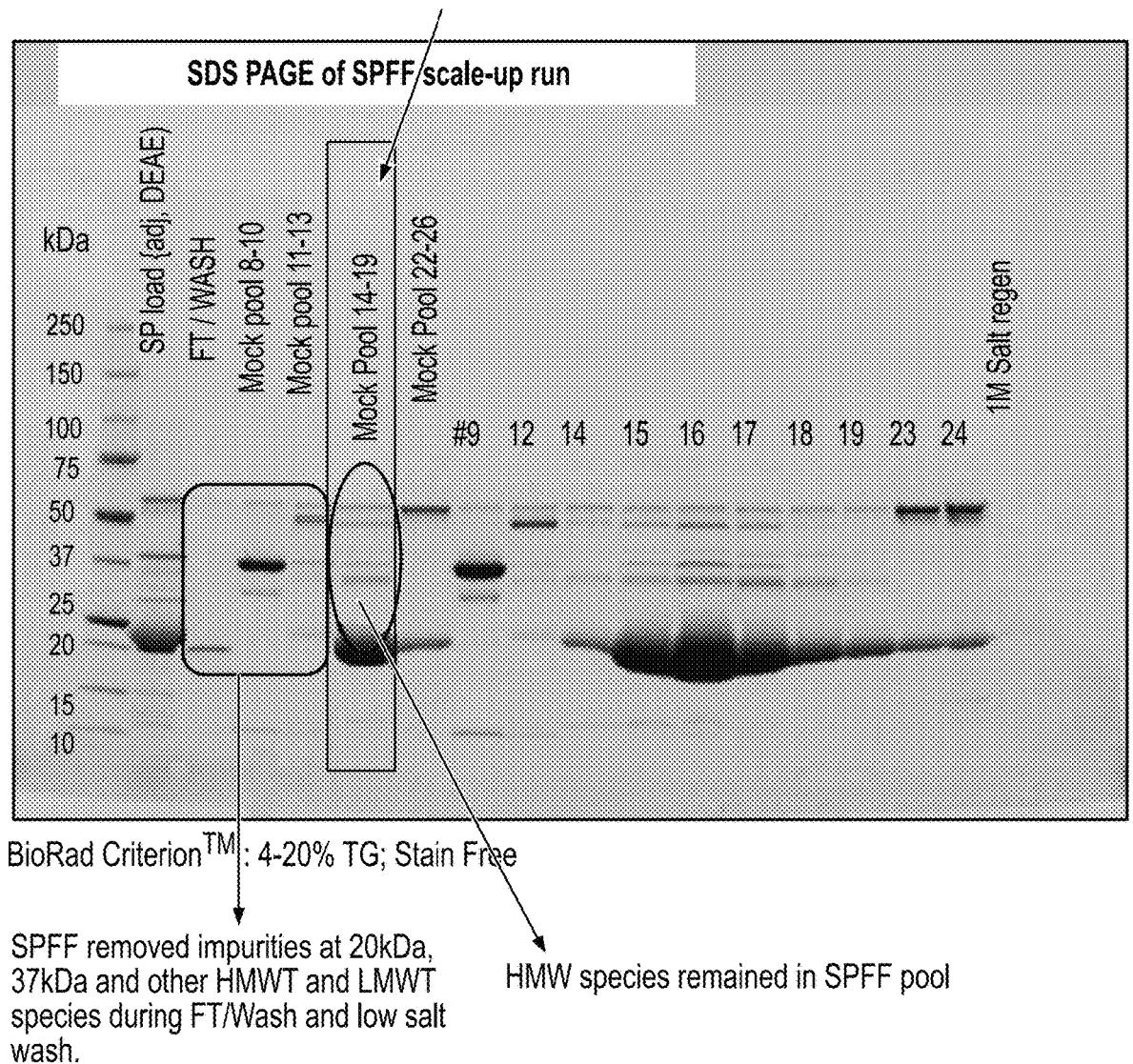
FIG. 9 shows SDS-PAGE of SPFF fractions.

The initial results on SP-FF warranted further evaluation of SP-FF at pH 5.0. In order to evaluate the potential of SP-FF to remove residual host cell protein impurities Small scale purification was carried out using the following parameters: The clarified centrate was loaded to a column containing SP Sepharose® Fast Flow in bind and elute mode as described in Table 8. Analysis of the SP-FF column fractions showed the same removal of the 20 kDa impurity that was seen in the initial evaluation, as well as the removal of a band at 37 kDa that eluted earlier in the gradient (FIG. 9). The DsbC fractions showed increased purity from this chromatography step, but still contained residual higher MW impurities and trace amounts of lower MW impurities (FIG. 9). Analysis of the pooled SP-FF fractions by HPLC-SEC showed 95.2% main peak, 0.8% HMW species and 4.0% LMW species. Since the SP-FF gel did not remove the remaining impurities to sufficient levels, other methods of purification were evaluated.

TABLE 8

SP Sepharose Fast Flow chromatography

| Step | Buffer | Volume used (CVs) | Flow Rate (mL/min) |
|---|---|---|---|
| Equilibration | A = 50 mM NaOAc pH 5.0; cond. 3.5 mS/cm) | 7 | 0.85 |
| Load | pH adjusted DEAE pool to pH 5.0 using NaOAc, pH 5.0 (1:1), and then further diluted with purified water until conditioned., reached ~4 mS/cm. | all | 0.85 |
| Wash | Equilibration Buffer | 7 | 0.85 |
| Elution Gradient (A) | Equilibration Buffer | 0-60% B for 20 CVs | 0.85 |
| Elution Gradient (B) | 50 mM NaOAc, 1M NaCl, pH 5.0; cond. 88 mS/cm Gradient elution: 0-60% B in 20 CV; fractionate across elution gradient | | 0.85 |

TABLE 8-continued

SP Sepharose Fast Flow chromatography

| Step | Buffer | Volume used (CVs) | Flow Rate (mL/min) |
|---|---|---|---|
| High Salt Wash | 50 mM NaOAc, 1M NaCl pH 5.0; cond. 88 mS/cm | 5 | 0.85 |
| Regen/Strorage | 0.5N NaOH/0.1N NaOh | 5/5 | 13.3 (30 min. exposure) |

Purification: Process C

Hydrophobic interaction chromatography (HIC) was evaluated for the removal of the remaining impurities in the SP-FF pool. In developing Process C, five potential HIC media (Hi Propyl, Phenyl Sepharose® 6 Fast Flow (low substitution), Phenyl Sepharose® 6 Fast Flow (high substitution), Butyl Sepharose® 4 Fast Flow, and Octyl Sepharose® 4 Fast Flow) were evaluated using the same 1.0 mL column process as outlined for the initial evaluation of SP-FF (Process B, above). The chromatography conditions are detailed in Table 9.

TABLE 9

Process C: DEAE-SPFF-HIC

| HIC resin screens | Format: Gravity (drip method) Loading density: 3 mg/mL |
|---|---|
| HIC resins | 1. Hi Propyl<br>2. Phenyl Sepharose 6 Fast Flow (low-sub)<br>3. Phenyl Sepharose 6 Fast Flow (hi-sub)<br>4. Butyl Sepharose 4 Fast Flow<br>5. Octyl Sepharose 4 Fast Flow |
| Buffers | Equilibration/wash: 0.6M Sodium sulfate + 50 mM phosphate, pH 7<br>Elution: 0.5M Sodium sulfate + 50 mM phosphate, pH 7<br>0.4M Sodium sulfate + 50 mM phosphate, pH 7<br>0.3M Sodium sulfate + 50 mM phosphate, pH 7<br>0.2M Sodium sulfate + 50 mM phosphate, pH 7<br>0.1M Sodium sulfate + 50 mM phosphate, pH 7<br>Purified water (pw) |
| Protocol | 5 drip columns set up containing 0.5 mL appropriate HIC resin to test |
| | Equilibration of column: 10 CV |
| | Load: 7.5 mg of SPFF pool was diluted to contain a final concentration of 0.6M sodium sulfate, 50 mM phosphate, pH 7<br>Used 1.2M sodium sulfate and 1M phosphate pH 7 stock solutions for dilution<br>Adjusted final pH to 7, 68 mS/cm<br>Divided the load in to 5. The loading density for each resin was 3 mg/mL |
| | Wash: 7 CV (wash 1 (4 CV), wash 2 (3 CV)) |
| | Elution (3 CV of each): 0.5M Sodium sulfate + 50 mM phosphate, pH 7<br>0.4M Sodium sulfate + 50 mM phosphate, pH 7<br>0.3M Sodium sulfate + 50 mM phosphate, pH 7 |

TABLE 9-continued

Figure 10:
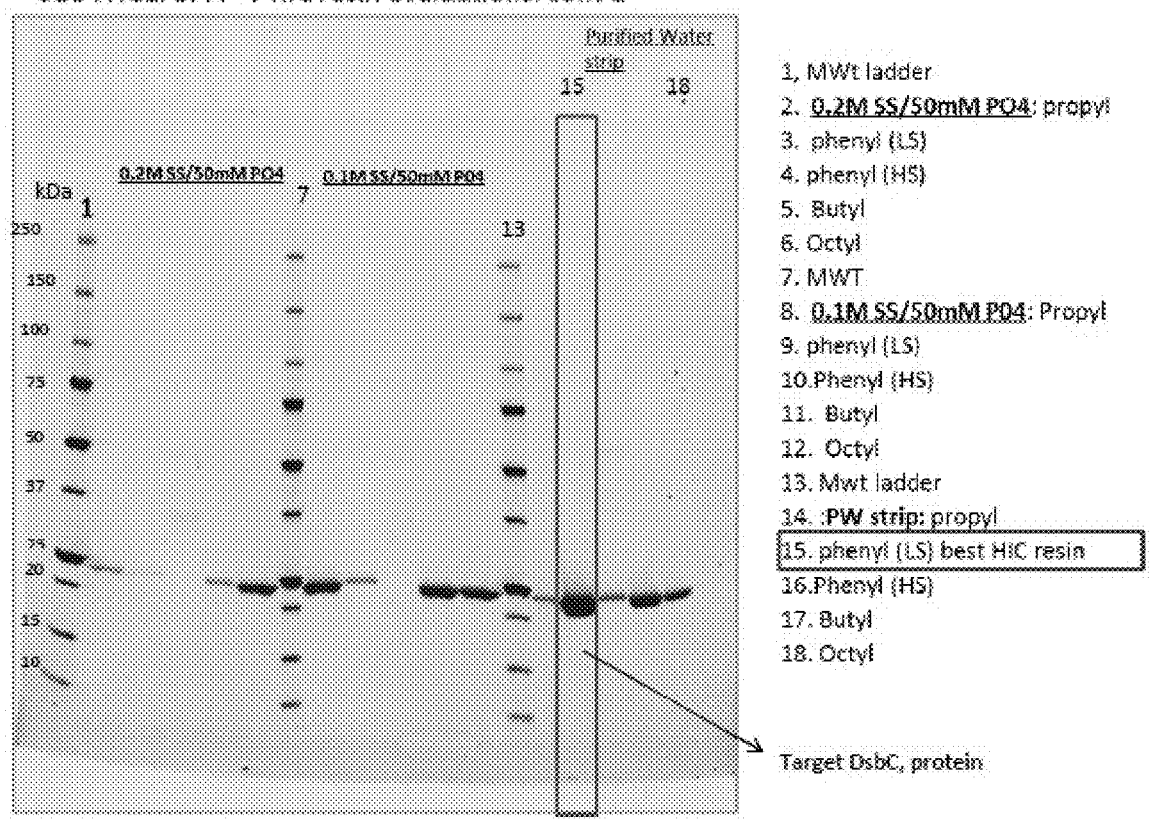
FIG. 10 shows SDS-PAGE used in screening HIC chromatographies for the purification of DsbC.

Process C: DEAE-SPFF-HIC 0.2M Sodium sulfate + 50 mM phosphate, pH 7
0.1M Sodium sulfate + 50 mM phosphate, pH 7
Purified water (pw)
Collect fraction and perform SDS PAGE to assess impurities removal Analysis of the column fractions by SDS-PAGE showed that, for most of the HIC media evaluated, the majority of the host cell impurities did not bind to the gels and were removed during the load and the wash step. Additional impurities showed differences in binding to these HIC media, but were successfully removed using a decreasing salt gradient (0.5 M sodium sulfate to 0.1 M sodium sulfate in 50 mM sodium phosphate, pH 7.0; (FIG. 10). DsbC was subsequently eluted from each of the HIC media with purified water (PW). SDS-PAGE results show that the greatest amount of purified DsbC is found in the Phenyl Sepharose® FF (low substitution) pool (FIG. 10).

Purification: Process D

The order of the three chromatography steps in Process C was extremely effective in removing residual host cell impurities present in the initial DEAE-FF step to yield very ultrapure DsbC. Further evaluations were carried out to see whether the HIC step was sufficiently robust to remove the host cell impurities from the DEAE-FF pool, eliminating the SP-FF step and effectively streamlining the purification process for DsbC.

To evaluate the HIC step in the second position, an aliquot of the DEAE-FF pool was conditioned and processed using the developed HIC conditions (Table 6, Process C). A further refinement to the HIC process included replacing intermediate wash steps with a longer 0.1 M sodium sulfate, 50 mM sodium phosphate wash step. The additional wash volume was implemented to remove the impurities from the column prior to eluting the DsbC with PW.

To evaluate the HIC step at the 3rd position, the same experimental strategy was performed as listed above, using the strong SP-FF pool instead of the DEAE-FF pool. These experiments were done as follows:

Experimental scheme: HIC at position 2—DEAE pool>HIC
  HIC at position 3—DEAE pool>SPFF pool>HIC
  Format: gravity (drip method)
  HIC resin: Phenyl Sepharose 6 Fast Flow (LowSub)
  Loading Density: 5 mg/ml
  Buffers:
  Equilibration/Wash 1: 0.6 M Sodium sulfate+50 mM phosphate, pH 7
  Wash 2: 0.1 M sodium sulfate+50 mM phosphate, pH 7
  Elution: PW (purified water)
  Two drip columns were set up, each containing 1 mL HIC resin
Equilibration (column): 10 column volumes (CV)
  Load: HIC at position 2: took 5 mg DEAE pool and diluted it to contain a final concentration of 0.6 M sodium sulfate/50 mM phosphate, pH 7. Adjusted to final pH 7; ~68 mS/cm.
    HIC at position 3: took 5 mg SPFF pool and diluted it to contain a final concentration of 0.6 M sodium sulfate/50 mM phosphate, pH 7. Adjusted to final pH 7; ~68 mS/cm.
  Wash 1: 5 CV
  Wash 2: 5 CV
  Elution: 3 CV
  Extra 3 CV
  Base regeneration: 0.1 N NaOH (2 CV)
  Collect fractions and performed SDS-PAGE to assess impurities removal.

Figure 11:
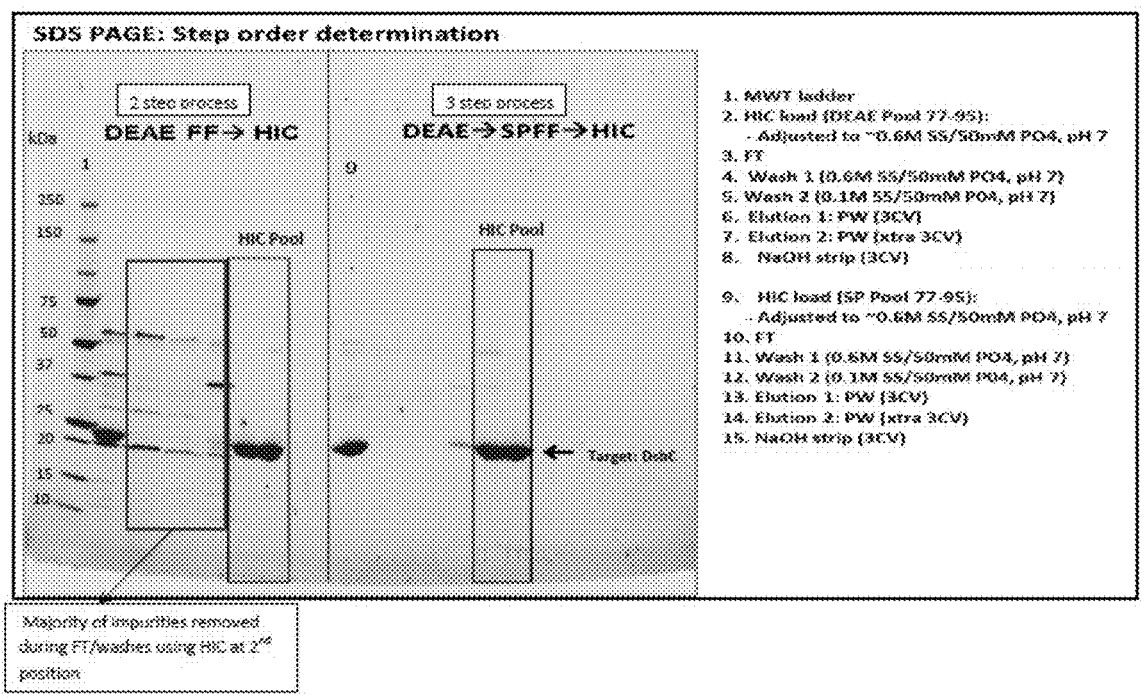
FIG. 11 shows SDS-PAGE used in screening HIC chromatographies for the purification of DsbC.

The two step process was just as effective in removing the undesired impurities from DsbC as was the three step process (FIG. 11).

Purification: Process E (Final Process)

Purification of the DEAE-FF pool was scaled up using Phenyl Sepharose® Fast Flow (low substitution). Table 10 lists the operating parameters. The main peak fractions were 7, 8, 9, 10 and 11 for the HIC step.

The column was Phenyl Sepharose (LS) in bind and elute mode. The mass loaded to the column was 536 mg.

TABLE 10

Phenyl Sepharose Fast Flow chromatography (low sub)

| Step | Buffer | Volume used (CVs) | Flow Rate (mL/min) |
|---|---|---|---|
| Equilibration | 0.6M sodium sulfate, 50 mM sodium phosphate, pH 7.0 | 10 | 13.2 |
| Load | Conditioned DEAE pool, diluted 1:1 with 1.2M sodium sulfate, 1:20 with 1M sodium phosphate and adjusted to pH 7.0, ~68 mS/cm prior to loading on HIC column. | all | 13.2 |
| Wash 1 | 0.6M sodium sulfate, 50 mM sodium phosphate, pH 7.0 | 7 | 13.2 |
| Wash 2 | 0.6M sodium sulfate, 50 mM sodium phosphate, pH 7.0 | 7 | 13.2 |
| Elution | Purified water, fractionate every 14 mL | 12 | 13.2 |

Figure 12:
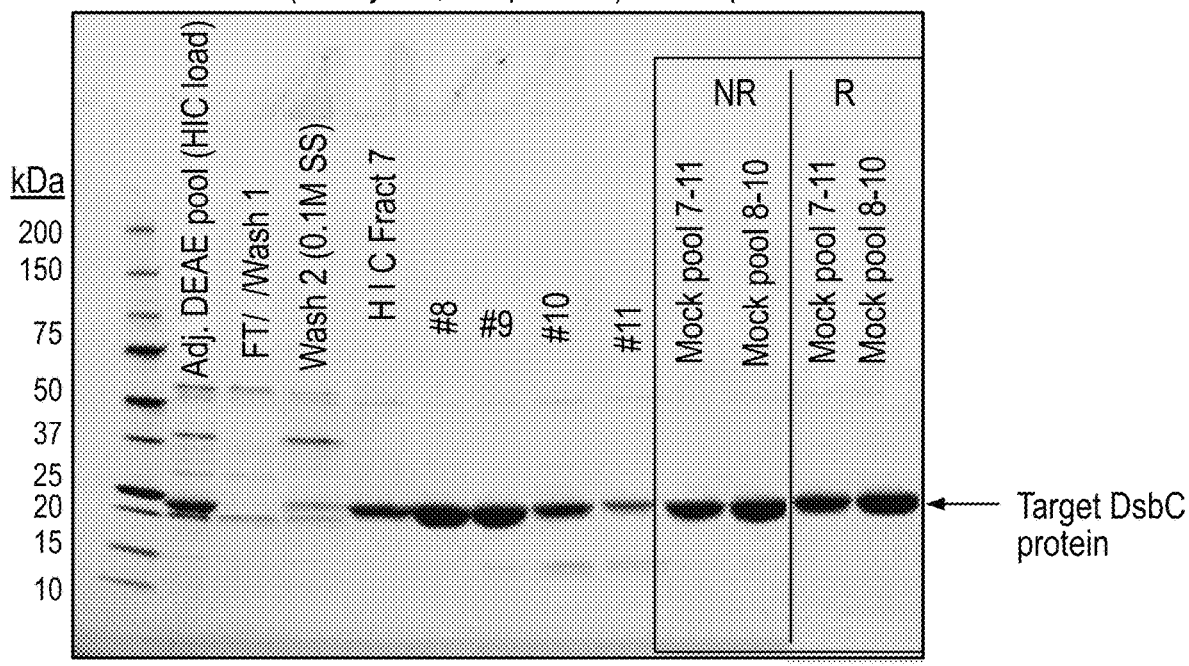
FIG. 12 shows SDS-PAGE of HIC chromatography fractions in the purification of DsbC.
Figure 13:
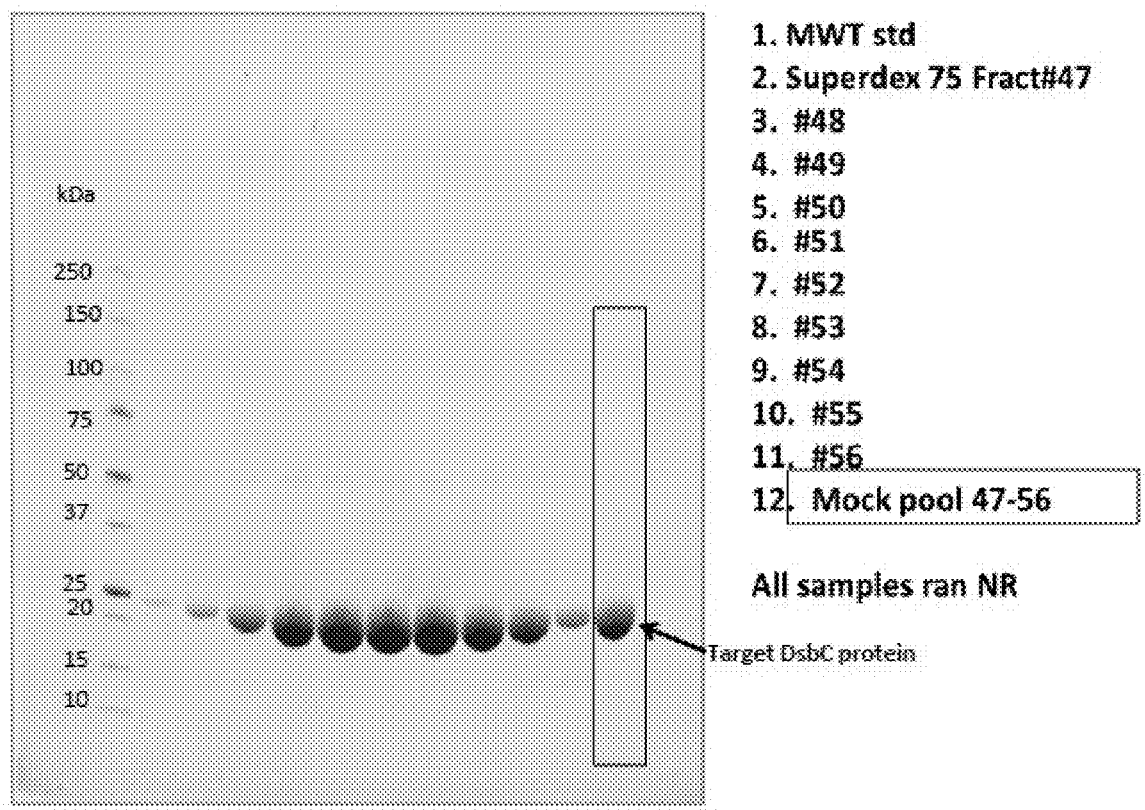
FIG. 13 shows SDS-PAGE of superdex 75 chromatography fractions of DsbC.

SDS-PAGE analysis of the column fractions showed very good impurities removal by the HIC step. Two faint bands (at 15 kDa and 50 kDa) were observed on some of the individual HIC fractions. However, when some or all of the main fractions were combined, only one band major band corresponding to DsbC was observed (FIG. 12). Analysis of the main DsbC fractions (7-11) using HPLC-SEC showed a distribution of 97.0% main peak, 1.0% low MW and 2.0% high MW. Taking a narrower cut (fractions 8-10) gave a distribution of 98.2% main peak, 1.7% low MW and 0.1% higher MW species.

Size Exclusion Chromatography (SEC), using Superdex 75 (GE Healthcare), was used to remove any residual high MW and low MW species and to formulate DsbC. Superdex 75 was chosen as its fractionation range (5 kDa to 70 kDa) is better suited to a smaller protein 24 kDa) like DsbC. Operating parameters for the SEC column are shown in Table 11.

In preparation for size-exclusion chromatography, the HIC pool (fractions 7-11) was concentrated to a volume of ≤16 mL (≤5% of the SEC CV) using Amicon Ultra-3 centrifugal filters (Millipore). The units were centrifuged at 4000 rpm using a clinical centrifuge (Eppendorf) for 20 min intervals until the target volume was reached.

TABLE 11

Superdex 75 size-exclusion chromatography

| Step | Buffer | Volume used (CVs) | Flow Rate (mL/min) |
|---|---|---|---|
| Equilibration | PBS, pH 7.0 ± 0.4 | 3 | 1 |
| Load | Concentrated HIC pool | ≤16 mL ≤5% of 1 CV | 1 |
| Elution | PBS, pH 7.0 ± 0.4 | 1 | 1 |

Figure 14:
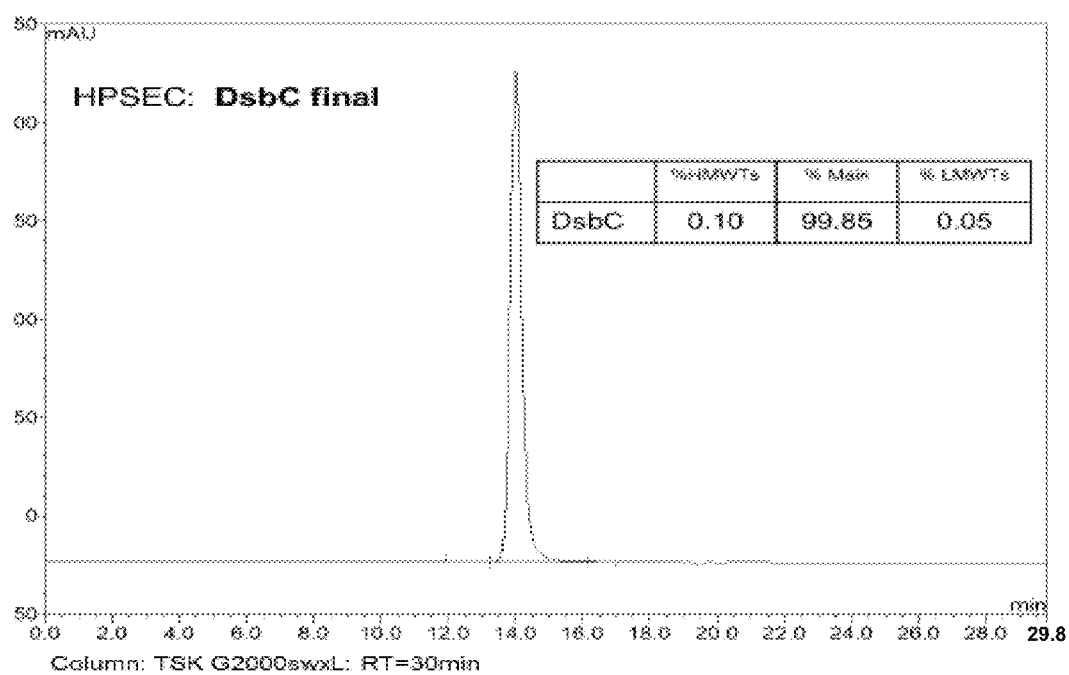
FIG. 14 shows a chromatogram showing High performance liquid chromatography (HPLC) of the formulated DsbC.

The concentrated HIC pool was loaded to the SEC column, and the load was chased with equilibration buffer. The column was developed with equilibration buffer and fractions representing 2% of the SEC CV (6.4 mL) were collected. A total of two size-exclusion runs were performed. The main fractions (47-56) were analyzed by SDS-PAGE (FIG. 13) and showed 1 major band corresponding to DsbC (~24 kDa). The same fractions were also tested in the HPLC-SEC assay. The final formulated DsbC bulk shows a single, highly symmetrical peak with slight tailing on the backside (FIG. 14). The preparative SEC step was successful in further removing impurities and buffer exchanging the DsbC bulk into the final formulation buffer; using HPLC-SEC showed a distribution of 99.85% main peak, 0.10% low MW and 0.05% high MW.

Freeze Thaw Stability and Analysis

The stability of the formulated bulk was evaluated by subjecting it to three freeze-thaw cycles at a temperature of ≤−80° C. Analysis of the freeze-thaw samples was done using SDS-PAGE and HPLC-SEC.

A total of 600 µL of the formulated bulk was used for this study, divided as four×150 µL aliquots for each time point. One aliquot was placed in cold room (2-8° C.) ("0" freeze-thaws). The remaining three aliquots were placed in the ≤−80° C. freezer. After 4 hours, the samples were thawed for ~1 hr at room temperature and gently mixed. One of the samples was transferred to the coldroom ("1" freeze-thaw) and the remaining samples were replaced in the ≤−80° C. freezer. This process was repeated, generating the "2" freeze-thaws sample. The remaining sample ("3" freeze-thaws) was stored overnight in the ≤−80° C. freezer. The "3" freeze-thaw sample was thawed on the next day. SDS-PAGE results run non-reduced and reduced show one band corresponding to DsbC (~24 kDa) on the purified bulk and on all freeze-thaw samples (data not shown). HPLC-SEC assay show all samples to be comparable, with overlapping profiles with 0.1% HMW species, 99.9% Main peak and no LMW species detected. The molecule retains its physical and functional properties after three freeze/thaw cycles.

SDS-PAGE and SyproRuby Staining

Figure 15:
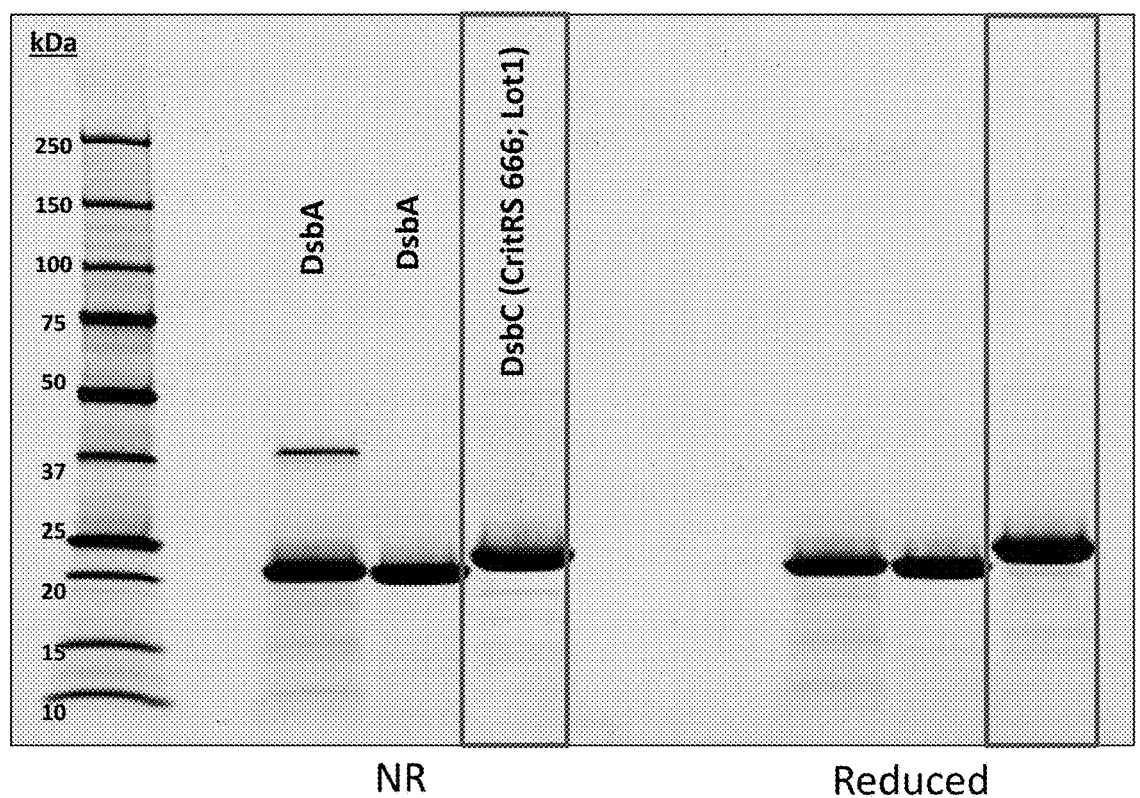
FIG. 15 shows SDS PAGE of DsbA and DsbC. Non-reduced samples are provided in the left columns Reduced samples are provided in the right columns.

In order to ensure that no other non-DsbC impurities were present in the final formulated bulk, SDS-PAGE was performed and imaged using SyproRuby staining (Bio-Rad; FIG. 15).

Functional Testing

The identity of the DsbC molecule was confirmed by a set of characterization assays (N-terminal sequence analysis, Peptide Mass Fingerprinting (PMF), intact/reduced Mass by CHIP TOF). The assays confirmed the correct identity of the molecule.

Functional testing of the aliquots of the purified DsbC bulk and the generated freeze-thaw samples was carried out and demonstrated comparability between the four samples, indicating that the protein was stable and functional over three freeze-thaws (data not shown). The purified DsbC was deemed as acceptable for rabbit immunizations to generate anti-DsbC antibodies and was later used to as the ligand for affinity chromatography to purify the anti-DsbC from rabbit anti-sera.

Example 4. Generation and Purification of Anti-DsbA and Anti-DsbC Antibodies

Polyclonal antibodies generated against ultrapure DsbA and DsbC were generated for use in assays to measure the removal from DsbA and DsbC in the preparation of therapeutic polypeptides. The following Example describes the purification methods used to generate the polyclonal DsbA and DsbC antibodies. These critical reagents, along with the DsbA and DsbC immunogens, were required for the development of the specific DsbA and DsbC ELISAs.

Three rabbits (per immunogen) were immunized with either DsbA or DsbC. At day 42, blood was drawn from individual rabbits and the DsbA and DsbC antisera was used for the purification of anti-DsbA and anti-DsbC antibodies.

Analytical Methods

Sodium dodecyl sulfate polyacrylamide gel electrophoresis (SDS-PAGE) was used to determine the relative purity of the DsbA and DsbC antibodies as well as to confirm the molar mass of the proteins. Electrophoresis was performed with and without disulfide bond reduction to assess for covalent aggregation of the antibodies.

SDS-PAGE was performed using Bio-Rad Criterion™ 4-20% TGX (Tris-Glycine eXtended) Stain-Free™ gels and imaged with a Bio-Rad Criterion Stain Free™ Imager (Bio-Rad Laboratories).

High Performance Liquid Chromatography-Size Exclusion Chromatography (HPLC-SEC) was used to monitor the size heterogeneity of DsbA and DsbC antibodies under native conditions using a TSK Gel 3000SW×1 column (Tosoh Bioscience) to separate high molecular weight (HMW) species, main peak (monomer), and low molecular weight (LMW) species.

Purification of DsbA and DsbC Antibodies

The purification of DsbA and DsbC antibodies were done in parallel using the same extraction and chromatography steps. The process consists of the following:

Salt precipitation: A 60% ammonium sulfate (AS) fractionation step was performed on the antisera. The 60% ammonium sulfate pellets are dissolved in a phosphate buffer prior to affinity chromatography.

Immobilized (immunogen) affinity chromatography: the affinity chromatography step was designed to separate the target antibodies from the remaining impurities in the 60% ammonium sulfate pellet. Purified DsbA and DsbC (the same lots of reagents that were used to immunize the rabbits) were used as ligands to construct separate affinity supports. Each affinity support was made by immobilization of the specific immunogen to activated Glyceryl-CPG (Controlled Pore Glass; Millipore) via reductive amination chemistry. This type of affinity chromatography gave a high degree of selectivity for the target antibodies.

Size-Exclusion Chromatography (SEC): preparative SEC was used to separate higher Molecular Weight (MW) and lower Molecular Weight (MW) species from the target antibodies and to formulate them into a suitable storage buffer. Functionality of the antibody pools was subsequently determined by their respective ELISAs to confirm the target assays performance.

The chromatographic steps performed and evaluated to generate material suitable for use in the development of the specific DsbA and DsbC ELISAs.

Precipitation of Antisera and Confirmation of Target Antibodies

Rabbit anti-sera A, B, C were pooled (volume=72 mL (anti-DsbA), 76 mL (anti-DsbC). 52 mL of ammonium sulfate conditioning solution (above) was slowly added to the anti-DsbA solution and 55 mL was added to anti-DsbC with gentle stirring throughout the addition. The solutions were centrifuged at 13,000 rpm, at a temperature of 18° C. for 45 minutes. The ammonium sulfate pellets (containing DsbA and DsbC antibodies) were frozen at ≤−60° C. until ready for affinity chromatography.

SDS-PAGE analysis of the ammonium sulfate suspensions, supernatants and pellets confirms that the supernatants have been depleted of the antibodies and the pellets contain all of the rabbit antibodies. The rabbit anti-DsbA and anti-DsbC antibodies show molar masses of ~130 kDa. Upon reduction, the main bands at ~130 kDa reduced to heavy chains (~50 kDa) and light chains (~25 kDa).

Affinity Chromatography

The anti-DsbA and anti-DsbC 60% ammonium sulfate pellets were reconstituted in phosphate buffered saline (PBS), pH 7.2, prior to loading onto their respective DsbA-CPG or DsbC-CPG affinity columns.

The affinity chromatography steps were performed as described in Table 12.

The resin was DsbA-CPG or DsbC-CPG. The chromatography was in bind and elute mode. The bed height was 6.0 cm (DsbA-CPG) or 5.0 cm (DsbC-CPG). The diameters were 1.6 cm and the volumes were 12.0 or 10.0 mL.

TABLE 12

Affinity chromatography operating conditions

| Step | Buffer Description and pH | Volume Used (CVs) | Flow Rate (mL/min) |
|---|---|---|---|
| Equilibration | PBS, 0.02% sodium azide, pH 7.2 | 3 | 12.0 |
| Load | Extracted 60% AS pellet (Note 1) | 60 mL per run | 1.2 |
| Wash | PBS, 0.02% sodium azide, pH 7.2 | 3 | 1.2 |
| Elution | PBS, 0.02% sodium azide, pH 2.0 (Notes 2 and 3) | 5 | 12.0 |
| Pre-equilibration | 250 mM Tris, 0.02% sodium azide, pH 7.5 | 3 | 12.0 |

The bound DsbA and DsbC antibodies from each column were eluted with 5 CV of elution buffer, collecting the antibodies into a concentrated Tris buffer (in order to maintain a pH of 7.0-7.5, which will minimize aggregation of the antibodies due to the very low elution pH). The elution pool was collected into a beaker that contained 17 mL of 1.0 M Tris, pH 7.5.

SDS-PAGE analysis of the anti-DsbC affinity pool showed a prominent band at ~130 kDa, corresponding to target rabbit anti-DsbC antibodies and other likely product-related higher MW species and lower MW (<75 kDa) species. Under reducing conditions, the major ~130 kDa band reduces to 2 bands: ~50 kDa and ~25 kDa, corresponding to heavy chain and light chain, respectively. Similar SDS-PAGE banding patterns were also observed with the anti-DsbA affinity pool (data not shown).

HPLC-SEC analysis of the anti-DsbA pool showed a distribution of 79% main peak, 19% higher MW species, and 2% lower MW species. For the anti-DsbC pool, 78% main peak, 16% higher MW species and 6% lower MW species was observed. An overall purity of 79% (main peak) was achieved for this step. Prior to functionally testing the pools, an aliquot of the pool be further fractionated to enrich the amount of main peak. Assay performance of the pools, before and after size-exclusion chromatography, was evaluated in the ELISA.

Size Exclusion Chromatography: SEC

In order to gain a higher level of purity, size-exclusion chromatography (SEC) was carried out using a Superdex 200 column (GE Healthcare). Due to a limited quantity of the anti-DsbA affinity pool, an aliquot of the anti-DsbC affinity pool was fractionated first. Operating parameters for the SEC column were as follows. The volume of the column was 1120 mL and the load volume was ≤6 mL (≤5% of 1 CV). The column was equilibrated with PBS, pH 7.2 for 3 CV at a flow rate of 0.5 mL/min. The load was ≤6.0 mL per cycle. One cycle was run for anti-DsbA and two cycles was run for anti-DsbC. The column was developed with PBS, pH 7.2 for 1 CV at 0.5 mL/min. For each cycle, the pH adjusted affinity pool from the rabbit serum was concentrated using an Amicon Ultra 10 kDa filter to a final volume of α 6.0 mL.

A 10 mg aliquot of the anti-DsbC affinity pool was concentrated to a volume of ≤6.0 mL (≤5% of 1 CV) using Amicon Ultra-3 centrifugal filters (Millipore).

The concentrated anti-DsbC affinity pool was loaded onto the SEC column, and the load was chased with equilibration buffer. The column was developed with equilibration buffer and 2.4 mL fractions (2% of the SEC CV) were collected. The main peak pool fractions were 34-37.

Several mock pools were evaluated in the HPLC-SEC assay to determine which series of fractions gave the highest degree of purity (Table 13). A narrower cut (fractions 35-36) showed a distribution of 95.1% main peak, 1.0% HMW, and 3.9% LMW species while a broader cut (fractions 34-37) showed 93.9% main peak, 1.4% high MW and 4.7% low MW species. Since a narrower pooling did not significantly improve purity and had a lower protein mass recovery, the broader pooling scheme was chosen (Table 13).

TABLE 13

HPLC-SEC of anti-DsbC mock pools

| Pooling Scheme | HMWs (%) | Main/ Monomer (%) | LMWs (%) | Conc (mg/mL) | Mass (mg) |
|---|---|---|---|---|---|
| 1) 34-35 | 3.7 | 95.0 | 1.3 | 0.39 | 1.85 |
| 2) 34-36 | 2.2 | 94.5 | 3.3 | 0.49 | 3.53 |
| 3) 35-36 | 1.0 | 95.1 | 3.9 | 0.62 | 2.98 |
| 4) 34-37 | 1.4 | 93.9 | 4.7 | 0.52 | 4.99 |

Concentrations are predicted based on mock pooling.

TSK column: QC Pak GFC 300, Flow rate=0.5 mL/min; run time=15 min

The SEC step increased the amount of monomer from 79% (at the affinity step) to 94%.

Functional Testing Results

Figure 16:
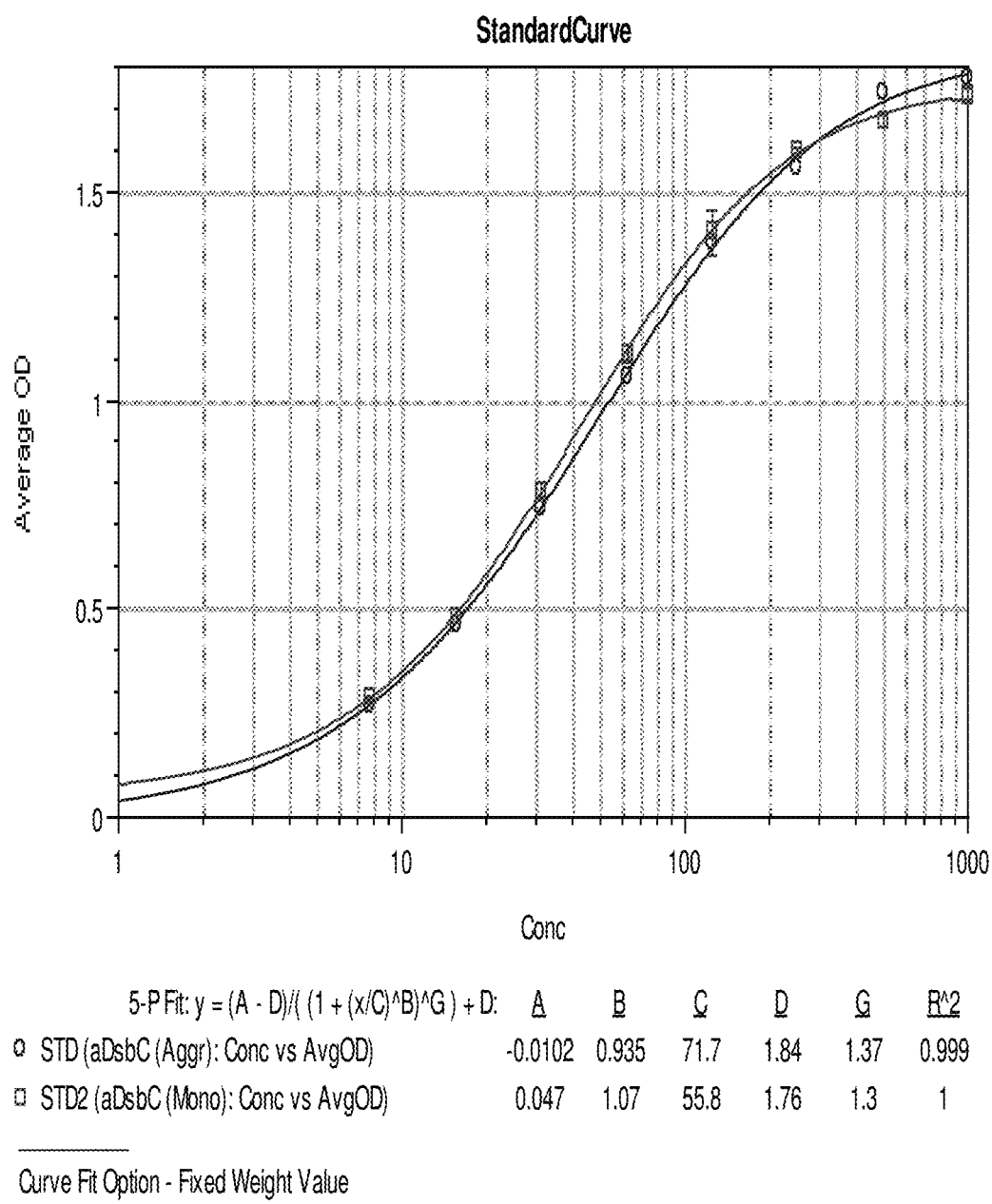
FIG. 16 shows a comparison of the anti-DsbC affinity pool in a direct binding ELISA. Squares represent fractionated material (94% main peak), circles represent non-fractionated material (78% main peak).

The anti-DsbC affinity pools (un-fractionated and fractionated) were evaluated in the direct binding ELISA format to determine if a higher purity was required to give better assay performance. Comparable dose response curves were achieved among the two pools indicating removal of the high MW species was not needed (FIG. 16).

The above results prompted the pursuit of a more sensitive ELISA sandwich assay requiring conjugation of the DsbC antibodies to Horseradish peroxidase (HRP). Successful conjugation (biotinylation) of this type typically requires the antibody pool to be low in high MW species (aggregates).

Figure 17:
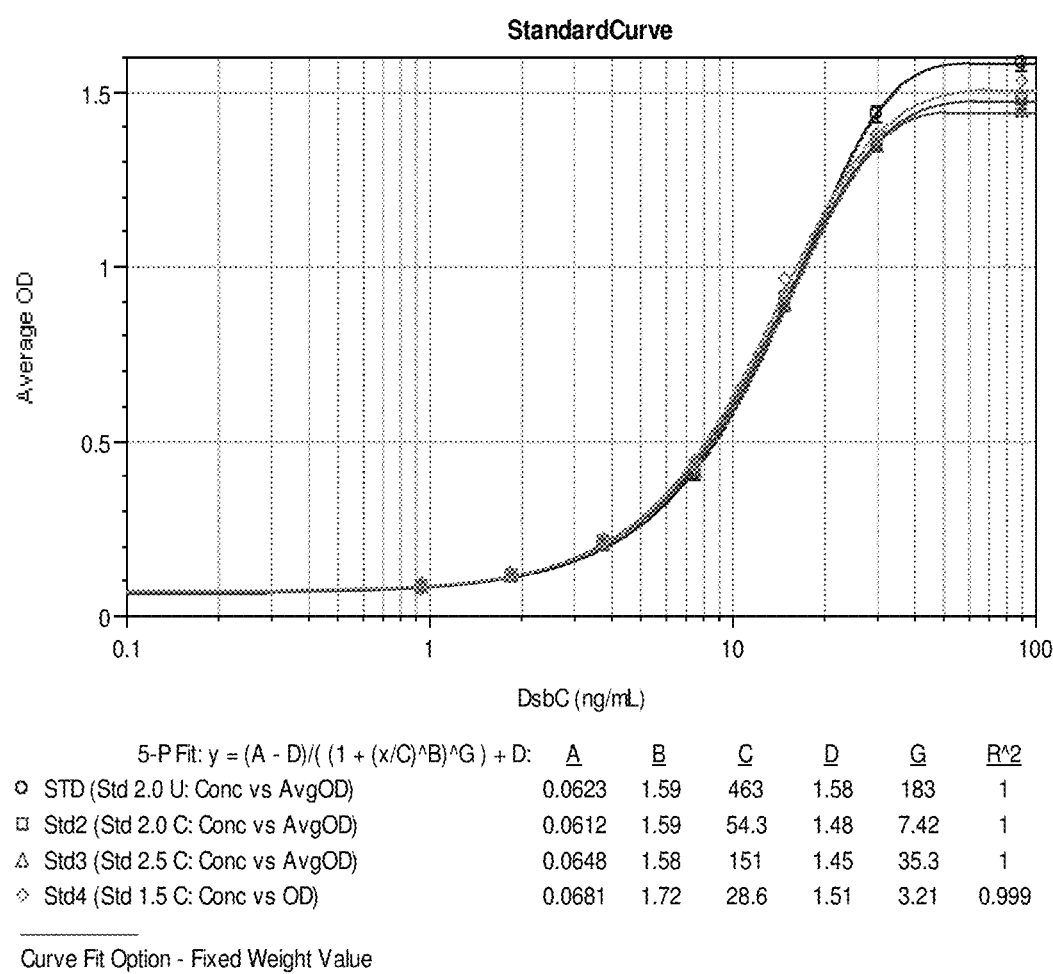
FIG. 17 shows the results of an ELISA using the low aggregate Superdex 200 anti-DsbC affinity pool.

In order to evaluate this step, the low aggregate affinity pool was conjugated to HRP. Using the low aggregate affinity pool as the coat and the low aggregate affinity pool conjugated to HRP for detection, the low aggregate anti-DsbC pool was considered suitable for use in the sandwich ELISA to detect DsbC (FIG. 17).

The final decision was to use the Superdex 200 anti-DsbC pool (lower in aggregate, higher enriched in main peak). With this decision, the remaining half of the anti-DsbC pool and the entire anti-DsbA pool were further fractionation using SEC.

Process B

The SEC step was added to the final purification process (B) as the final chromatographic step to ensure a higher degree of purity with low levels of aggregates.

Fractionation of the anti-DsbA affinity pool and the remaining anti-DsbC affinity pool was done by SEC using a Superdex 200 column as previously described, and using the same operation parameters described above.

The final pooling cuts for anti-DsbA were fractions 35-38, and factions 34-37 for anti-DsbC. These pooling cuts were made to obtain high levels of purity (main peak) and maximum product yield. The final fractionated pools assayed by HPLC-SEC contained 87.3% main peak (anti-DsbA) and 92.5% main peak (anti-DsbC). The SEC step was successful in enriching the main peak by removing the high and low MW species and buffer exchanging the pools into the final formulation buffer (PBS, pH 7.0±0.2).

The purification of DsbA and DsbC led to the successful development of DsbA and DsbC ELISAs.

Example 5. ELISA Detection of DsbA and DsbC

Reagents

Coat antibodies (polyclonal anti-DsbA or polyclonal anti-DsbC) were diluted to about 1.2 mg/mL with PBS and stored at −60° C. or below. After thawing, coat antibodies were stored at 2-8° C. for up to one week from the date of thaw. Standard material (DsbA or DsbC) were diluted to 100 μg/mL and stored at −60° C. or below. Assay control source was diluted with assay diluent to fall within the low and high areas to the standard curve and stored at −60° C. or below. HRP-conjugate (antibody to DsbA or DsbC conjugated to horseradish peroxidase). After thawing, HRP-conjugate antibodies were stored at 2-8° C. for up to one week from the date of thaw. HRP-conjugate anti-DsbA stock I was diluted approximately 1:1 with glycerol for storage at −10° C. to −30° C. HRP-conjugate anti-DsbC stock I was diluted approximately 1:20 with assay diluent for storage at −60° C.

Assay Diluent: 0.15M Sodium chloride [NaCl]/0.1M Sodium phosphate [NaPO4]/0.1% fish gelatin/0.05% Polysorbate 20/0.05% Proclin 300.

Wash Buffer: PBS/0.05% Polysorbate 20.

Coating Buffer: 0.05M Sodium carbonate buffer.

Substrate Solution: SureBlue Reserve™ TMB Microwell Peroxidase Substrate (Kirkegaard & Perry Labs [KPL], catalog #53-00-00 or equivalent).

Stop solution: 0.6 N Sulfuric Acid.

Standard, Control and Sample Preparation

A standard curve was prepared (1000, 100, 50, 25, 12.5, 6.25, 3.13, 1.56, 0.781, 0 ng/mL). An aliquot of the control preparation of each control was thawed on the day of use. Unused thawed control was discarded. Test samples with were diluted with Assay Diluent to fall within the range of the standard curve.

Procedure

Coat Antibody Stock I was diluted with Coating Buffer to yield the standard curve concentrations and desired response ranges. 100 μL of diluted Coat Antibody Stock I was pipetted into each well of microtiter plate and incubated at 2-8° C. for 12 to 72 hours. Each well was washed and aspirated with approximately 400 μL of Wash Buffer 3 times using platewasher and blotted thoroughly. Solution was not removed from wells by inverting plate over waste reservoir. Approximately 200 μL of Assay Diluent was added to each well and incubated for 1 to 2 hours at ambient temperature with agitation. The wash step was repeated.

100 μL per well of diluted standards (in duplicate), controls (in duplicate), and samples was pipetted into appropriate wells. Incubate at ambient temperature for 2 hours ±10 minutes with agitation. Wells were washed as above, the plate was rotated, and the wash step was repeated.

The HRP-Conjugate Stock I was diluted with Assay Diluent to yield a significant OD range between the highest and lowest standards, targeting a maximum OD value of 1.5-2.0 OD. 100 μL of diluted HRP-Conjugate Stock I was pipetted to each well and incubated at ambient temperature for 2 hours ±10 minutes with agitation. Wells were washed as above, the plate was rotated, and the wash step was repeated.

100 μL per well of Substrate Solution was pipetted to the wells and incubated for a sufficient time in the dark at ambient temperature to allow optimal standard curve color development. 100 μL per well of 0.6 N Sulfuric Acid was pipetted.

ODs were read using a platereader using two filters, 450 nm for detection absorbance and 620-630 nm for reference absorbance (reference wavelength was optional).

Calculations and Data Analysis

Sample concentrations were determined by using data-processing software with a minimum 5-parameter logistic curve-fitting program.

The ELISA was used to evaluate DsbA and DsbC removal during the purification of an antibody as described in Example 4.

Example 5. Evaluation of DsbA and DsbC Removal During Purification of a Monoclonal Antibody MAb1 was produced in *E. coli* cells that overexpressed DsbA and DsbC to aid in proper folding and generation of disulfide bonds. Briefly, *E. coli* cells expressing MAb1, DsbA and DsbC were lysed and centrifuged to clarify the lysate. The centrate was then applied to a MabSelect Sure protein A column (MSS). The eluted MSS fractions containing MAb 1 were subsequently applied to CaptoAdhere (Capto) mixed mode chromatography, Poros 50 HS cation exchange chromatography and QSFF anion exchange chromatography, all in bind and elute mode. The pooled QSFF fractions containing MAb1 were then concentrated and formulated using ultrafiltration and diafiltration.

Fractions from each purification step (centrate, MSS protein A, CaptoAdhere, Poros 50 HS, QSFF, UFDF) were assayed for protein concentration, removal of *E. coli* proteins as described below, and presence of DsbA and DsbC as described in Example 3. Results were obtained for six qualification runs.

Removal of Host-Cell Protein (ECP)

The recovery process used for the purification of antibodies has been evaluated for its ability to reduce the level of host-cell proteins (*E. coli* proteins or ECP). Quantitation of ECP was performed on in-process and filtered bulk samples using the ELISA assay described below. These data demonstrate that ECPs in the clinical antibody materials are significantly reduced by the recovery process to levels <50 ng/mg antibody.

The multi-product sandwich ELISA for *E. coli* proteins was used to quantitate the levels of ECP in the pool samples. Affinity-purified goat anti-whole ECP antibodies were immobilized on microtiter plate wells. Dilutions of the pool samples were incubated in the wells, followed by incubation with affinity-purified goat anti-whole ECP conjugated to horseradish peroxidase. The horseradish peroxidase enzymatic activity was detected with o-phenylenediamine dihydrochloride. The ECP was quantitated by reading absorbance at 490 nm in a microtiter plate reader. A four-parameter computer curve-fitting program was used to generate the standard curve and automatically calculate the sample concentration. The assay range for the ELISA was typically 1.56 ng/mL to 50 ng/mL for DsbA and 1.09 ng/mL to 35 ng/mL for DsbC.

Results

The total amount of protein found in each fraction is presented in Table 14.

TABLE 14

Total protein concentrations (mg/ml) of purification fractions.

| Pool | Run 1 | Run 2 | Run 3 | Run 5 | Run 6 |
|---|---|---|---|---|---|
| Centrate | 1.06 | 1.05 | 0.93 | 0.91 | 1.05 |
| MSS | 12.57 | 12.57 | 13.71 | 12.64 | 12.47 |
| Capto | 6.83 | 7.06 | 7.65 | 6.36 | 6.29 |
| Poros | 6.58 | 6.44 | 6.48 | 5.91 | 6.25 |
| QSFF | 4.34 | 4.52 | 4.22 | 3.85 | 3.89 |
| UFDF | 76.818 | 77.452 | 72.07 | 68.189 | 67.411 |

Removal of *E. coli* protein is shown in Table 15.

TABLE 15

Total *E. coli* protein (ng ECP/mg total protein) of purification fractions.

| Pool | Run 1 | Run 2 | Run 3 | Run 5 | Run 6 |
|---|---|---|---|---|---|
| Centrate | 3761682.4 | 3829524 | 4510806 | 4610109.9 | 3362492.1 |
| MSS | 893.9 | 928.6 | 1116 | 1385 | 969.7 |
| Capto | 63.7 | 67.6 | 79.80 | 77.2 | 55.9 |
| Poros | 14.7 | 18.3 | 29.5 | 20.6 | 13.7 |

TABLE 15-continued

Total *E. coli* protein (ng ECP/mg total protein) of purification fractions.

| Pool | Run 1 | Run 2 | Run 3 | Run 5 | Run 6 |
|---|---|---|---|---|---|
| QSFF | 5.1 | 6.9 | 10 | 8 | 5.8 |
| UFDF | 8.7 | 9.6 | 13.2 | 11.1 | 8.4 |

The total amount of DsbA detected in each fraction is presented in Table 16.

TABLE 16

Total DsbA concentration (ng/mL) of purification fractions.

| Pool | Run 1 | Run 2 | Run 3 | Run 5 | Run 6 |
|---|---|---|---|---|---|
| Centrate | 132688 | 169288 | 156320 | 152944 | 150888 |
| MSS | 647 | 607 | 847 | 1171 | 733 |
| Capto | 1.68 | 2.55 | 4.00 | 1.61 | 2.22 |
| Poros | <0.78 | <0.78 | <0.78 | <0.78 | <0.78 |
| QSFF | <0.78 | <0.78 | <0.78 | <0.78 | <0.78 |
| UFDF | <0.78 | <0.78 | <0.78 | <0.78 | <0.78 |

The relative amount of DsbA in each fraction was determined by normalizing the total DsbA in each fraction (Table 16) for the total protein in each fraction (Table 14). Results of the normalized DsbA content is shown in Table 17. The results are presented as ng/ml DsbA/protein concentration.

TABLE 17

Total relative DsbA content (ng DsbA/mg total protein) of purification fractions.

| Pool | Run 1 | Run 2 | Run 3 | Run 5 | Run 6 |
|---|---|---|---|---|---|
| Centrate | 125177.3585 | 161226.6667 | 168086.0215 | 168070.3297 | 143702.8571 |
| MSS | 51.5 | 48.3 | 61.8 | 92.6 | 58.8 |
| Capto | 0.2 | 0.4 | 0.5 | 0.3 | 0.4 |
| Poros | <0.1 | <0.1 | <0.1 | <0.1 | <0.1 |
| QSFF | <0.2 | <0.2 | <0.2 | <0.2 | <0.2 |
| UFDF | <0.01 | <0.01 | <0.01 | <0.01 | <0.01 |

The total amount of DsbC detected in each fraction is presented in Table 18.

TABLE 18

Total DsbC concentration (ng/mL) of purification fractions.

| Pool | Run 1 | Run 2 | Run 3 | Run 5 | Run 6 |
|---|---|---|---|---|---|
| Centrate | 223328 | 283116 | 179370 | 218864 | 232976 |
| MSS | 4594 | 5792 | 5896 | 7765 | 5305 |
| Capto | <1.09 | <1.09 | <1.09 | <1.09 | <1.09 |
| Poros | <1.09 | <1.09 | <1.09 | <1.09 | <1.09 |
| QSFF | <1.09 | <1.09 | <1.09 | <1.09 | <1.09 |
| UFDF | <1.09 | <1.09 | <1.09 | <1.09 | <1.09 |

The relative amount of DsbC in each fraction was determined by normalizing the total DsbC in each fraction (Table 18) for the total protein in each fraction (Table 14). Results of the normalized DsbC content is shown in Table 19. The results are presented as ng/ml DsbA/protein concentration.

TABLE 19

Total relative DsbC content (ng DsbC/mg total protein) of purification fractions.

| Pool | Run 1 | Run 2 | Run 3 | Run 5 | Run 6 |
|---|---|---|---|---|---|
| Centrate | 210687 | 269634 | 192871 | 240510 | 221882 |
| MSS | 365 | 461 | 430 | 614 | 425 |
| Capto | <0.2 | <0.2 | <0.2 | <0.2 | <0.2 |
| Poros | <0.2 | <0.2 | <0.2 | <0.2 | <0.2 |
| QSFF | <0.3 | <0.3 | <0.3 | <0.3 | <0.3 |
| UFDF | <0.015 | <0.015 | <0.015 | <0.015 | <0.015 |

The results of the DsbA and DsbC assays show that both DsbA and DsbC are cleared prior to the ultrafiltration/diafiltration step. DsbA is cleared after the CaptoAdhere step and DsbC is cleared after the MabSelect Sure step.

---
SEQUENCES

E. coli DsbA
Amino Acid Sequence-without leader sequence
AQYEDGKQYTTLEKPVAGAPQVLEFFSFFCPHCYQFEEVLHISDNVKKK
LPEGVKMTKYHVNFMGGDLGKDLTQAWAVAMALGVEDKVTVPLFEGVQK
TQTIRSASDIRDVFINAGIKGEEYDAAWNSFVVKSLVAQQEKAAADVQL
RGVPAMFVNGKYQLNPQGMDTSNMDVFVQQYADTVKYLSEKK (SEQ
ID NO: 1)

Amino Acid Sequence-with leader sequence (in bold)
MKKIWLALAGLVLAFSASAAQYEDGKQYTTLEKPVAGAPQVLEFFSFFCP
HCYQFEEVLHISDNVKKKLPEGVKMTKYHVNFMGGDLGKDLTQAWAVAMA
LGVEDKVTVPLFEGVQKTQTIRSASDIRDVFINAGIKGEEYDAAWNSFVV
KSLVAQQEKAAADVQLRGVPAMFVNGKYQLNPQGMDTSNMDVFVQQYADT
VKYLSEKK (SEQ ID NO: 5)

Nucleic acid sequence
ATGAAAAAGATTTGGCTGGCGCTGGCTGGTTTAGTTTTAGCGTTTAGCGC
ATCGGCGGCGCAGTATGAAGATGGTAAACAGTACACTACCCTGGAAAAAC
CGGTAGCTGGCGCGCCGCAAGTGCTGGAGTTTTTCTCTTTCTTCTGCCCG
CACTGCTATCAGTTTGAAGAAGTTCTGCATATTTCTGATAATGTGAAGAA
AAAACTGCCGGAAGGCGTGAAGATGACTAAATACCACGTCAACTTCATGG
GTGGTGACCTGGGCAAAGATCTGACTCAGGCATGGGCTGTGGCGATGGCG
CTGGGCGTGGAAGACAAAGTGACTGTTCCGCTGTTTGAAGGCGTACAGAA
AACCCAGACCATTCGTTCTGCTTCTGATATCCGCGATGTATTTATCAACG
CAGGTATTAAAGGTGAAGAGTACGACGCGGCGTGGAACAGCTTCGTGGTG
AAATCTCTGGTCGCTCAGCAGGAAAAAGCTGCAGCTGACGTGCAATTCG
TGGCGTTCCGGCGATGTTTGTTAACGGTAAATATCAGCTGAATCCGCAGG
GTATGGATACCAGCAATATGGATGTTTTTGTTCAGCAGTATGCTGATACA
GTGAAATATCTGTCCGAGAAAAAATAA (SEQ ID NO: 2)

E. coli DsbC
Amino acid sequence-without leader sequence
DDAAIQQTLAKMGIKSSDIQPAPVAGMKTVLTNSGVLYITDDGKHIIQGP
MYDVSGTAPVNVTNKMLLKQLNALEKEMIVYKAPQEKHVITVFTDITCGY
CHKLHEQMADYNALGITVRYLAFPRQGLDSDAEKEMKAIWCAKDKNKAFD
DVMAGKSVAPASCDVDIADHYALGVQLGVSGTPAVVLSNGTLVPGYQPPK
EMKEFLDEHQKMTSGK (SEQ ID NO: 3)

Amino Acid Sequence-with leader sequence (in bold)
MKKGFMLFTLLAAFSGFAQADDAAIQQTLAKMGIKSSDIQPAPVAGMKTV
LTNSGVLYITDDGKHIIQGPMYDVSGTAPVNVTNKMLLKQLNALEKEMIV
YKAPQEKHVITVFTDITCGYCHKLHEQMADYNALGITVRYLAFPRQGLDS
DAEKEMKAIWCAKDKNKAFDDVMAGKSVAPASCDVDIADHYALGVQLGVS
GTPAVVLSNGTLVPGYQPPKEMKEFLDEHQKMTSGK (SEQ
ID NO: 6)

Nucleic acid sequence
ATGAAGAAAGGTTTTATGTTGTTTACTTTGTTAGCGGCGTTTTCAGGCTT
TGCTCAGGCTGATGACGCGGCAATTCAACAAACGTTAGCCAAAATGGGCA
TCAAAAGCAGCGATATTCAGCCCGCGCCTGTAGCTGGCATGAAGACAGTT
CTGACTAACAGCGGCGTGTTGTACATCACCGATGATGGTAAACATATCAT
TCAGGGGCCAATGTATGACGTTAGTGGCACGGCTCCGGTCAATGTCACCA
ATAAGATGCTGTTAAAGCAGTTGAATGCGCTTGAAAAAGAGATGATCGTT
TATAAAGCGCCGCAGGAAAAACACGTCATCACCGTGTTTACTGATATTAC
CTGTGGTTACTGCCACAAACTGCATGAGCAAATGGCAGACTACAACGCGC
TGGGGATCACCGTGCGTTATCTTGCTTTCCCGCGCCAGGGGCTGGACAGC
GATGCAGAGAAAGAAATGAAAGCTATCTGGTGTGCGAAAGATAAAAACAA
AGCGTTTGATGATGTGATGGCAGGTAAAAGCGTCGCACCAGCCAGTTGCG
ACGTGGATATTGCCGACCATTACGCACTTGGCGTCCAGCTTGGCGTTAGC
GGTACTCCGGCAGTTGTGCTGAGCAATGGCACACTTGTTCCGGGTTACCA
GCCGCCAAAGAGATGAAAGAATTCCTCGACGAACACCAAAAAATGACCA
GCGGTAAATAA (SEQ ID NO: 4)

---

What is claimed is:

1. A method for quantifying disulfide oxidoreductase C (Dsb C) in a sample, comprising detecting DsbC in the sample using a detection system and comparing the amount of DsbC detected in the sample with the detection of one or more concentrations of an ultrapure DsbC reference standard, wherein ultrapure DsbC comprises at least about 95% monomeric DsbC.

2. The method of claim 1, wherein the ultrapure DsbC reference standard is prepared by the method comprising
   a) adding polyethyleneimine (PEI) to a final concentration of about 0.01% to about 1.0% to a cell lysate comprising the DsbC polypeptide,
   b) clarifying the cell lysate by centrifugation,
   c) applying the clarified cell lysate comprising the DsbC polypeptide to an anion exchange chromatography material,
   d) eluting the DsbC polypeptide from the anion exchange chromatography material to generate an anion exchange eluate comprising the DsbC polypeptide,
   e) applying the anion exchange eluate comprising the DsbC polypeptide to a hydrophobic interaction chromatography (HIC) material,
   f) eluting the DsbC polypeptide from the HIC material to generate a HIC eluate,
   g) applying the HIC eluate comprising the DsbC polypeptide to a size exclusion chromatography,
   h) collecting fractions from the size exclusion chromatography comprising the purified DsbC polypeptide.

3. The method of claim 1, wherein the detection system is an immunoassay.

4. The method of claim 3, wherein the immunoassay comprises antibodies that specifically binds ultrapure DsbC.

5. A method for analyzing a recombinant polypeptide sample for the presence of and/or quantity of DsbC, comprising detecting DsbC in the sample using an immunoassay and comparing the amount of DsbC detected in the sample with the detection of one or more concentrations of an ultrapure DsbC reference standard, wherein the ultrapure DsbC reference standard comprises at least about 95% monomeric DsbC polypeptide.

6. The method of claim 5, wherein the ultrapure DsbC reference standard is prepared by the method comprising
   a) adding polyethyleneimine (PEI) to a final concentration of about 0.01% to about 1.0% to a cell lysate comprising the DsbC polypeptide,
   b) clarifying the cell lysate by centrifugation,
   c) applying the clarified cell lysate comprising the DsbC polypeptide to an anion exchange chromatography material,
   d) eluting the DsbC polypeptide from the anion exchange chromatography material to generate an anion exchange eluate comprising the DsbC polypeptide,
   e) applying the anion exchange eluate comprising the DsbC polypeptide to a hydrophobic interaction chromatography (HIC) material,
   f) eluting the DsbC polypeptide from the HIC material to generate a HIC eluate,
   g) applying the HIC eluate comprising the DsbC polypeptide to a size exclusion chromatography,
   h) collecting fractions from the size exclusion chromatography comprising the purified DsbC polypeptide.

7. The method of claim 5, wherein the immunoassay comprises antibodies that specifically bind ultrapure DsbC.

8. The method of claim 7, wherein the antibodies that specifically bind ultrapure DsbC are polyclonal antibodies.

9. The method of claim 7, wherein the antibodies that specifically bind DsbC are prepared by exposing an animal to the composition comprising a DsbC polypeptide prepared by
   a) adding polyethyleneimine (PEI) to a final concentration of about 0.01% to about 1.0% to a cell lysate comprising the DsbC polypeptide,
   b) clarifying the cell lysate by centrifugation,
   c) applying the clarified cell lysate comprising the DsbC polypeptide to an anion exchange chromatography material,
   d) eluting the DsbC polypeptide from the anion exchange chromatography material to generate an anion exchange eluate comprising the DsbC polypeptide,
   e) applying the anion exchange eluate comprising the DsbC polypeptide to a hydrophobic interaction chromatography (HIC) material,
   f) eluting the DsbC polypeptide from the HIC material to generate a HIC eluate,
   g) applying the HIC eluate comprising the DsbC polypeptide to a size exclusion chromatography,
   h) collecting fractions from the size exclusion chromatography comprising the purified DsbC polypeptide.

10. The method of claim 5, wherein the recombinant polypeptide is prepared in a host cell overexpressing DsbC.

11. The method of claim 5, wherein the recombinant polypeptide preparation is a final purified product.

12. The method of claim 5, wherein the recombinant polypeptide contained in the recombinant polypeptide sample is an antibody or an immunoadhesin.

13. An immunoassay method for detecting DsbC in a sample, wherein the sample is obtained from a recombinant polypeptide preparation or a host cell line, the method comprising:
   (a) contacting a capture antibody that binds DsbC with the sample thereby generating a sample-capture antibody combination material;
   (b) contacting a detection antibody that binds DsbC with the sample-capture antibody combination material; and
   (c) detecting the antibody bound to the sample-capture antibody combination material
   (d) quantifying the level of the detection antibody bound using a standard titration curve and calculating an amount of DsbC present in the sample based on the level of the detection antibody bound wherein the amount of DsbC present in the sample is determined by comparing the standard titration curve with a standard titration curve generated with an ultrapure DsbC composition, wherein the ultrapure DsbC composition comprises at least about 95% monomeric DsbC.

14. The method of claim 13, wherein the ultrapure DsbC in the composition is prepared by the method comprising
   a) adding polyethyleneimine (PEI) to a final concentration of about 0.01% to about 1.0% to a cell lysate comprising the DsbC polypeptide,
   b) clarifying the cell lysate by centrifugation,
   c) applying the clarified cell lysate comprising the DsbC polypeptide to an anion exchange chromatography material,
   d) eluting the DsbC polypeptide from the anion exchange chromatography material to generate an anion exchange eluate comprising the DsbC polypeptide,
   e) applying the anion exchange eluate comprising the DsbC polypeptide to a hydrophobic interaction chromatography (HIC) material,
   f) eluting the DsbC polypeptide from the HIC material to generate a HIC eluate, g) applying the HIC eluate comprising the DsbC polypeptide to a size exclusion chromatography, h) collecting fractions from the size exclusion chromatography comprising the purified DsbC polypeptide.

15. The method of claim 13, wherein the capture antibody and/or detection antibody specifically binds ultrapure DsbC, wherein the ultrapure DsbC composition comprises at least about 95% monomeric DsbC polypeptide.

16. The method of claim 15, wherein the antibody that specifically binds ultrapure DsbC is a polyclonal antibody.

17. The method of claim 13, wherein the polyclonal antibody is generated according to the method comprising a) adding polyethyleneimine (PEI) to a final concentration of about 0.01% to about 1.0% to a cell lysate comprising the DsbC polypeptide, b) clarifying the cell lysate by centrifugation, c) applying the clarified cell lysate comprising the DsbC polypeptide to an anion exchange chromatography material, d) eluting the DsbC polypeptide from the anion exchange chromatography material to generate an anion exchange eluate comprising the DsbC polypeptide, e) applying the anion exchange eluate comprising the DsbC polypeptide to a hydrophobic interaction chromatography (HIC) material, f) eluting the DsbC polypeptide from the HIC material to generate a HIC eluate, g) applying the HIC eluate comprising the DsbC polypeptide to a size exclusion chromatography, h) collecting fractions from the size exclusion chromatography comprising the purified DsbC polypeptide.

18. The method of claim 13, wherein the host cell line overexpresses DsbC.

19. The method of claim 13, wherein the recombinant polypeptide preparation is final purified product.

20. The method of claim 13, wherein the recombinant polypeptide contained in the recombinant polypeptide preparation is an antibody or an immunoadhesin.

21. A quality assay for a pharmaceutical composition comprising a recombinant polypeptide prepared from a bacterial cell, the quality assay comprising subjecting a sample of the pharmaceutical composition to the immunoassay method of claim 13, wherein detection of DsbC in the immunoassay indicates that the pharmaceutical composition is not suitable for therapeutic administration to an animal.

22. The quality assay of claim 21, wherein an amount of DsbC in the pharmaceutical composition of less than about 10 ppm indicates that the pharmaceutical composition is suitable for administration to the animal.

23. The quality assay of claim 21, wherein the bacterial cell is an *E. coli* cell.

24. The quality assay of claim 21, wherein the bacterial cell overexpresses DsbC.

25. The quality assay of claim 21, wherein the sample is cell lysate.

26. The quality assay of claim 21, wherein the recombinant polypeptide preparation is final purified product.

27. The quality assay of claim 21, wherein the recombinant polypeptide contained in the recombinant polypeptide preparation is an antibody or an immunoadhesin.

28. The quality assay of claim 27, wherein the antibody is a multispecific antibody, a bispecific antibody, a half antibody or an antibody fragment.

29. The quality assay of claim 28, wherein the recombinant polypeptide is an IgG1, an IgG2, an IgG3, or an IgG4.

30. The method of claim 1, wherein ultrapure DsbC comprises at least about 98% monomeric DsbC.

31. The method of claim 5, wherein ultrapure DsbC comprises at least about 98% monomeric DsbC.

32. The method of claim 10, wherein the host cell is an *E. coli* cell.

33. The method of claim 11, wherein the recombinant polypeptide preparation has been subjected to one or more chromatographic purification steps.

34. The method of claim 11, wherein the recombinant polypeptide is a protein A eluate.

35. The method of claim 11, wherein the recombinant polypeptide is an exchange chromatography eluate.

36. The method of claim 13, wherein ultrapure DsbC comprises at least about 98% monomeric DsbC.

37. The method of claim 19, wherein the recombinant polypeptide preparation has been subjected to one or more chromatographic purification steps.

38. The method of claim 19, wherein the recombinant polypeptide is a protein A eluate.

39. The method of claim 19, wherein the recombinant polypeptide is an exchange chromatography eluate.

40. The quality assay of claim 22, wherein an amount of DsbC in the pharmaceutical composition of less than about 2 ppm indicates that the pharmaceutical composition is suitable for administration to the animal.

41. The quality assay of claim 22, wherein an amount of DsbC in the pharmaceutical composition of less than about 1 ppm indicates that the pharmaceutical composition is suitable for administration to the animal.

42. The quality assay of claim 22, wherein if the pharmaceutical composition is suitable for administration, the pharmaceutical formulation is further purified and formulated.

43. The quality assay of claim 26, wherein the host cell is an *E. coli* cell.

44. The quality assay of claim 26, wherein the recombinant polypeptide preparation has been subjected to one or more chromatographic purification steps.

45. The quality assay of claim 26, wherein the recombinant polypeptide is a protein A eluate.

46. The quality assay of claim 26, wherein the recombinant polypeptide is an exchange chromatography eluate.

* * * * *